US007273610B2

(12) United States Patent
Nixon et al.

(10) Patent No.: US 7,273,610 B2
(45) Date of Patent: Sep. 25, 2007

(54) ENDOTHELIASE-2 LIGANDS

(75) Inventors: Andrew Nixon, Hanover, MA (US); Edwin L. Madison, San Francisco, CA (US)

(73) Assignee: Dyax Corp., Cambridge, MA (US)

( * ) Notice: Subject to any disclaimer, the term of this patent is extended or adjusted under 35 U.S.C. 154(b) by 165 days.

(21) Appl. No.: 10/916,758

(22) Filed: Aug. 12, 2004

(65) Prior Publication Data

US 2005/0180977 A1 Aug. 18, 2005

Related U.S. Application Data

(60) Provisional application No. 60/495,005, filed on Aug. 14, 2003, provisional application No. 60/520,164, filed on Nov. 14, 2003.

(51) Int. Cl.

| | |
|---|---|
| ***A61K 39/395*** | (2006.01) |
| *C07H 21/04* | (2006.01) |
| *C07K 16/40* | (2006.01) |
| *C12N 5/06* | (2006.01) |

(52) U.S. Cl. .................. 424/146.1; 435/338; 435/69.1; 435/320.1; 530/388.26; 536/23.53

(58) Field of Classification Search ............. 424/146.1; 435/338, 69.1, 320.1; 530/399.26; 536/23.53
See application file for complete search history.

(56) References Cited

U.S. PATENT DOCUMENTS

| | | | | |
|---|---|---|---|---|
| 5,530,101 | A * | 6/1996 | Queen et al. | 530/387.3 |
| 6,734,006 | B2 * | 5/2004 | Xiao et al. | 435/226 |
| 2002/0068320 | A1 | 6/2002 | Shi et al. | 435/69.1 |
| 2004/0001801 | A1 * | 1/2004 | Madison et al. | 424/85.1 |
| 2004/0048335 | A1 | 3/2004 | Baker et al. | 435/69.1 |
| 2004/0067505 | A1 * | 4/2004 | Alvarez et al. | 435/6 |
| 2004/0073015 | A1 | 4/2004 | Baker et al. | 536/23.2 |

FOREIGN PATENT DOCUMENTS

| | | | |
|---|---|---|---|
| EP | 1262193 | | 12/2002 |
| WO | WO 00/78961 | | 2/2000 |
| WO | WO 00/12708 | | 3/2000 |
| WO | WO 00/37504 | | 6/2000 |
| WO | WO 00/50061 | | 8/2000 |
| WO | WO 00/68247 | | 11/2000 |
| WO | WO 01/36604 | * | 5/2001 |
| WO | WO 01/36645 | | 5/2001 |
| WO | WO 01/68848 | | 9/2001 |
| WO | WO 01/96538 | | 12/2001 |
| WO | WO 02/086085 | | 10/2002 |
| WO | WO 02/070648 | | 12/2002 |

OTHER PUBLICATIONS

Burgess et al, Journal of Cell Biology vol. 111 Nov. 1990 2129-2138.*
Lazar et al Molecular and Cellular Biology Mar. 1988 vol. 8 No. 3 1247-1252.*
Schwartz et al, Proc Natl Acad Sci USA vol. 84:6408-6411 (1987).*
Lin et al Biochemistry USA vol. 14:1559-1563 (1975).*
Rudikoff et al. (Proc. Natl. Acad. Sci USA 1982 79:1979).*
Libby et al. (Circulation Res. 89:195-197 (2001).*
International Search Report.
U.S. Appl. No. 60/089,125.
Brown et al., Exs., vol. 79, pp. 233-269 (1997).
Carmeliet and Jain, Nature, vol. 407, pp. 249-257 (2000).
Folkman et al., Science, vol. 235, pp. 442-447 91987).
Genbank entry BAB55376 submitted May 10, 2001.
Genbank entry BAB39741 submitted Sep. 12, 2000.
Genbank entry CAC41266 submitted Jun. 12, 2001.
Genbank entry AX149577 submitted Jun. 12, 2001.
Hanahan and Folkman, Cell, vol. 86, pp. 353-364 (1986).
Jankun et al., Cancer Research, vol. 57, pp. 559-563 (1997).
Lang and Schuller, Br. J. Cancer, vol. 84, pp. 234-243 (2001).
Markland et al., Biochemistry, vol. 35, pp. 8045-8057 (1996).
Min et al., Cancer Research, vol. 56, pp. 2428-2433 (1996).
Moses et al., Science, vol. 248, pp. 1408-1410 (1990).
Sigrist et al., Brief Bioinform, vol. 3, pp. 265-274 (2002).
International Search Report dated Aug. 20, 2005.
International Preliminary Search Report dated Sep. 29, 2005.

* cited by examiner

*Primary Examiner*—Larry R. Helms
*Assistant Examiner*—Lynn Bristol
(74) *Attorney, Agent, or Firm*—Fish & Richardson P.C.

(57) ABSTRACT

Proteins that bind to ET2, such as immunoglobulins that inhibit ET2 with high affinity and selectivity, are provided. The ET2 binding proteins can be used to treat a variety of disorders, including angiogenesis-associated disorders.

13 Claims, 5 Drawing Sheets

Nucleotide sequence of human Endotheliase-2S (SEQ ID NO:93)
(See also GenBank® GI No: 14348013;EMB No: AX149579.1; and Sequence 3 from Patent WO0136604)

ATGGAGAGGGACAGCCACGGGAATGCATCTCCAGCAAGAACACCTTCAGCTGGAGCATCTCCAGCCCAGG
CATCTCCAGCTGGGACACCTCCAGGCCGGGCATCTCCAGCCCAGGCATCTCCAGCCCAGGCATCTCCAGC
TGGGACACCTCCGGGCCGGGCATCTCCAGCCCAGGCATCTCCAGCTGGTACACCTCCAGGCCGGGCATCT
CCAGGCCGGGCATCTCCAGCCCAGGCATCTCCAGCCCGGGCATCTCCGGCTCTGGCATCACTTTCCAGGT
CCTCATCCGGCAGGTCATCATCCGCCAGGTCAGCCTCGGTGACAACCTCCCCAACCAGAGTGTACCTTGT
TAGAGCAACACCAGTGGGGGCTGTACCCATCCGATCATCTCCTGCCAGGTCAGCACCAGCAACCAGGGCC
ACCAGGGAGAGCCCAGGTACGAGCCTGCCCAAGTTCACCTGGCGGGAGGGCCAGAAGCAGCTACCGCTCA
TCGGGTGCGTGCTCCTCCTCATTGCCCTGGTGGTTTCGCTCATCATCCTCTTCCAGTTCTGGCAGGGCCA
CACAGGGATCAGGTACAAGGAGCAGAGGGAGAGCTGTCCCAAGCACGCTGTTCGCTGTGACGGGGTGGTG
GACTGCAAGCTGAAGAGTGACGAGCTGGGCTGCGTGAGGTTTGACTGGGACAAGTCTCTGCTTAAAATCT
ACTCTGGGTCCTCCCATCAGTGGCTTCCCATCTGTAGCAGCAACTGGAATGACTCCTACTCAGAGAAGAC
CTGCCAGCAGCTGGGTTTCGAGAGTGCTCACCGGACAACCGAGGTTGCCCACAGGGATTTTGCCAACAGC
TTCTCAATCTTGAGATACAACTCCACCATCCAGGAAAGCCTCCACAGGTCTGAATGCCCTTCCCAGCGGT
ATATCTCCCTCCAGTGTTCCCACTGCGGACTGAGGGCCATGACCGGGCGGATCGTGGGAGGGGCGCTGGC
CTCGGATAGCAAGTGGCCTTGGCAAGTGAGTCTGCACTTCGGCACCACCCACATCTGTGGAGGCACGCTC
ATTGACGCCCAGTGGGTGCTCACTGCCGCCCACTGCTTCTTCGTGACCCGGGAGAAGGTCCTGGAGGGCT
GGAAGGTGTACGCGGGCACCAGCAACCTGCACCAGTTGCCTGAGGCAGCCTCCATTGCCGAGATCATCAT
CAACAGCAATTACACCGATGAGGAGGACGACTATGACATCGCCCTCATGCGGCTGTCCAAGCCCCTGACC
CTGTCCGCTCACATCCACCCTGCTTGCCTCCCCATGCATGGACAGACCTTTAGCCTCAATGAGACCTGCT
GGATCACAGGCTTTGGCAAGACCAGGGAGACAGATGACAAGACATCCCCCTTCCTCCGGGAGGTGCAGGT
CAATCTCATCGACTTCAAGAAATGCAATGACTACTTGGTCTATGACAGTTACCTTACCCCAAGGATGATG
TGTGCTGGGGACCTTCGTGGGGGCAGAGACTCCTGCCAGGGAGACAGCGGGGGGCCTCTTGTCTGTGAGC
AGAACAACCGCTGGTACCTGGCAGGTGTCACCAGCTGGGGCACAGGCTGTGGCCAGAGAAACAAACCTGG
TGTGTACACCAAAGTGACAGAAGTTCTTCCCTGGATTTACAGCAAGATGGAGAGCGAGGTGCGATTCATA
AAATCCTAA

FIG. 1A

Amino acid sequence of human Endotheliase-2S (SEQ ID NO:94)
(See also GenBank® GI No: 14348014; EMB No:CAC41220.1; and WO0136604)

```
MERDSHGNASPARTPSAGASPAQASPAGTPPGRASPAQASPAQASPAGTPPGRASPAQASPAGTPPGRAS
PGRASPAQASPARASPALASLSRSSSGRSSSARSASVTTSPTRVYLVRATPVGAVPIRSSPARSAPATRA
TRESPGTSLPKFTWREGQKQLPLIGCVLLLIALVVSLIILFQFWQGHTGIRYKEQRESCPKHAVRCDGVV
DCKLKSDELGCVRFDWDKSLLKIYSGSSHQWLPICSSNWNDSYSEKTCQQLGFESAHRTTEVAHRDFANS
FSILRYNSTIQESLHRSECPSQRYISLQCSHCGLRAMTGRIVGGALASDSKWPWQVSLHFGTTHICGGTL
IDAQWVLTAAHCFFVTREKVLEGWKVYAGTSNLHQLPEAASIAEIIINSNYTDEEDDYDIALMRLSKPLT
LSAHIHPACLPMHGQTFSLNETCWITGFGKTRETDDKTSPFLREVQVNLIDFKKCNDYLVYDSYLTPRMM
CAGDLRGGRDSCQGDSGGPLVCEQNNRWYLAGVTSWGTGCGQRNKPGVYTKVTEVLPWIYSKMESEVRFI
KS
```

FIG. 1B

Nucleotide sequence of human Endotheliase-2L (SEQ ID NO:1)
(See also GenBank® GI No:14348015; EMB No:AX149581.1; and Sequence 5 from Patent WO0136604)

ATGGAGAGGGACAGCCACGGGAATGCATCTCCAGCAAGAACACCTTCAGCTGGAGCATCTCCAGCCCAGG
CATCTCCAGCTGGGACACCTCCAGGCCGGGCATCTCCAGCCCAGGCATCTCCAGCCCAGGCATCTCCAGC
TGGGACACCTCCGGGCCGGGCATCTCCAGCCCAGGCATCTCCAGCTGGTACACCTCCAGGCCGGGCATCT
CCAGGCCGGGCATCTCCAGCCCAGGCATCTCCAGCCCGGGCATCTCCGGCTCTGGCATCACTTTCCAGGT
CCTCATCCGGCAGGTCATCATCCGCCAGGTCAGCCTCGGTGACAACCTCCCCAACCAGAGTGTACCTTGT
TAGAGCAACACCAGTGGGGGCTGTACCCATCCGATCATCTCCTGCCAGGTCAGCACCAGCAACCAGGGCC
ACCAGGGAGAGCCCAGGTACGAGCCTGCCCAAGTTCACCTGGCGGGAGGGCCAGAAGCAGCTACCGCTCA
TCGGGTGCGTGCTCCTCCTCATTGCCCTGGTGGTTTCGCTCATCATCCTCTTCCAGTTCTGGCAGGGCCA
CACAGGGATCAGGTACAAGGAGCAGAGGGAGAGCTGTCCCAAGCACGCTGTTCGCTGTGACGGGGTGGTG
GACTGCAAGCTGAAGAGTGACGAGCTGGGCTGCGTGAGGTTTGACTGGGACAAGTCTCTGCTTAAAATCT
ACTCTGGGTCCTCCCATCAGTGGCTTCCCATCTGTAGCAGCAACTGGAATGACTCCTACTCAGAGAAGAC
CTGCCAGCAGCTGGGTTTCGAGAGTGCTCACCGGACAACCGAGGTTGCCCACAGGGATTTTGCCAACAGC
TTCTCAATCTTGAGATACAACTCCACCATCCAGGAAAGCCTCCACAGGTCTGAATGCCCTTCCCAGCGGT
ATATCTCCCTCCAGTGTTCCCACTGCGGACTGAGGGCCATGACCGGGCGGATCGTGGGAGGGGCGCTGGC
CTCGGATAGCAAGTGGCCTTGGCAAGTGAGTCTGCACTTCGGCACCACCCACATCTGTGGAGGCACGCTC
ATTGACGCCCAGTGGGTGCTCACTGCCGCCCACTGCTTCTTCGTGACCCGGGAGAAGGTCCTGGAGGGCT
GGAAGGTGTACGCGGGCACCAGCAACCTGCACCAGTTGCCTGAGGCAGCCTCCATTGCCGAGATCATCAT
CAACAGCAATTACACCGATGAGGAGGACGACTATGACATCGCCCTCATGCGGCTGTCCAAGCCCCTGACC
CTGTCCGCTCACATCCACCCTGCTTGCCTCCCCATGCATGGACAGACCTTTAGCCTCAATGAGACCTGCT
GGATCACAGGCTTTGGCAAGACCAGGGAGACAGATGACAAGACATCCCCCTTCCTCCGGGAGGTGCAGGT
CAATCTCATCGACTTCAAGAAATGCAATGACTACTTGGTCTATGACAGTTACCTTACCCCAAGGATGATG
TGTGCTGGGGACCTTCGTGGGGGCAGAGACTCCTGCCAGGGAGACAGCGGGGGGCCTCTTGTCTGTGAGC
AGAACAACCGCTGGTACCTGGCAGGTGTCACCAGCTGGGGCACAGGCTGTGGCCAGAGAAACAAACCTGG
TGTGTACACCAAAGTGACAGAAGTTCTTCCCTGGATTTACAGCAAGATGGAGAACAGAGCTCAGCGGGTT
GAAAAAGCGTGGACCTACAGGCCAGGCAGGCAGTTGCTGGGCAGATGTTCTCCCAGAAGTATTTTTTTGT
GTAAGGTTGCAATGGACTTTGAAAACGTTTCAGTTTCTGCAGAGGATTTTGTGATAGTTTTTGTTATCAA
GCATTTATGCATGGGAATCCGCTCTTCATGGCCTTTCCCAGCTCTGTTTGTTTTAGTCTTTTTGATTTTC
TTTTTGTTGTTGTTGTTGTCTTTTTTAAAAAACACAAGTGACTCCATTTTGACTCTGACAACTTTCACAG
CTGTCACCAGAATGCTCCCTGAGAACTACCATTCTTTCCCTTTCCCACTTAAAATATTTCATCAGAACCT
CACTACTATCATAAAAGAGTATAAAGTAATAAAATAA

FIG. 2A

Amino acid sequence of human Endotheliase-2L (SEQ ID NO:2)
(See also GenBank® GI No:14348016; EMB No:CAC41221.1; and WO0136604)

MERDSHGNASPARTPSAGASPAQASPAGTPPGRASPAQASPAQASPAGTPPGRASPAQASPAGTPPGRAS
PGRASPAQASPARASPALASLSRSSSGRSSSARSASVTTSPTRVYLVRATPVGAVPIRSSPARSAPATRA
TRESPGTSLPKFTWREGQKQLPLIGCVLLLIALVVSLIILFQFWQGHTGIRYKEQRESCPKHAVRCDGVV
DCKLKSDELGCVRFDWDKSLLKIYSGSSHQWLPICSSNWNDSYSEKTCQQLGFESAHRTTEVAHRDFANS
FSILRYNSTIQESLHRSECPSQRYISLQCSHCGLRAMTGRIVGGALASDSKWPWQVSLHFGTTHICGGTL
IDAQWVLTAAHCFFVTREKVLEGWKVYAGTSNLHQLPEAASIAEIIINSNYTDEEDDYDIALMRLSKPLT
LSAHIHPACLPMHGQTFSLNETCWITGFGKTRETDDKTSPFLREVQVNLIDFKKCNDYLVYDSYLTPRMM
CAGDLRGGRDSCQGDSGGPLVCEQNNRWYLAGVTSWGTGCGQRNKPGVYTKVTEVLPWIYSKMENRAQRV
EKAWTYRPGRQLLGRCSPRSIFLCKVAMDFENVSVSAEDFVIVFVIKHLCMGIRSSWPFPALFVLVFLIF
FLLLLLSFLKNTSDSILTLTTFTAVTRMLPENYHSFPFPLKIFHQNLTTIIKEYKVIK

FIG. 2B

A
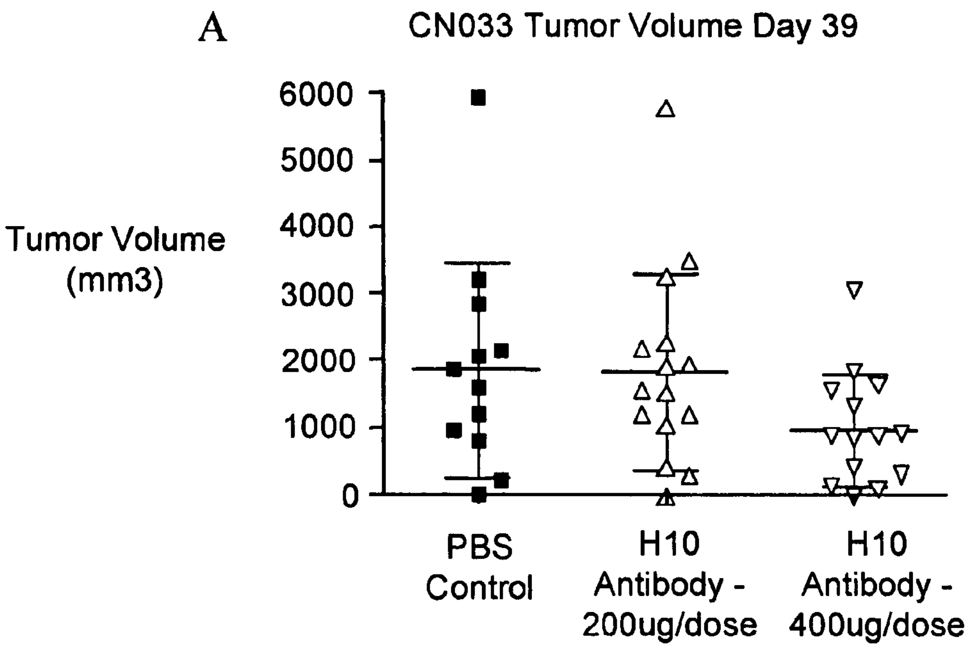
B
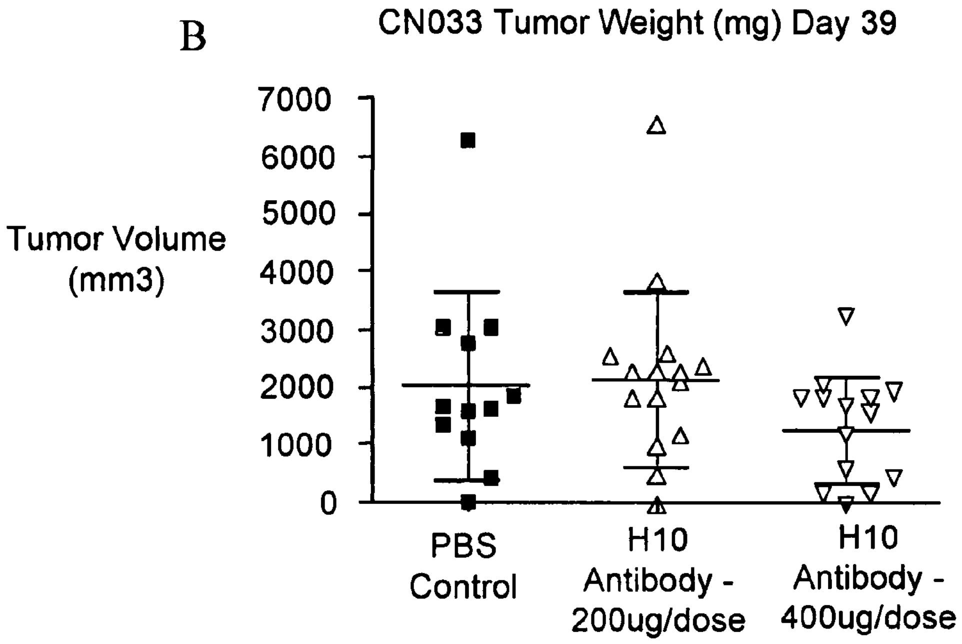
FIG. 3

ENDOTHELIASE-2 LIGANDS

CROSS-REFERENCE TO RELATED APPLICATIONS

This application claims priority to U.S. Application Ser. No. 60/495,005, filed on Aug. 14, 2003, and 60/520,164, filed on Nov. 14, 2003 the contents of both of which are hereby incorporated by reference in their entireties.

BACKGROUND

Angiogenesis is the biological process of producing new blood vessels by sprouting a new branch from an existing blood vessel. While angiogenesis is essential for normal development and growth, it rarely occurs in adulthood except under strictly regulated circumstances (e.g., wound healing; see, for example, Moses et al., *Science,* 248:1408-1410, 1990). Angiogenesis also occurs in a number of diseases, such as cancer, in which new vessels are formed to support the growth and proliferation of both primary and metastatic tumors.

Blood vessels contain endothelial cells surrounded by a basement membrane. One of the first steps in angiogenesis is the degradation of the basement membrane by proteolytic enzymes produced by endothelial cells to form a breach in the membrane through which endothelial cells can migrate and proliferate to form a new vessel sprout. This step can be initiated as follows. First, components of the plasminogen activator (PA)-plasmin system stimulate a protease cascade that results in high concentrations of plasmin and active matrix metalloproteinases (MMPs) at the site of angiogenesis. This increased proteolytic activity leads to degradation of the extracellular matrix (ECM) and invasion of the vessel basal lamina. The release of ECM degradation products leads to chemotaxis of endothelial cells.

Numerous pathological conditions are associated with unwanted angiogenesis. For example, tumors can induce angiogenesis in order to grow beyond minimal size and to metastasize (Hanahan and Folkman *Cell* 1996, 86:353-64). Tumor development is associated with increased release of angiogenesis factors, most prominently of vascular endothelial growth factor (VEGF) (Brown LF et al., *Exs* 1997, 79:233-69). Other disorders characterized by unwanted angiogenesis include, for example, tissue inflammation, arthritis, diabetic retinopathy, and macular degeneration by neovascularization of retina (see, e.g., Folkman et al., *Science,* 235:442-447, 1987).

The endotheliases are a class of membrane proteases that are expressed on cells, particularly endothelial cells.

SUMMARY

In one aspect, the invention features a protein ligand that binds to Endotheliase-2 (ET2) (also referred to herein as an ET2 ligand or ET2-binding ligand). Typically, the ligand is not naturally occurring. In one embodiment, the protein ligand includes a heavy chain variable domain sequence and a light chain variable domain sequence. For example, the ligand is an antibody or an antigen-binding fragment of a full length antibody (also referred to herein as an anti-ET2 antibody).

In one embodiment, the ET2-ligand binds to human ET2 with high affinity and specificity, and thus can be used as diagnostic, prophylactic, or therapeutic agents in vivo and in vitro. For example, the ligand specifically binds to ET2. As used herein, "specific binding" refers to ability (1) to bind to ET2, e.g., human ET2, with an affinity ($K_d$) of better than (i.e., numerically smaller than) $1\times10^{-7}$ M, and (2) to preferentially bind to ET2, e.g., human ET2, with an affinity that is at least two-fold, 10-fold, 50-fold, 100-fold, or better (smaller $K_d$) than its affinity for binding to a non-specific antigen (e.g., BSA, casein) other than ET2.

In one embodiment, the ligand modulates an activity of ET2, e.g., the proteolytic activity of ET2. In one embodiment, the ligand inhibits ET2. For example, the ligand can have a $K_i$ of better than (i.e., numerically less than) 5 nM, 500 pM, 200 pM, 150 pM, 100 pM, 92 pM, or 75 pM, e.g., between 50 nM and 1 pM, or 200 pM and 5 pM. In one embodiment, the ligand specifically inhibits ET2, e.g., relative to another protease (e.g., a protease whose protease domain is between 30-90% identical to the ET2 protease domain, or between 30-60% identical to the ET2 protease domain). For example, the ligand does not inhibit other proteases, e.g., non-ET2 proteases such as trypsinogen-IV, membrane-type serine proteases-1, -6, -7, or Endotheliase-1 (ET 1), e.g., the ligand inhibits another protease (e.g., such other proteases) with an inhibition constant at least 2-, 5-, 10-, 50-, or 100-fold worse (e.g., numerically greater) than its inhibition constant for ET2 (i.e., the ligand does not inhibit the other proteases as well as they inhibit ET2).

In one embodiment, the ligand inhibits angiogenesis, e.g., inhibit proteolysis of one or more ECM components or vessel basement membrane components, in vitro or in vivo. In one embodiment, the ligands have a statistically significant effect (e.g., on an angiogenic process) in one or more of the following assays: a cornea neovascularization assay; a chick embryo chorioallantoic membrane model assay; an assay using SCID mice injected with tumors (e.g., tumors arising from injection of DU145 or LnCaP cell lines, as described in Jankun et al., *Canc. Res.,* 57: 559-563 (1997)); or an assay in which mice are injected with bFGF, to stimulate angiogenesis (e.g., as described by Min et al., *Canc. Res.,* 56: 2428-2433 (1996). Exemplary effects in these assays include an at least 1.5, 2, 5, 10, or 20-fold improvement relative to a negative control (e.g., no antibody).

In one embodiment, the ligand agonizes ET2 (e.g., activates or increases an activity of ET2, e.g., a proteolytic activity), e.g., increases activity at least 0.5, 1.5, 2, 5, 10, or 20 fold.

In one embodiment, the ligand contacts the active site of ET2, e.g., the active site cleft of ET2 or to an amino acid residues that is within 30, 20, or 10 Angstroms of a residue in the catalytic triad of ET2, e.g., histidine 361 of SEQ ID NO:94 or to serine 506 of SEQ ID NO:94, or to an amino acid residue within the sequence LTAAHC (amino acids 357-362 of SEQ ID NO:94) or to an amino acid within the sequence DSCQGDSGGPLV (amino acids 500-511 of SEQ ID NO:94).

The protein ligand typically interacts with, e.g., bind to ET2, preferably human ET2, with high affinity and specificity. For example, the protein ligand binds to human ET2 with an affinity constant ($K_d$) of better than (i.e., numerically smaller than) $10^{-7}$ M, preferably, better than $10^{-8}$ M, $10^{-9}$ M, or $10^{-10}$ M. Preferably, the protein ligand interacts with, e.g., binds to, the extracellular domain of ET2, and most preferably, the extracellular domain of human ET2 (e.g., amino acids 161-562 of ET2-S or 161-688 of ET2-L). In one embodiment, the ET2-ligand binds all or part of the epitope of an antibody described herein, e.g., A10, G3, A6, A7, C8, H9, G10-R2, F3-R2, C6-R2, A4-R3, C1-R3, A2, B5, D2, D5, F8, H10, or C9. The ET2-ligand can inhibit, e.g., competitively inhibit, the binding of an antibody described herein, e.g., A10, G3, A6, A7, C8, H9, G10-R2, F3-R2, C6-R2, A4-R3, C1-R3, A2, B5, D2, D5, F8, H10, or C9, to human ET2. An ET2-ligand may bind to an epitope, e.g., a conformational or a linear epitope, which epitope when bound prevents binding of an antibody described herein, A10, G3, A6, A7, C8, H9, G10-R2, F3-R2, C6-R2, A4-R3, C1-R3, A2, B5, D2, D5, F8, H10, or C9. The epitope can be in close proximity spatially (e.g., within 3, 5, or 10 Angstroms of) or functionally-associated, e.g., an overlapping or adjacent epitope in linear sequence or conformationally similar to the one recognized by the A10, G3, A6, A7, C8, H9, G10-R2, F3-R2, C6-R2, A4-R3, C1-R3, A2, B5, D2, D5, F8, H10, or C9 antibody. In one embodiment, the ET2-ligand binds to an epitope located wholly or partially within the region of the serine protease domain of ET2, e.g., between amino acids 321-562 for ET2-S and 321-688 for ET2-L.

Accordingly, the invention provides anti-ET2 antibodies, antibody fragments, and pharmaceutical compositions thereof, as well as nucleic acids, recombinant expression vectors and host cells for making such antibodies and fragments. An exemplary pharmaceutical composition includes the ligand and a pharmaceutically acceptable carrier. Methods of using the antibodies of the invention to detect ET2, to kill, or to inhibit growth of an ET2-expressing cell, e.g., a ET2-expressing cell, either in vitro or in vivo, are also encompassed by the invention.

Human ET2 is expressed at least on endothelial cells. In one embodiment, an ET2 ligand binds to the cell surface of these cells, and in particular, to the cell surface of living cells, e.g., living endothelial cells. In some cases, the protein ligand can be internalized within the cell, e.g., to permit the intracellular delivery of an agent conjugated to the antibody, e.g., a cytotoxic or a labeling agent. In some embodiments, the protein ligands of the invention can be used to target living normal, benign hyperplastic, and cancerous cells that express ET2.

In one embodiment, an ET ligand binds to ET and alters its conformation and/or catalytic activity, e.g., it enhances catalytic activity or interaction with a substrate.

As used herein, the term "antibody" refers to a protein that includes at least one immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab fragments, $F(ab')_2$, a Fd fragment, a Fv fragments, and dAb fragments) as well as complete antibodies.

The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) *J. Mol. Biol.* 196:901-917). Kabat definitions are used herein. Each VH and VL is typically composed of three CDR's and four FR's, arranged from amino-terminus to carboxy-terminus in the following order: FR1, CDR1, FR2, CDR2, FR3, CDR3, FR4.

An "immunoglobulin domain" refers to a domain from the variable or constant domain of immunoglobulin molecules. Immunoglobulin domains typically contain two β-sheets formed of about seven β-strands, and a conserved disulphide bond (see, e.g., A. F. Williams and A. N. Barclay 1988 *Ann. Rev Immunol.* 6:381-405). The canonical structures of hypervariable loops of an immunoglobulin variable can be inferred from its sequence, as described in Chothia et al. (1992) *J. Mol. Biol.* 227:799-817; Tomlinson et al. (1992) *J. Mol. Biol.* 227: 776-798); and Tomlinson et al. (1995) EMBO J. 14(18):4628-38.

As used herein, an "immunoglobulin variable domain sequence" refers to an amino acid sequence which can form the structure of an immunoglobulin variable domain. For example, the sequence may include all or part of the amino acid sequence of a naturally-occurring variable domain. For example, the sequence may omit one, two or more N- or C-terminal amino acids, internal amino acids, may include one or more insertions or additional terminal amino acids, or may include other alterations. In one embodiment, a polypeptide that includes immunoglobulin variable domain sequence can associate with another immunoglobulin variable domain sequence to form a target binding structure (or "antigen binding site"), e.g., a structure that interacts with ET2, e.g., binds to or inhibits ET2.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region includes three domains, CH1, CH2 and CH3. The light chain constant region includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system. The term "antibody" includes intact immunoglobulins of types IgA, IgG, IgE, IgD, IgM (as well as subtypes thereof). The light chains of the immunoglobulin may be of types kappa or lambda. In one embodiment, the antibody is glycosylated. An antibody can be functional for antibody-dependent cytotoxicity and/or complement-mediated cytotoxicity.

In one embodiment, the HC or LC of an antibody includes sequences that correspond (e.g., are identical to or have a threshold degree of similarity) to an amino acid sequence encoded by a human germline sequence, e.g., the framework regions and/or in the CDRs. For example, the antibody can include sequences from the human DP47 antibody. In one embodiment, one or more codons for the antibody are altered relative to the germline nucleic acid sequence, but are chosen to encode the same amino acid sequence. Codons can be selected, e.g., to optimize expression in a particular system, create restriction enzyme sites, create a silent fingerprint, etc. CDR sequences can also be substantially human, e.g., are at least 70, 80, 85, 87, 90, 91, 92, 93, 94, or 95% identical to a completely human CDR (e.g., a CDR in a human germline sequence or in a mature human antibody). Accordingly, synthetic nucleic acid sequences can be used to encode completely human or substantially human CDRs.

In one embodiment, CDR2 of the antibody HC includes at least 11, 12, 13, 14, or 15 amino acid positions that are identical to the amino acids found in CDR2 of DP47.

As used herein, the term "immunoglobulin" refers to a protein consisting of one or more polypeptides or regions thereof substantially encoded by immunoglobulin genes (e.g., natural or synthetic). Exemplary natural human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 Kd or 214 amino acids) can be encoded by a variable region gene at the $NH_2$-terminus (about 110 amino acids) and a kappa or lambda constant region gene at the COOH—terminus. Full-length immunoglobulin "heavy chains" (about 50 Kd or 446 amino acids), can be similarly encoded by a variable region gene (about 116 amino acids) and one of the other aforementioned constant region genes, e.g., gamma (encoding about 330 amino acids).

The term "antigen-binding fragment" of an antibody (or simply "antibody portion," or "fragment"), as used herein, refers to one or more fragments of a full-length antibody that retain the ability to specifically bind to ET2 (e.g., human ET2). Examples of binding fragments encompassed within the term "antigen-binding fragment" of an antibody include (i) a Fab fragment, a monovalent fragment consisting of the VL, VH, CL and CH1 domains; (ii) a $F(ab')_2$ fragment, a bivalent fragment including two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Monomers and dimers of such single chain antibodies are also intended to be encompassed within the term "antigen-binding fragment" of an antibody. These antibody fragments are obtained using conventional techniques known to those with skill in the art, and the fragments are screened for activity in the same manner as are intact antibodies.

The antibody is preferably monospecific, e.g., a monoclonal antibody, or antigen-binding fragment thereof. The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of a single molecular composition.

The anti-ET2 antibodies can be full-length (e.g., an IgG (e.g., an IgG1, IgG2, IgG3, IgG4), IgM, IgA (e.g., IgA1, IgA2), IgD, and IgE, but preferably an IgG) or can include only an antigen-binding fragment (e.g., a Fab, $F(ab')_2$ or scFv fragment). The antibody, or antigen-binding fragment thereof, can include two heavy chain immunoglobulins and two light chain immunoglobulins, or can be a single chain antibody. The antibodies can, optionally, include a constant region chosen from a kappa, lambda, alpha, gamma, delta, epsilon or a mu constant region gene. A preferred anti-ET2 antibody includes a heavy and light chain constant region substantially from a human antibody, e.g., a human IgG1 constant region or a portion thereof. As used herein, "isotype" refers to the antibody class (e.g., IgM or IgGl) that is encoded by heavy chain constant region genes.

In one embodiment, the antibody (or fragment thereof) is a recombinant or modified anti-ET2 antibody, e.g., a chimeric, a humanized, a deimmunized, or an in vitro generated antibody. The term "recombinant" or "modified" human antibody, as used herein, is intended to include all antibodies that are prepared, expressed, created or isolated by recombinant means, such as antibodies expressed using a recombinant expression vector transfected into a host cell, antibodies isolated from a recombinant, combinatorial antibody library, antibodies isolated from an animal (e.g., a mouse) that is transgenic for human immunoglobulin genes or antibodies prepared, expressed, created or isolated by any other means that involves splicing of human immunoglobulin gene sequences to other DNA sequences. Such recombinant antibodies include humanized, CDR grafted, chimeric, deimmunized, in vitro generated antibodies, and may optionally include constant regions derived from human germline immunoglobulin sequences. In one embodiment, the antibody does not elicit an anti-globulin response in a human.

In other embodiments, the anti-ET2 antibody is a human antibody.

Also within the scope of the invention are antibodies, or antigen-binding fragments thereof, which bind overlapping epitopes of, or competitively inhibit, the binding of the anti-ET2 antibodies disclosed herein to ET2, e.g., antibodies which bind overlapping epitopes of, or competitively inhibit, the binding of monospecific antibodies A10, G3, A6, A7, C8, H9, G10-R2, F3-R2, C6-R2, A4-R3, C1-R3, A2, B5, D2, D5, F8, H10, or C9 to ET2. Any combination of anti-ET2 antibodies is within the scope of the invention, e.g., two or more antibodies that bind to different regions of ET2, e.g., antibodies that bind to two different epitopes on the serine protease domain of ET2, e.g., a bispecific antibody.

In one embodiment, the anti-ET2 antibody, or antigen-binding fragment thereof, includes at least one light or heavy chain variable domain sequence (e.g., at least one light chain immunoglobulin and at least one heavy chain immunoglobulin). Preferably, each immunoglobulin includes a light or a heavy chain variable domain sequence having at least one, two and, preferably, three complementarity determining regions (CDR's) substantially identical to a CDR from a light or heavy chain variable domain sequence of an antibody that interacts with ET2, e.g., an antibody described herein, e.g., A10, G3, A6, A7, C8, H9, G10-R2, F3-R2, C6-R2, A4-R3, C1-R3, A2, B5, D2, D5, F8, H10, or C9. The amino acid and nucleic acid sequences of exemplary light chain and heavy chain variable regions are shown in Table 1. In some embodiments, the residue listed as a "q" in SEQ ID NO:10 and SEQ ID NO:89 of Table 1 and 2 is a lysine.

TABLE 1

Exemplary Sequences

| Antibody | Sequence | Identifier |
|---|---|---|
| C9 VLC Nucleic Acid Sequence | CAGAGCGTCTTGACTCAGCCTGCCTCCGTGTCTGGGTCTCCTGGACAGTC<br>GATCACCATCTCCTGCACTGGAACCAGTAGTGACGTTGGTCATTATAATT<br>ATGTCTCCTGGTACCAACAGCACCCAGGCAAAGCCCCCAAAGTCATGATT<br>TATGATGTCAGTAGTCGGCCCTCCGGGGTTTCTGATCGCTTCTCTGGGTC<br>CAAGTCTGGCAACACGGCCTCCCTGGCCATCTCTGGGCTCCAGGCTGAGG<br>ACGAGGCTGATTATTACTGCAGTTCGTATACAAGCGGTGACACTCTTTAT<br>GTCTTCGGAACTGGGACCAAGGTCACCGTCCTAGGTCAGCCCAAGGCCAA<br>CCCCACTGTCACTCTGTTCCCGCCCTCCTCTGAGGAGCTCCAAGCCAACA<br>AGGCCACACTAGTGTGTCTGATCAGTGACTTCTACCCGGGAGCTGTGACA<br>GTGGCCTGGAAGGCAGATGGCAGCCCCGTCAAGGCGGGAGTGGAGACCAC<br>CAAACCCTCCAAACAGAGCAACAACAAGTACGCGGCCAGCAGCTACCTGA<br>GCCTGACGCCCGAGCAGTGGAAGTCCCACAGAAGCTACAGCTGCCAGGTC<br>ACGCATGAAGGGAGCACCGTGGAGAAGACAGTGGCCCCTGCAGAATGCTC<br>TTAATAA | SEQ ID NO:3 |
| C9 VLC Amino Acid Sequence | QSVLTQPASVSGSPGQSITISCTGTSSDVGHYNYVSWYQQHPGKAPKVMI<br>YDVSSRPSGVSDRFSGSKSGNTASLAISGLQAEDEADYYCSSYTSGDTLY<br>VFGTGTKVTVLGQPKANPTVTLFPPSSEELQANKATLVCLISDFYPGAVT<br>VAWKADGSPVKAGVETTKPSKQSNNKYAASSYLSLTPEQWKSHRSYSCQV<br>THEGSTVEKTVAPAECS | SEQ ID NO:4 |
| C9 VHC Nucleic Acid Sequence | GAAGTTCAATTGTTAGAGTCTGGTGGCGGTCTTGTTCAGCCTGGTGGTTC<br>TTTACGTCTTTCTTGCGCTGCTTCCGGATTCACTTTCTCTCGTTACCCTA<br>TGTTTTGGGTTCGCCAAGCTCCTGGTAAAGGTTTGGAGTGGGTTTCTTAT<br>ATCTCTTCTTCTGGTGGCTTTACTGGTTATGCTGACTCCGTTAAAGGTCG<br>CTTCACTATCTCTAGAGACAACTCTAAGAATACTCTCTACTTGCAGATGA<br>ACAGCTTAAGGGCTGAGGACACTGCAGTCTACTATTGTGCGAGAGGGGGA<br>CCGCGGGGTAACAAGTACTACTTTGACTACTGGGGCCAGGGAACCCTGGT<br>CACCGTCTCAAGCGCCTCCACCAAGGGCCCATCGGTCTTCCCGCTAGC | SEQ ID NO:5 |
| C9 VHC Amino Acid Sequence | EVQLLESGGGLVQPGGSLRLSCAASGFTFSRYPMFWVRQAPGKGLEWVSY<br>ISSSGGFTGYADSVKGRFTISRDNSKNTLYLQMNSLRAEDTAVYYCARGG<br>PRGNKYYFDYWGQGTLVTVSSASTKGPSVFPL | SEQ ID NO:6 |
| B5 VLC Nucleic Acid Sequence | AGCTACGAATTGACTCAGCCACCCTCAGTGTCCGTGTCCCTAGGACAGGC<br>AGCCAACATCTCCTGCTCTGGAGATAGATTGGGGGATAAATATACTTCCT<br>GGTATCAACAACAGTCAGGACAGTCCCCTGTCCTGGTCATCTATCAAGAT<br>AAGAAGCGACCCTCAGGGATCCCCGAGCGATTCTCTGGCTCCTCCTCTGG<br>GAACACAGCCACTCTGACCATCAGCGGGGCCCAGGCCATAGATGAGGCTG<br>CCTATTACTGTCAGGCGTGGGCCACCAATGTGGTTTTCGGCGCTGGGACC<br>AAGCTGACCGTCCTAGGTCAGCCCAAGGCTGCCCCCTCGGTCACTCTGTT<br>CCCGCCCTCCTCTGAGGAGCTTCAAGCCAACAAGGCCACACTGGTGTGTC | SEQ ID NO:7 |

TABLE 1-continued

| Exemplary Sequences | | |
|---|---|---|
| Antibody | Sequence | Identifier |
| | TCATAAGTGACTTCTACCCGGGAGCCGTGACAGTGGCCTGGAAGGCAGAT<br>AGCAGCCCCGTCAAGGCGGGAGTGGAGACCACCACACCCTCCAAACAAAG<br>CAACAACAAGTACGCGGCCAGCAGCTATCTGAGCCTGACGCCTGAGCAGT<br>GGAAGTCCCACAGAAGCTACAGCTGCCAGGTCACGCATGAAGGGAGCACC<br>GTGGAGAAGACAGTGGCCCCTACAGGATGTTCATAATAA | |
| B5 VLC Amino Acid Sequence | SYELTQPPSVSVSLGQAANISCSGDRLGDKYTSWYQQQSGQSPVLVIYQD<br>KKRPSGIPERFSGSSSGNTATLTISGAQAIDEAAYYCQAWATNVVFGAGT<br>KLTVLGQPKAAPSVTLFPPSSEELQANKATLVCLISDFYPGAVTVAWKAD<br>SSPVKAGVETTTPSKQSNNKYAASSYLSLTPEQWKSHRSYSCQVTHEGST<br>VEKTVAPTGCS | SEQ ID NO:8 |
| B5-H10-A2-D2 VHC Nucleic Acid Sequence | GAAGTTCAATTGTTAGAGTCTGGTGGCGGTCTTGTTCAGCCTGGTGGTTC<br>TTTACGTCTTTCTTGCGCTGCTTCCGGATTCACTTTCTCTCGTTACCGTA<br>TGTATTGGGTTCGCCAAGCTCCTGGTAAAGGTTTGGAGTGGGTTTCTTCT<br>ATCTCTCCTTCTGGTGGCGATACTCGTTATGCTGACTCCGTTAAAGGTCG<br>CTTCACTATCTCTAGAGACAACTCTTAGAATACTCTCTACTTGCAGATGA<br>ACAGCTTAAGGGCTGAGGACACTGCAGTCTACTATTGTGCGAGAGGGGGA<br>CCGCGGGGTAACAAGTACTACTTTGACTACTGGGGCCAGGGAACCCTGGT<br>CACCGTCTCAAGCGCCTCCACCAAGGGCCCATCGGTCTTCCCGCTAGC | SEQ ID NO:9 |
| B5-H10-A2-D2 VHC Amino Acid Sequence | EVQLLESGGGLVQPGGSLRLSCAASGFTFSRYRMYWVRQAPGKGLEWVSS<br>ISPSGGDTRYADSVKGRFTISRDNSqNTLYLQMNSLRAEDTAVYYCARGG<br>PRGNKYYFDYWGQGTLVTVSSASTKGPSVFPL | SEQ ID NO:10 |
| F8 VLC Nucleic Acid Sequence | GACATCCAGATGACCCAGTCTCCAGGCACCCTGTCTTTGTCTCCAGGGGA<br>AAGAGTCACCCTCTCCTGCAGGGCCAGTCAGAGTGTTACCAGCAGCGACT<br>TAGCCTGGTACCAGCAGAAACCTGGTCAGGCTCCCAGGCTCCTCATTTCT<br>GGTGCATCCAGCAGGGCCACTGGCATCCCAGACAGGTTCAGTGGCAGTGG<br>GTCTGGGACAGACTTCACCCTCACCATCAGCAGACTGGAACCTGAAGATT<br>TTGCAGTGTATTACTGTCAGCAGTATGGTAACTCACCTGGGACGTTCGGC<br>CAAGGGACCAAGGTGGAAATCAAACGAACTGTGGCTGCACCATCTGTCTT<br>CATCTTCCCGCCATCTGATGAGCAGTTGAAATCTGGAACTGCCTCTGTTG<br>TGTGCCTGCTGAATAACTTCTATCCCAGAGAGGCCAAAGTACAGTGGAAG<br>GTGGATAACGCCCTCCAATCGGGTAACTCCCAGGAGAGTGTCACAGAGCA<br>GGACAGCAAGGACAGCACCTACAGCCTCAGCAGCACCCTGACGCTGAGCA<br>AAGCAGACTACGAGAAACACAAAGTCTACGCCTGCGAAGTCACCCATCAG<br>GGCCTGAGCTCGCCCGTCACAAAGAGCTTCAACAGGGGAGAGTGTTAATA<br>A | SEQ ID NO:11 |

TABLE 1-continued

Exemplary Sequences

| Antibody | Sequence | Identifier |
|---|---|---|
| F8 VLC Amino Acid Sequence | DIQMTQSPGTLSLSPGERVTLSCRASQSVTSSDLAWYQQKPGQAPRLLIS<br>GASSRATGIPDRFSGSGSGTDFTLTISRLEPEDFAVYYCQQYGNSPGTFG<br>QGTKVEIKRTVAAPSVFIFPPSDEQLKSGTASVVCLLNNFYPREAKVQWK<br>VDNALQSGNSQESVTEQDSKDSTYSLSSTLTLSKADYEKHKVYACEVTHQ<br>GLSSPVTKSFNRGEC | SEQ ID NO:12 |
| F8 VHC Nucleic Acid Sequence | GAAGTTCAATTGTTAGAGTCTGGTGGCGGTCTTGTTCAGCCTGGTGGTTC<br>TTTACGTCTTTCTTGCGCTGCTTCCGGATTCACTTTCTCTCGTTACCATA<br>TGTGGTGGGTTCGCCAAGCTCCTGGTAAAGGTTTGGAGTGGGTTTCTGGT<br>ATCTCTTCTTCTCGTGGCATTACTAAGTATGCTGACTCCGTTAAAGGTCG<br>CTTCACTATCTCTAGAGACAACTCTAAGAATACTCTCTACTTGCAGATGA<br>ACAGCTTAAGGGCTGAGGACACTGCAGTCTACTATTGTGCGAGAGGGGGA<br>CCGCGGGGTAACAAGTACTACTTTGACTACTGGGGCCAGGGAACCCTGGT<br>CACCGTCTCAAGCGCCTCCACCAAGGGCCCATCGGTCTTCCCGCTAGC | SEQ ID NO:13 |
| F8 VHC Amino Acid Sequence | EVQLLESGGGLVQPGGSLRLSCAASGFTFSRYHMWWVRQAPGKGLEWVSG<br>ISSSRGITKYADSVKGRFTISRDNSKNTLYLQMNSLRAEDTAVYYCARGG<br>PRGNKYYFDYWGQGTLVTVSSASTKGPSVFPL | SEQ ID NO:14 |
| H10 VLC Nucleic Acid Sequence | GACATCCAGATGACCCAGTCTCCAGGCACCCTGTCTTTGTCTCCAGGGGA<br>AAGAGCCACCCTCTCCTGCAGGGCCAGTCAGAGTGTTAGCAGCAGCTACT<br>TAGCCTGGTACCAGCAGAAACCTGGCCAGGCTCCCAGGCTCCTCATCTAT<br>GGTGCATCCAGCAGGGCCACTGGCATCCCAGACAGGTTCAGTGGCAGTGG<br>GTCTGGGACAGACTTCACTCTCACCATCAGCAGACTGGAGCCTGAAGATT<br>TTGCAGTGTATTACTGTCAGCAGTATGGTAGCTCAACGTGGACGTTCGGC<br>CAAGGGACCAAAGTGGAAATCAAACGAACTGTGGCTGCACCATCTGTCTT<br>CATCTTCCCGCCATCTGATGAGCAGTTGAAATCTGGAACTGCCTCTGTTG<br>TGTGCCTGCTGAATAACTTCTATCCCAGAGAGGCCAAAGTACAGTGGAAG<br>GTGGATAACGCCCTCCAATCGGGTAACTCCCAGGAGAGTGTCACAGAGCA<br>GGACAGCAAGGACAGCACCTACAGCCTCAGCAGCACCCTGACGCTGAGCA<br>AAGCAGACTACGAGAAACACAAAGTCTACGCCTGCGAAGTCACCCATCAG<br>GGCCTGAGCTCGCCCGTCACAAAGAGCTTCAACAGGGGAGAGTGTTAATA<br>A | SEQ ID NO:15 |
| H10 VLC Amino Acid Sequence | DIQMTQSPGTLSLSPGERATLSCRASQSVSSSYLAWYQQKPGQAPRLLIY<br>GASSRATGIPDRFSGSGSGTDFTLTISRLEPEDFAVYYCQQYGSSTWTFG<br>QGTKVEIKRTVAAPSVFIFPPSDEQLKSGTASVVCLLNNFYPREAKVQWK<br>VDNALQSGNSQESVTEQDSKDSTYSLSSTLTLSKADYEKHKVYACEVTHQ<br>GLSSPVTKSFNRGEC | SEQ ID NO:16 |

TABLE 1-continued

Exemplary Sequences

| Antibody | Sequence | Identifier |
|---|---|---|
| A2 VLC Nucleic Acid Sequence | GACATCCAGATGACCCAGTCTCCATCCTTCCTGTCTGCATTTGTAGGAGA<br>CAGGGTCACCATCACTTGCCGGGCCAGTCAGGACATTAGAAGTGATTTAG<br>CCTGGTATCAGCAAACACCAGGGAAAGCCCCAAAGCTCCTGATCTATGCT<br>GCATCCACTTTGAAAGATGGGGCCCCATCAAGATTCAGCGGCAGTGGATC<br>TGGGACAGAATTTACTCTCACAATCAGCAGCCTGCACCCTGAAGATCTTG<br>CGACTTATTACTGTCAACACCTTAATGGTCACCCTGCTTTCGGCCCTGGG<br>ACCAAAGTGAATATCCAAAGAACTGTGGCTGCACCATCTGTCTTCATCTT<br>CCCGCCATCTGATGAGCAGTTGAAATCTGGAACTGCCTCTGTTGTGTGCC<br>TGCTGAATAACTTCTATCCCAGAGAAGCCAAAGTACAGTGGAAGGTGGAT<br>AACGCCCTCCAATCGGGTAACTCCCAGGAGAGTGTCACAGAGCAGGACAG<br>CAAAGACAGCACCTACAGCCTCAGCAGCACCCTGACGCTGAGCAAAGCAG<br>ACTACGAGAAACACAAAGTCTACGCCTGCGAAGTCACCCATCAGGGCCTG<br>AGCTCGCCCGTCACAAAGAGCTTCAACAGGGGAGAGTGTTAATAA | SEQ ID NO:17 |
| A2 VLC Amino Acid Sequence | DIQMTQSPSFLSAFVGDRVTITCRASQDIRSDLAWYQQTPGKAPKLLIYA<br>ASTLKDGAPSRFSGSGSGTEFTLTISSLHPEDLATYYCQHLNGHPAFGPG<br>TKVNIQRTVAAPSVFIFPPSDEQLKSGTASVVCLLNNFYPREAKVQWKVD<br>NALQSGNSQESVTEQDSKDSTYSLSSTLTLSKADYEKHKVYACEVTHQGL<br>SSPVTKSFNRGEC | SEQ ID NO:18 |
| D2 VLC Nucleic Acid Sequence | GACATCCAGATGACCCAGTCTCCATCCTCCCTGTCTGCTTCTGTTGGAGA<br>CAGAGTCACCATCACTTGCCGGGCAAGCCAGACCATTGACAATTATTTGA<br>ATTGGTATCAGCAGAAACCAGGGAAAGCCCCCAAACTCGTGGTCTATGCT<br>GCATCCACTTTGCAAACTAGGGTCCCATCAAGGTTCAGTGGCAGTGGGTC<br>TGGGACAGACTTCACTCTCACCATCGACAGTCTGAAACCTGAAGATTTTG<br>CAACTTACTTCTGTCAACAGGGTTTCAGTAATCCTTGGACGTTCGGCCAA<br>GGGACCACGGTGGCAATGATACGAACTGTGGCTGCACCATCTGTCTTCAT<br>CTTCCCGCCATCTGATGAGCAGTTGAAATCTGGAACTGCCTCTGTTGTGT<br>GCCTGCTGAATAACTTCTATCCCAGAGAGGCCAAAGTACAGTGGAAGGTG<br>GATAACGCCCTCCAATCGGGTAACTCCCAGGAGAGTGTCACAGAGCAGGA<br>CAGCAAGGACAGCACCTACAGCCTCAGCAGCACCCTGACGCTGAGCAAAG<br>CAGACTACGAGAAACACAAAGTCTACGCCTGCGAAGTCACCCATCAGGGC<br>CTGAGCTCGCCCGTCACAAAGAGCTTCAACAGGGGAGAGTGTTAATAA | SEQ ID NO:19 |
| D2 VLC Amino Acid Sequence | DIQMTQSPSSLSASVGDRVTITCRASQTIDNYLNWYQQKPGKAPKLVVYA<br>ASTLQTRVPSRFSGSGSGTDFTLTIDSLKPEDFATYFCQQGFSNPWTFGQ<br>GTTVAMIRTVAAPSVFIFPPSDEQLKSGTASVVCLLNNFYPREAKVQWKV<br>DNALQSGNSQESVTEQDSKDSTYSLSSTLTLSKADYEKHKVYACEVTHQG<br>LSSPVTKSFNRGEC | SEQ ID NO:20 |

TABLE 1-continued

Exemplary Sequences

| Antibody | Sequence | Identifier |
|---|---|---|
| D5 VLC Nucleic Acid Sequence | GACATCCAGATGACCCAGTCTCCAGGCACCCTGTCATTGTCTCCAGGGGA AAGAGGCACCCTCTCCTGCAGGGCCAGTCAGTTTGTTAGTTACAGCTACT TAGCCTGGTACCAGCAGAAGCCTGGCCAGGCTCCCCGGCTCCTCATCTAT GGCGCATCCAGCAGGGCCAAAGGCATCCCAGACAGGTTCAGTGGCAGTGG GTCTGGGACAGACTTCACTCTCACCATCACCAGACTGGAGCCTGAAGACT TTGCAGTTTATTACTGTCAGCAGTATGTTCCCTCAGTTCCGTGGACGTTC GGCCAAGGGACCAAGGTGGAAGTCAAACGAACTGTGGCTGCACCATCTGT CTTCATCTTCCCGCCATCTGATGAGCAGTTGAAATCTGGAACTGCCTCTG TTGTGTGCCTGCTGAATAACTTCTATCCCAGAGAGGCCAAAGTACAGTGG AAGGTGGATAACGCCCTCCAATCGGGTAACTCCCAGGAGAGTGTCACAGA GCAGGACGGCAAGGACAGCACCTACAGCCTCAGCAGCACCCTGACGCTGA GCAAAGCAGACTACGAGGAACACAAAGTCTACGCCTGCGAAGTCACCCAT CAGGGCCTGAGCTCGCCCGTCACAAAGAGCTTCAACAGGGGAGAGTGTTA ATAA | SEQ ID NO:21 |
| D5 VLC Amino Acid Sequence | DIQMTQSPGTLSLSPGERGTLSCRASQFVSYSYLAWYQQKPGQAPRLLIY GASSRAKGIPDRFSGSGSGTDFTLTITRLEPEDFAVYYCQQYVPSVPWTF GQGTKVEVKRTVAAPSVFIFPPSDEQLKSGTASVVCLLNNFYPREAKVQW KVDNALQSGNSQESVTEQDGKDSTYSLSSTLTLSKADYEEHKVYACEVTH QGLSSPVTKSFNRGEC | SEQ ID NO:22 |
| D5 VHC Nucleic Acid Sequence | GAAGTTCAATTGTTAGAGTCTGGTGGCGGTCTTGTTCAGCCTGGTGGTTC TTTACGTCTTTCTTGCGCTGCTTCCGGATTCACTTTCTCTCGTTACGATA TGCATTGGGTTCGCCAAGCTCCTGGTAAAGGTTTGGAGTGGGTTTCTTCT ATCTCTTCTTCTGGTGGCTATACTGCTTATGCTGACTCCGTTAAAGGTCG CTTCACTATCTCTAGAGACAACTCTAAGAATACTCTCTACTTGCAGATGA ACAGCTTAAGGGCTGAGGACACTGCAGTCTACTATTGTGCGAGAGGCGCC CGAGGTACCAGCCAAGGCTACTGGGGCCAGGGAACCCTGGTCACCGTCTC AAGCGCCTCCACCAAGGGCCCATCGGTCTTCCCGCTAGC | SEQ ID NO:23 |
| D5 VHC Amino Acid Sequence | EVQLLESGGGLVQPGGSLRLSCAASGFTFSRYDMHWVRQAPGKGLEWVSS ISSSGGYTAYADSVKGRFTISRDNSKNTLYLQMNSLRAEDTAVYYCARGA RGTSQGYWGQGTLVTVSSASTKGPSVFPL | SEQ ID NO:24 |

In one embodiment, the antibody (or fragment thereof) includes at least one, two and preferably three CDR's from the light or heavy chain variable region of an antibody disclosed herein, e.g., A10, G3, A6, A7, C8, H9, G10-R2, F3-R2, C6-R2, A4-R3, C1-R3, A2, B5, D2, D5, F8, H10, or C9, or a sequence substantially identical thereto, e.g., 80%, 85%, 90%, 95%, 99%, or more, identical. In other embodiments, the antibody (or fragment thereof) can have at least one, two, and preferably three CDR's from the light or heavy chain variable region of an antibody disclosed herein, e.g., A10, G3, A6, A7, C8, H9, G10-R2, F3-R2, C6-R2, A4-R3, C1-R3, A2, B5, D2, D5, F8, H10, or C9. In one preferred embodiment, the antibody, or antigen-binding fragment thereof, includes all six CDR's from the human anti-ET2 antibody, e.g., A10, G3, A6, A7, C8, H9, G10-R2, F3-R2, C6-R2, A4-R3, C1-R3, A2, B5, D2, D5, F8, H10, or C9.

The CDR and framework sequences of some exemplary antibodies are shown in Error! Reference source not found. and Error! Reference source not found. The sequences of the CDRs are recited in SEQ ID NOs:25, 29, 33, 37, 41, 45, 49, 53, 57, 61, 65, 69, 73, 77, 81, 85, 89, and 6 respectively for Table 2 and in SEQ ID NOs: 26, 30, 34, 38, 42, 46, 50, 54, 58, 62, 66, 70, 74, 78, 82, 86, 90, and 4 respectively for Table 3.

TABLE 2

| HC CDRs | | | |
|---|---|---|---|
| Name | H-CDR1 | H-CDR2 | H-CDR3 |
| A10 | RYRMW (residues 31 to 35 of SEQ ID NO: 25) | YISSSGGFTNYADSVKG (residues 50 to 66 of SEQ ID NO: 25) | NARRALPSMDV (residues 99 to 109 of SEQ ID NO: 25) |
| G3 | RYGMS (residues 31 to 35 of SEQ ID NO: 29) | VIYSSGGITRYADSVKG (residues 50 to 66 of SEQ ID NO: 29) | RAPRGEVAFDI (residues 99 to 109 of SEQ ID NO: 29) |
| A6 | RYKMW (residues 31 to 35 of SEQ ID NO: 33) | YISPSGGYTGYADSVKG (residues 50 to 66 of SEQ ID NO: 33) | NARRAFPSMDV (residues 99 to 109 of SEQ ID NO: 33) |
| A7 | RYRMS (residues 31 to 35 of SEQ ID NO: 37) | SISSSGGITTYADSVKG (residues 50 to 66 of SEQ ID NO: 37) | NARRAFPSMDV (residues 99 to 109 of SEQ ID NO: 37) |
| C8 | RYTMS (residues 31 to 35 of SEQ ID NO: 41) | YIVPSGGMTKYADSVKG (residues 50 to 66 of SEQ ID NO: 41) | RAPRGEVAFDI (residues 99 to 109 of SEQ ID NO: 41) |
| H9 | RYSMH (residues 31 to 35 of SEQ ID NO: 45) | SIGPSGGKTKYADSVKG (residues 50 to 66 of SEQ ID NO: 45) | PFRGSYYYFDY (residues 99 to 109 of SEQ ID NO: 45) |
| G10-R2 | RYKMW (residues 31 to 35 of SEQ ID NO: 49) | YISPSGGYTGYADSVKG (residues 50 to 66 of SEQ ID NO: 49) | NARRAFPSMDV (residues 99 to 109 of SEQ ID NO: 49) |
| F3-R2 | RYRMH (residues 31 to 35 of SEQ ID NO: 53) | GISSSGGDTNYADSVKG (residues 50 to 66 of SEQ ID NO: 53) | NARRAFPSMDV (residues 99 to 109 of SEQ ID NO: 53) |
| C6-R2 | RYSMH (residues 31 to 35 of SEQ ID NO: 57) | RIVPSGGTTFYADSVKG (residues 50 to 66 of SEQ ID NO: 57) | NARRAFPSMDV (residues 99 to 109 of SEQ ID NO: 57) |
| A4-R3 | RYNMY (residues 31 to 35 of SEQ ID NO: 61) | GIRPSGGSTQYADSVKG (residues 50 to 66 of SEQ ID NO: 61) | NARRAFPSMDV (residues 99 to 109 of SEQ ID NO: 61) |
| C1-R3 | RYSMH (residues 31 to 35 of SEQ ID NO: 65) | GIRPSGGSTKYADSVKG (residues 50 to 66 of SEQ Id NO: 65) | NARRAFPSMDV (residues 99 to 109 of SEQ ID NO: 65) |
| A2 | RYRMY (residues 31 to 35 of SEQ ID NO: 69) | SISPSGGDTRYADSVKG (residues 50 to 66 of SEQ ID NO: 69) | GGPRGNKYYFDY (residues 98 to 109 of SEQ ID NO: 69) |
| B5 | RYRMY (residues 31 to 35 of SEQ ID NO: 73) | SISPSGGDTRYADSVKG (residues 50 to 66 of SEQ ID NO: 73) | GGPRGNKYYFDY (residues 98 to 109 of SEQ ID NO: 73) |
| D2 | RYRMY (residues 31 to 35 of SEQ ID NO: 77) | SISPSGGDTRYADSVKG (residues 50 to 66 of SEQ ID NO: 77) | GGPRGNKYYFDY (residues 98 to 109 of SEQ ID NO: 77) |
| D5 | RYDMH (residues 31 to 35 of SEQ ID NO: 81) | SISSSGGYTAYADSVKG (residues 50 to 66 of SEQ ID NO: 81) | GARGTSQGY (residues 99 to 107 SEQ ID NO: 81) |
| F8 | RYHMW (residues 31 to 35 of SEQ ID NO: 85) | GISSSRGITKYADSVKG (residues 50 to 66 of SEQ ID NO: 85) | GGPRGNKYYFDY (residues 99 to 110 of SEQ ID NO: 85) |
| H10 | RYRMY (residues 31 to 35 of SEQ ID NO: 89) | SISPSGGDTRYADSVKG (residues 50 to 66 of SEQ ID NO: 89) | GGPRGNKYYFDY (residues 99 to 110 of SEQ ID NO: 89) |
| C9 | RYPMF (residues 31 to 35 of SEQ ID NO: 6) | YISSSGGFTGYADSVKG (residues 50 to 66 of SEQ ID NO: 6) | GGPRGNKYYFDY (residues 99 to 110 of SEQ ID NO: 6) |

TABLE 3

| LC CDRs | | | |
|---|---|---|---|
| Name | L-CDR1 | L-CDR2 | L-CDR3 |
| A10 | SGSSSNIGSNYVY (residues 23 to 35 of SEQ ID NO: 26) | SNNQRPS (residues 51 to 57 of SEQ ID NO: 26) | AAWDDSLSGPV (residues 90 to 100 of SEQ ID NO: 26) |
| G3 | WASQGISNYLA (residues 25 to 35 of SEQ ID NO: 30) NO: 30) | SASTLQS (residues 51 to 57 of SEQ ID | QQANSFPWT (residues 90 to 98 of SEQ ID NO: 30) |
| A6 | RGDRLRSYYSS (residues 23 to 33 of SEQ ID NO: 34) | GRNNRPS (residues 49 to 55x of SEQ ID NO: 34) | SSRDGSGNFL (residues 88 to 97 of SEQ ID NO: 34) |
| A7 | RASQSISSYLN (residues 25 to 35 of SEQ ID NO: 38) | AASSLQS (residues 51 to 57 of SEQ ID NO: 38) | QQLTGYPSIT (residues 90 to 99 of SEQ ID NO: 38) |

TABLE 3-continued

LC CDRs

| Name | L-CDR1 | L-CDR2 | L-CDR3 |
|---|---|---|---|
| C8 | TGTSSDVGGYNYVS (residues 23 to 36 of SEQ ID NO: 42) | DVSKRPS (residues 52 to 58 of SEQ ID NO: 42) | TSYTSSSTWV (residues 91 to 100 of SEQ ID NO: 42) |
| H9 | QASQDTYNRLH (residues 25 to 35 of SEQ ID NO: 46) | DAVNLKR (residues 51 to 57 of SEQ ID NO: 46) | QHSDDLSLA (residues 90 to 98 of SEQ ID NO: 46) |
| G10-R2 | RSSQSLLYSNGYNYLD (residues 25 to 40 of SEQ ID NO: 50) | LGSNRAS (residues 56 to 62 of SEQ ID NO: 50) | MQALQIPRT (residues 95 to 103 of SEQ ID NO: 50) |
| F3-R2 | RASLPVNTWLA (residues 25 to 35 of SEQ ID NO: 54) | AASRLQS (residues 51 to 57 of SEQ ID NO: 54) | QQANTFPYT (residues 90 to 98 of SEQ ID NO: 54) |
| C6-R2 | QGDSLRSYYAS (residues 23 to 33 of SEQ ID NO: 58) | SKSNRPS (residues 49 to 55 of SEQ ID NO: 58) | NSRDSSGNHLV (residues 88 to 98 of SEQ ID NO: 58) |
| A4-R3 | RGDRLRSYYSS (residues 23 to 33 of SEQ ID NO: 62) | GRKNRPS (residues 49 to 55 of SEQ ID NO: 62) | SSRDGSGNFL (residues 88 to 97 of SEQ ID NO: 62) |
| C1-R3 | RASQSISTYLN (residues 25 to 35 of SEQ ID NO: 66) | GASSLVS (residues 51 to 57 of SEQ ID NO: 66) | HQSYITSWT (residues 90 to 98 of SEQ ID NO: 66) |
| A2 | RASQDIRSDLA (residues 25 to 35 of SEQ ID NO: 70) | AASTLKD (residues 51 to 57 of SEQ ID NO: 70) | QHLNGHPA (residues 90 to 97 of SEQ ID NO: 70) |
| B5 | SGDRLGDKYTS (residues 23 to 33 of SEQ ID NO: 74) | QDKKRPS (residues 49 to 55 of SEQ ID NO: 74) | QAWATNVV (residues 88 to 95 of SEQ ID NO: 74) |
| D2 | RASQTIDNYLN (residues 25 to 35 of SEQ ID NO: 78) | AASTLQT (residues 51 to 57 of SEQ ID NO: 78) | QQGFSNPWT (residues 90 to 98 of SEQ ID NO: 78) |
| D5 | RASQFVSYSYLA (residues 25 to 35 of SEQ ID NO: 82) | GASSRAK (residues 52 to 58 of SEQ ID NO: 82) | QQYVPSVPWT (residues 91 to 100 of SEQ ID NO: 82) |
| F8 | RASQSVTSSDLA (residues 25 to 36 of SEQ ID NO: 86) | GASSRAT (residues 52 to 58 of SEQ ID NO: 86) | QQYGNSPGT (residues 91 to 99 of SEQ ID NO: 86) |
| H10 | RASQSVSSSYLA (residues 25 to 36 of SEQ ID NO: 90) | GASSRAT (residues 52 to 58 of SEQ ID NO: 90) | QQYGSSTWT (residues 91 to 99 of SEQ ID NO: 90) |
| C9 | TGTSSDVGHYNYVS (residues 23 to 36 of SEQ ID NO: 4) | DVSSRPS (residues 52 to 58 of SEQ ID NO: 4) | SSYTSGDTLYV (residues 91 to 101 of SEQ ID NO: 4) |

In another preferred embodiment, the antibody (or fragment thereof) includes at least one, two and preferably three CDR's from the light and/or heavy chain variable region of an antibody disclosed herein, e.g., A10, G3, A6, A7, C8, H9, G10-R2, F3-R2, C6-R2, A4-R3, C1-R3, A2, B5, D2, D5, F8, H10, or C9, having an amino acid sequence that differs by no more than 3, 2.5, 2, 1.5, or 1, 0.5 substitutions, insertions or deletions for every 10 amino acids (e.g., the number of differences being proportional to the CDR length) relative to the corresponding CDR's of the disclosed antibody. Further, the antibody, or antigen-binding fragment thereof, can include six CDR's, each of which differs by no more than 3, 2.5, 2, 1.5, or 1, 0.5 substitutions, insertions or deletions for every 10 amino acids relative to the corresponding CDRs of the human anti-ET2 antibody, e.g., A10, G3, A6, A7, C8, H9, G10-R2, F3-R2, C6-R2, A4-R3, C1-R3, A2, B5, D2, D5, F8, H10, or C9.

In one embodiment, the heavy chain variable region includes a CDR1 including the following amino acid sequence: Y-X-M-X-W (SEQ ID NO:95) or R-Y-X-M-X (SEQ ID NO: 96) or R-Y-(SRK)-M-(SYWH) (SEQ ID NO:97), wherein X is any amino acid.

In one embodiment, the heavy chain variable region includes a CDR2 including the following sequence: I/S-I/S-S-X-X-G-X-X-X-X*-Y-A-D-S (SEQ ID NO:98), wherein X is any amino acid and wherein X* may be absent, or (GSVYR)-I-(GSVYR)-(SP)-S-(GR)-G-(STIMYFKD)-T-(AGTFRKNQ)-Y-A-D-S-V-K-G (SEQ ID NO:112) or (GSY)-I-(SVR)-(SP)-S-G-G-(SIYD)-T-(GRKN)-Y-A-D-S-V-K-G (SEQ ID NO:113).

In one embodiment, the heavy chain variable region includes a CDR3 that includes (GN)-(AG)-(RP)-R-(AG)-(FN)-(KP)-(SY)-(MY)-(FD)-(VD)-Y (SEQ ID NO:99) or (GRN)-(AG)-(RP)-(GR)-(AG)-(FNE)-(VKP)-(ASY)-(MYF)-(FD)-(IVD)-Y (SEQ ID NO:100) or one of the following sequences: GPRGNKYY (SEQ ID NO:101) or ARGTSQ (SEQ ID NO:102).

In one embodiment, the light chain variable region includes a CDR1 including the following sequence: R-A-S-Q-S-(IV)-S-(ST)-(SY)-(LY)-(ALN)-A (SEQ ID NO:103) or R-A-S-(LQ)-(STFDP)-(IV)-(STRDN)-(STYN)-(SYWD)-(LYD)-(ALN)-A (SEQ ID NO:104).

In one embodiment, the light chain variable region includes a CDR2 including the following sequence: X-A-S-S-L-X-X (SEQ ID NO:105) or (AG)-A-S-(STR)-(LR)-(AVKQ)-(STKD) (SEQ ID NO:106), wherein X is any amino acid.

In one embodiment, the light chain variable region includes a CDR3 including the following sequence: Q-Q-

X-X-X-X-P-X-T-X (SEQ ID NO:107) or Q-Q-(AGSLY)-(GTVYFN)-(GSTINP)-(STYFN)-(STVP)-(AGSYWP)-(TIW)-T (SEQ ID NO:108).

In one embodiment, the light chain variable region includes a CDR1 including the following sequence: S-X-D-X-X-X-X-X-Y-X-S-W (SEQ ID NO:109) or R-A-S-Q-X-V/I-X-X-X-(X)-L-A/N-W (SEQ ID NO:110), wherein X is any amino acid and wherein (X) may be absent;

In one embodiment, the light chain variable region includes a CDR2 including the following sequence: A-S-S/T-R/L-X-X-G-R (SEQ ID NO:111), wherein X is any amino acid.

In one embodiment, two or three of the CDRs of the HC variable domain sequence match motifs described herein such that the motifs also match a HC variable domain of an antibody described herein. Similarly, in one embodiment, two or three of the CDRs of the LC variable domain sequence match motifs described herein such that the motifs also match a LC variable domain of an antibody described herein. In still another embodiment, the matched motifs for the CDRs are based on a HC and a LC that are paired in an antibody described herein.

In one embodiment, the H1 and H2 hypervariable loops have the same canonical structure as an antibody described herein. In one embodiment, the L1 and L2 hypervariable loops have the same canonical structure as an antibody described herein.

In another embodiment, the light or heavy chain immunoglobulin of the anti-ET2 antibody, or antigen-binding fragment thereof, can further include a light or a heavy chain variable framework that has no more than 3, 2.5, 2, 1.5, or 1, 0.5 substitutions, insertions or deletions for every 10 amino acids in FR1, FR2, FR3, or FR4 relative to the corresponding frameworks of an antibody disclosed herein, e.g., A10, G3, A6, A7, C8, H9, G10-R2, F3-R2, C6-R2, A4-R3, C1-R3, A2, B5, D2, D5, F8, H10, or C9. In one embodiment, the light or heavy chain immunoglobulin of the anti-ET2 antibody, or antigen-binding fragment thereof, further includes a light or a heavy chain variable framework, e.g., FR1, FR2, FR3, or FR4, that is identical to a framework of an antibody disclosed herein, e.g., A10, G3, A6, A7, C8, H9, G10-R2, F3-R2, C6-R2, A4-R3, C1-R3, A2, B5, D2, D5, F8, H10, or C9.

In one embodiment, the light or the heavy chain variable framework can be chosen from: (a) a light or heavy chain variable framework including at least 80%, 90%, 95%, or preferably 100% of the amino acid residues from a human light or heavy chain variable framework, e.g., a light or heavy chain variable framework residue from a human mature antibody, a human germline sequence, a consensus sequence, or an antibody described herein; (b) a light or heavy chain variable framework including from 20% to 80%, 40% to 80%, or 60% to 90% of the amino acid residues from a human light or heavy chain variable framework, e.g., a light or heavy chain variable framework residue from a human mature antibody, a human germline sequence, or a consensus sequence; (c) a non-human framework (e.g., a rodent framework); or (d) a non-human framework that has been modified, e.g., to remove antigenic or cytotoxic determinants, e.g., deimmunized, or partially humanized. In one embodiment, the ET2-ligand is not antigenic in humans.

In one embodiment, the heavy or light chain framework includes an amino acid sequence, which is at least 80%, 85%, 90%, 95%, 97%, 98%, 99% or higher identical to the heavy chain framework of an antibody disclosed herein, e.g., A10, G3, A6, A7, C8, H9, G10-R2, F3-R2, C6-R2, A4-R3, C1-R3, A2, B5, D2, D5, F8, H10, or C9; or which differs at at least 1 or 5 but at less than 40, 30, 20, or 10 residues from, the amino acid sequence of a variable domain of an antibody disclosed herein, e.g., A10, G3, A6, A7, C8, H9, G10-R2, F3-R2, C6-R2, A4-R3, C1-R3, A2, B5, D2, D5, F8, H10, or C9.

In one embodiment, the heavy or light chain variable domain sequence of the ET2 antibody includes an amino acid sequence, which is at least 80%, 85%, 90%, 95%, 97%, 98%, 99% or higher identical to a variable domain sequence of an antibody described herein, e.g., A10, G3, A6, A7, C8, H9, G10-R2, F3-R2, C6-R2, A4-R3, C1-R3, A2, B5, D2, D5, F8, H10, or C9; or which differs at at least 1 or 5 but at less than 40, 30, 20, or 10 residues from a variable domain sequence of an antibody described herein, e.g., A10, G3, A6, A7, C8, H9, G10-R2, F3-R2, C6-R2, A4-R3, C1-R3, A2, B5, D2, D5, F8, H10, or C9.

In one embodiment, an anti-ET2 antibody includes at least one, preferably two, light chain variable regions that include a light chain variable domain sequence of an antibody described herein, e.g., A10, G3, A6, A7, C8, H9, G10-R2, F3-R2, C6-R2, A4-R3, C1-R3, A2, B5, D2, D5, F8, H10, or C9, and at least one, preferably two, heavy chain variable regions that include a heavy chain variable domain sequence of an antibody described herein, e.g., A10, G3, A6, A7, C8, H9, G10-R2, F3-R2, C6-R2, A4-R3, C1-R3, A2, B5, D2, D5, F8, H10, or C9.

In one embodiment, the light or heavy chain variable framework of the anti-ET2 antibody or antigen-binding fragment thereof includes at least one, two, three, four, five, six, seven, eight, nine, ten, fifteen, sixteen, or seventeen amino acid residues from a human light or heavy chain variable framework, e.g., a light or heavy chain variable framework residue from a human mature antibody, a human germline sequence, a consensus sequence, or an antibody described herein. In one embodiment, the amino acid residue from the human light or heavy chain variable framework is the same as the residue found at the same position in a human germline. Preferably, the amino acid residue from the human light or heavy chain variable framework is the most common residue in the human germline at the same position.

An ET2-ligand described herein can be used alone, e.g., can be administered to a subject or used in vitro in non-derivatized or unconjugated forms. In other embodiments, the ET2-ligand can be derivatized, modified or linked to another functional molecule, e.g., another compound, peptide, protein, isotope, cell, or insoluble support. For example, the ET2-ligand can be functionally linked (e.g., by chemical coupling, genetic fusion, non-covalent association or otherwise) to one or more other molecular entities, such as an antibody (e.g., if the ligand is an antibody to form a bi-specific or a multi-specific antibody), a toxin, a radioisotope, a therapeutic (e.g., a cytotoxic or cytostatic) agent or moiety, among others. For example, the ET2-ligand can be coupled to a radioactive ion (e.g., an $\alpha$-, $\gamma$-, or $\beta$-emitter), e.g., iodine ($^{131}I$ or $^{125}I$), yttrium ($^{90}Y$), lutetium ($^{177}Lu$), actinium ($^{225}Ac$), rhenium ($^{186}Re$), or bismuth ($^{212}$ or $^{213}Bi$).

In another aspect, the invention provides, compositions, e.g., pharmaceutical compositions, which include a pharmaceutically acceptable carrier, excipient or stabilizer, and at least one of the ET2-ligands (e.g., antibodies or fragments thereof) described herein. In one embodiment, the compositions, e.g., the pharmaceutical compositions, include a combination of two or more of the aforesaid ET2-ligands.

In another aspect, the invention features a kit that includes an anti-ET2 antibody (or fragment thereof), e.g., an anti-ET2 antibody (or fragment thereof) as described herein, for use alone or in combination with other therapeutic modalities, e.g., a cytotoxic or labeling agent, e.g., a cytotoxic or labeling agent as described herein, along with instructions on how to use the ET2 antibody or the combination of such agents, e.g., to treat, prevent or detect cancerous lesions.

The invention also features nucleic acid sequences that encode a heavy and light chain immunoglobulin or immunoglobulin fragment described herein. For example, the invention features, a first and second nucleic acid encoding a heavy and light chain variable region, respectively, of an anti-ET2 antibody molecule as described herein. In another aspect, the invention features host cells and vectors containing the nucleic acids of the invention.

In another aspect, the invention features, a method of producing an anti-ET2 antibody, or antigen-binding fragment thereof. The method includes: providing a first nucleic acid encoding a heavy chain variable region, e.g., a heavy chain variable region as described herein; providing a second nucleic acid encoding a light chain variable region, e.g., a light chain variable region as described herein; and expressing said first and second nucleic acids in a host cell under conditions that allow assembly of said light and heavy chain variable regions to form an antigen binding protein. The first and second nucleic acids can be linked or unlinked, e.g., expressed on the same or different vector, respectively. The first and second nucleic acids can further encode constant regions of heavy and light chains.

The host cell can be a eukaryotic cell, e.g., a mammalian cell, an insect cell, a yeast cell, or a prokaryotic cell, e.g., *E. coli*. For example, the mammalian cell can be a cultured cell or a cell line. Exemplary mammalian cells include lymphocytic cell lines (e.g., NSO), Chinese hamster ovary cells (CHO), COS cells, oocyte cells, and cells from a transgenic animal, e.g., mammary epithelial cells. For example, nucleic acids encoding the antibodies described herein can be expressed in a transgenic animal. In one embodiment, the nucleic acids are placed under the control of a tissue-specific promoter (e.g., a mammary specific promoter) and the antibody is produced in the transgenic animal. For example, the antibody molecule is secreted into the milk of the transgenic animal, such as a transgenic cow, pig, horse, sheep, goat or rodent.

The invention also features a method of treating, e.g., inhibiting a cellular activity (e.g., cell growth, cell differentiation, cell migration, or cell organization), a physiological activity (e.g., blood vessel growth, organization, etc.) and/or cell or ablating, or killing, a cell, e.g., a normal, benign or hyperplastic cell (e.g., a cell found in pulmonary, breast, renal, urothelial, colonic, prostatic, or hepatic cancer and/or metastasis). The treating may have direct and/or indirect effects on the growth of a cancer, e.g., by targeting a tumor cell directly, or by inhibiting tumor angiogenesis, thereby inhibiting growth of tumor cell indirectly. Methods of the invention include contacting the cell with an ET2-ligand, in an amount sufficient to treat, e.g., inhibit cell growth, or ablate or kill, the cell. The ligand can include a cytotoxic entity. Methods of the invention can be used, for example, to treat or prevent a disorder, e.g., a cancerous (e.g., a malignant or metastatic disorder), or non-cancerous disorder (e.g., a benign or hyperplastic disorder) by administering to a subject an ET2-ligand in an amount effective to treat or prevent such disorder.

A ET2-ligand that increases ET2 activity can be used, for example, to treat or prevent disorders, e.g., a disorder in which increased proteolysis and/or increased angiogenesis is desirable. For example, the ligand can be used to treat a wound (e.g., to assist wound healing). For example, the wound can be a laceration, a burn, or a surgical incision.

The subject method can be used on cells in culture, e.g. in vitro or ex vivo. For example, cancerous or metastatic cells (e.g., pulmonary, breast, renal, urothelial, colonic, prostatic, or hepatic cancer or metastatic cells) can be cultured in vitro in culture medium and the contacting step can be effected by adding the ET2-ligand to the culture medium. The method can be performed on cells (e.g., cancerous or metastatic cells) present in a subject, as part of an in vivo (e.g., therapeutic or prophylactic) protocol. For in vivo embodiments, the contacting step is effected in a subject and includes administering the ET2-ligand to the subject under conditions effective to permit both binding of the ligand to the cell, and the treating, e.g., the inhibiting of cell growth and/or cell division, or the killing or ablating of the cell.

The method of the invention can be used to treat or prevent disorders characterized by unwanted angiogenesis, such as cancerous disorders, e.g., including but are not limited to, solid tumors, soft tissue tumors, and metastatic lesions. Examples of solid tumors include malignancies, e.g., sarcomas, adenocarcinomas, and carcinomas, of the various organ systems, such as those affecting lung, breast, lymphoid, gastrointestinal (e.g., colon), and genitourinary tract (e.g., renal, urothelial cells), pharynx, as well as adenocarcinomas which include malignancies such as most colon cancers, rectal cancer, renal-cell carcinoma, liver cancer, non-small cell carcinoma of the lung, cancer of the small intestine and cancer of the esophagus. Metastatic lesions of the aforementioned cancers can also be treated or prevented using the methods and compositions of the invention.

The method of the invention can be used to treat or prevent disorders in which increased angiogenesis is desirable, e.g., using an ET2-ligand that increases ET2 activity.

The subject can be a mammal, e.g., a primate, preferably a higher primate, e.g., a human (e.g., a patient having, or at risk of, a disorder described herein, e.g., cancer).

The anti-ET2 antibody or fragment thereof, e.g., an anti-ET2 antibody or fragment thereof as described herein, can be administered to the subject systemically (e.g., orally, parenterally, subcutaneously, intravenously, intramuscularly, intraperitoneally, intranasally, transdermally, or by inhalation), topically, or by application to mucous membranes, such as the nose, throat and bronchial tubes. In one embodiment, the protein accumulates at sites of angiogenesis and/or tumor growth in vivo.

The methods of the invention can further include the step of monitoring the subject, e.g., for a reduction in one or more of: a reduction in tumor size; reduction in cancer markers; reduction in the appearance of new lesions, e.g., in a bone scan; a reduction in the appearance of new disease-related symptoms; or decreased or stabilization of size of soft tissue mass; or any parameter related to improvement in clinical outcome. The subject can be monitored in one or more of the following periods: prior to beginning of treatment; during the treatment; or after one or more elements of the treatment have been administered. Monitoring can be used to evaluate the need for further treatment with the same ET2-ligand or for additional treatment with additional agents. Generally, a decrease in one or more of the parameters described above is indicative of the improved condition of the subject.

The ET2-ligand can be used alone in unconjugated form to thereby ablate, kill, or inhibit growth of the ET2-expressing cells. For example, if the ligand is an antibody, the ablation, killing, or growth inhibition can be mediated by an antibody-dependent cell killing mechanisms such as complement-mediated cell lysis and/or effector cell-mediated cell killing. In other embodiments, the ET2-ligand can be bound to a substance, e.g., a cytotoxic agent or moiety, effective to kill or ablate the ET2-expressing cells. For example, the ET2-ligand can be coupled to a radioactive ion (e.g., an α-, γ-, or β-emitter), e.g., iodine ($^{131}I$ or $^{125}I$), yttrium ($^{90}Y$), lutetium ($^{177}Lu$), actinium ($^{225}Ac$), or bismuth ($^{213}Bi$). The methods and compositions of the invention can be used in combination with other therapeutic modalities, e.g., other anti-cancer and/or anti-angiogenic treatments. In one embodiment, the methods of the invention include administering to the subject an ET2-ligand, e.g., an anti-ET2 antibody or fragment thereof, in combination with a cytotoxic agent, in an amount effective to treat or prevent said disorder. The ligand and the cytotoxic agent can be administered simultaneously or sequentially. In other embodiments, the methods and compositions of the invention are used in combination with surgical and/or radiation procedures.

In another aspect, the invention features methods for detecting the presence of an ET2 protein, in a sample, in vitro (e.g., a biological sample, a tissue biopsy, e.g., a cancerous lesion). The subject method can be used to evaluate, e.g., diagnose or stage a disorder described herein, e.g. a cancerous disorder or other disorder characterized by unwanted angiogenesis. The method includes: (i) contacting the sample (and optionally, a reference, e.g., control, sample) with an ET2-ligand, as described herein, under conditions that allow interaction of the ET2-ligand and the ET2 protein to occur; and (ii) detecting formation of a complex between the ET2-ligand, and the sample (and optionally, the reference, e.g., control, sample). Formation of the complex is indicative of the presence of ET2 protein, and can indicate the suitability or need for a treatment described herein. E.g., a statistically significant change in the formation of the complex in the sample relative to the reference sample, e.g., the control sample, is indicative of the presence and/or level of ET2 in the sample. In one embodiment, the ET2-ligand may recognize and/or distinguish between a complex containing active ET2 and a complex containing an inactive (e.g., zymogen) form of ET2.

In yet another aspect, the invention provides a method for detecting the presence of ET2 in vivo (e.g., in vivo imaging in a subject). The subject method can be used to evaluate, e.g., diagnose, localize, or stage a disorder described herein, e.g., a cancerous disorder or other disorder characterized by unwanted angiogenesis. The method includes: (i) administering to a subject (and optionally a control subject) an ET2-ligand (e.g., an antibody or antigen binding fragment thereof), under conditions that allow interaction of the ET2-ligand and the ET2 protein to occur; and (ii) detecting formation of a complex between the ligand and ET2, wherein a statistically significant change in the formation of the complex in the subject relative to the reference, e.g., the control subject or subject's baseline, is indicative of the presence and/or level of the ET2. In other embodiments, a method of diagnosing or staging, a disorder as described herein (e.g., a cancerous disorder or other disorder characterized by unwanted angiogenesis), is provided. The method includes: (i) identifying a subject having, or at risk of having, the disorder; (ii) obtaining a sample of a tissue or cell affected with the disorder; (iii) contacting said sample or a control sample with an ET2-ligand, under conditions that allow interaction of the binding agent and the ET2 protein to occur, and (iv) detecting formation of a complex. A statistically significant alteration in the formation of the complex between the ligand with respect to a reference sample, e.g., a control sample, is indicative of the disorder or the stage of the disorder.

Preferably, the ET2-ligand used in the in vivo and in vitro diagnostic methods is directly or indirectly labeled with a detectable substance to facilitate detection of the bound or unbound binding agent. Suitable detectable substances include various enzymes, prosthetic groups, fluorescent materials, luminescent materials and radioactive materials. In one embodiment, the ET2-ligand is coupled to a radioactive ion, e.g., indium ($^{111}In$), iodine ($^{131}I$ or $^{125}I$), yttrium ($^{90}Y$), actinium ($^{225}Ac$), bismuth ($^{213}Bi$), sulfur ($^{35}S$), carbon ($^{14}C$), tritium ($^{3}H$), rhodium ($^{188}Rh$), or phosphorous ($^{32}P$). In another embodiment, the ligand is labeled with an NMR contrast agent.

The invention also provides polypeptides and nucleic acids that encompass a range of amino acid and nucleic acid sequences.

A ET2-binding ligand can be used to treat or prevent angiogenesis-related disorders, particularly angiogenesis-dependent cancers and tumors.

Angiogenesis-related disorders include, but are not limited to, solid tumors; blood born tumors such as leukemias; tumor metastasis; benign tumors (e.g., hemangiomas, acoustic neuromas, neurofibromas, trachomas, and pyogenic granulomas; rheumatoid arthritis); psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation.

"Angiogenesis-dependent cancers and tumors" are cancers tumors that require, for their growth (expansion in volume and/or mass), an increase in the number and density of the blood vessels supplying then with blood. In one embodiment a ET2-binding ligand causes regression of such cancers and tumors. "Regression" refers to the reduction of tumor mass and size, e.g., a reduction of at least 2, 5, 10, or 25%.

In another aspect, the invention features a method of contacting a cell (in vitro, ex vivo, or in vivo), e.g., an endothelial cell, e.g., an endothelial cell in the vicinity of a cancer, e.g., a tumor. The method can include providing a ligand that interacts with ET2, e.g., a ligand described herein, and contacting the cell with the ligand, in an amount sufficient to form at least one detectable ligand-cell complex. The ligand can include, for example, a label or cytotoxic entity, e.g., an immunoglobulin Fc domain or a cytotoxic drug.

The invention also provides methods for identifying protein ligands (e.g., antibody ligands) of ET2. In one embodiment, a method includes: providing a library and screening the library to identify a member that encodes a protein that binds to the ET2. The screening can be performed in a number of ways. For example, the library can be a display library, e.g., a phage display library or a phagemid library. The phage/phagemid library can be an antibody (e.g., Fab) or Kunitz domain library. Methods utilizing phage display libraries can further include the steps of: recovering phage that bind ET2 and isolating a nucleic acid from the phage, wherein the nucleic acid encodes the protein or polypeptide ligand of ET2. The phage may be eluted from ET2 using a competitor peptide or by altering buffer conditions (e.g., pH).

The ET2 can be recombinantly expressed and can be tagged. The ET2 is purified and attached to a support, e.g., to paramagnetic beads or other magnetically responsive particle. The ET2 can also be expressed on the surface of a cell. The display library can be screened to identify members that specifically bind to the cell, e.g., only if the ET2 is expressed. The ET2 can be human ET2. The ET2 can be treated or mutated to remove glycosylation. Also, a fragment of ET2 may be used, e.g., a serine protease domain.

As used herein, the term "substantially identical" (or "substantially homologous") is used herein to refer to a first amino acid or nucleotide sequence that contains a sufficient number of identical or equivalent (e.g., with a similar side chain, e.g., conserved amino acid substitutions) amino acid residues or nucleotides to a second amino acid or nucleotide sequence such that the first and second amino acid or nucleotide sequences have similar activities. In the case of antibodies, the second antibody has the same specificity and has at least 5%, 10%, 25%, or 50% of the affinity of the first antibody.

Sequences similar or homologous (e.g., at least about 60%, 70%, 80%, 85%, 90%, 95% sequence identity) to the sequences disclosed herein are also part of this application. In some embodiments, the sequence identity can be about 85%, 90%, 91%, 92%, 93%, 94%, 95%, 96%, 97%, 98%, 99% or higher. Alternatively, substantial identity exists when the nucleic acid segments will hybridize under selective hybridization conditions (e.g., highly stringent hybridization conditions), to the complement of the strand encoding the ET2 ligand. The nucleic acids may be present in whole cells, in a cell lysate, or in a partially purified or substantially pure form.

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In one embodiment, the percent identity between two amino acid sequences is determined using the Needleman and Wunsch ((1970) *J. Mol. Biol.* 48:444-453) algorithm which has been incorporated into the GAP program in the GCG software package (Accelrys, San Diego, Calif.), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a Blossum 62 scoring matrix with a gap penalty of 12, a gap extend penalty of 4, and a frameshift gap penalty of 5.

As used herein, the term "homologous" is synonymous with "similarity" and means that a sequence of interest differs from a reference sequence by the presence of one or more amino acid substitutions (although modest amino acid insertions or deletions) may also be present. Presently preferred means of calculating degrees of homology or similarity to a reference sequence are through the use of BLAST algorithms (available from the National Center of Biotechnology Information (NCBI), National Institutes of Health, Bethesda Md.), in each case, using the algorithm default or recommended parameters for determining significance of calculated sequence relatedness. The percent identity between two amino acid or nucleotide sequences can also be determined using the algorithm of E. Meyers and W. Miller ((1989) *CABIOS,* 4:11-17) which has been incorporated into the ALIGN program (version 2.0), using a PAM120 weight residue table, a gap length penalty of 12 and a gap penalty of 4.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

It is understood that the binding agent polypeptides of the invention may have additional conservative or non-essential amino acid substitutions, which do not have a substantial effect on the polypeptide functions. Whether or not a particular substitution will be tolerated, i.e., will not adversely affect desired biological properties, such as binding activity can be determined as described in Bowie, et al. (1990) *Science* 247:1306-1310. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

A "non-essential" amino acid residue is a residue that can be altered from the wild-type sequence of the binding agent, e.g., the antibody, without abolishing or more preferably, without substantially altering a biological activity, whereas an "essential" amino acid residue results in such a change.

Binding affinity can be determined by a variety of methods including equilibrium dialysis, equilibrium binding, gel filtration, ELISA, or spectroscopy (e.g., using a fluorescence assay). These techniques can be used to measure the concentration of bound and free ligand as a function of ligand (or target) concentration. The concentration of bound ligand ([Bound]) is related to the concentration of free ligand ([Free]) and the concentration of binding sites for the ligand on the target where (N) is the number of binding sites per target molecule by the following equation:

$$[Bound]=N\cdot[Free]/((1/K_a)+[Free])$$

It is not always necessary to make an exact determination of $K_a$, though, since sometimes it is sufficient to obtain a quantitative measurement of affinity, e.g., determined using a method such as ELISA or FACS analysis, is proportional to $K_a$, and thus can be used for comparisons, such as determining whether a higher affinity is, e.g., 2 fold higher. Better binding can be indicated by a greater numerical $K_a$, or a lesser numerical $K_d$ than a reference. Unless otherwise noted, binding affinities are determined in phosphate buffered saline at pH7.

The details of one or more non-limiting embodiments of the invention are set forth in the accompanying drawings and the description below. Other features, objects, and advantages of the invention will be apparent from the description and drawings, and from the claims.

DESCRIPTION OF DRAWINGS

FIGS. 1A and 1B provide the nucleotide and amino acid sequence of human ET-2S (SEQ ID NO:93 and SEQ ID NO:94, respectively).

FIGS. 2A and 2B provide the nucleotide and amino acid sequence of human ET-2L (SEQ ID NO:1 and SEQ ID NO:2, respectively).

FIGS. 3A and 3B depict distribution of tumor volumes (5A) and tumor weights (5B) on day 39 for a treatment with the H10 antibody in a mouse model.

DETAILED DESCRIPTION

Endotheliases are an attractive target for the treatment of diseases characterized by unwanted angiogenesis due to the role of these enzymes in the proteolytic processing of extracellular matrix components during new blood vessel formation. Endotheliase-2 (ET2) is a transmembrane serine protease expressed on the surface of endothelial cells. Exemplary nucleic acid and amino acid sequence of two forms of human ET2, ET2-S, and ET-2L (for short and long forms, respectively) are provided in FIGS. 1 and 2. See also WO 01/36604.

This disclosure provides, inter alia, ligands that bind to ET2, e.g., immunoglobulins that inhibit ET2 with high affinity and selectivity. The disclosure also provides methods for identifying proteins, e.g., antibodies, that bind to ET2. In many cases, the identified proteins are at least partially specific.

ET2 is a type-II membrane-type serine protease and a member of the endotheliase class of angiogenesis-associated proteases. ET2 RNA is expressed in endothelial cells and some tumor cell lines (WO 01/36604). ET2 RNA has also been detected in other tissues. The ET2 protein has a transmembrane region at the N-terminus, followed by a single low density lipoprotein-A (LDR-A) receptor domain and a single scavenger-receptor cysteine-rich domain (WO 01/36604). The C-terminus contains a trypsin-like serine protease domain characterized by the presence of the catalytic triad residues histidine, aspartate, and serine, in 3 conserved regions of the protease domain. Three repetitive sequences having the sequence ASPAGTPPGRASP (SEQ ID NO:144) are present near the transmembrane domain and contain a sequence motif for N-myristoylation (WO 01/36604).

Display Libraries

In one embodiment, a display library can be used to identify proteins that bind to the ET2. A display library is a collection of entities; each entity includes an accessible polypeptide component and a recoverable component that encodes or identifies the polypeptide component. The polypeptide component can be of any length, e.g. from three amino acids to over 300 amino acids. In a selection, the polypeptide component of each member of the library is probed with the ET2 and if the polypeptide component binds to the ET2, the display library member is identified, typically by retention on a support.

Retained display library members are recovered from the support and analyzed. The analysis can include amplification and a subsequent selection under similar or dissimilar conditions. For example, positive and negative selections can be alternated. The analysis can also include determining the amino acid sequence of the polypeptide component and purification of the polypeptide component for detailed characterization.

A variety of formats can be used for display libraries. Examples include the following.

Phage Display. One format utilizes viruses, particularly bacteriophages. This format is termed "phage display." The polypeptide component is typically covalently linked to a bacteriophage coat protein. The linkage results form translation of a nucleic acid encoding the polypeptide component fused to the coat protein. The linkage can include a flexible peptide linker, a protease site, or an amino acid incorporated as a result of suppression of a stop codon. Phage display is described, for example, in Ladner et al., U.S. Pat. No. 5,223,409; Smith (1985) *Science* 228:1315-1317; WO 92/18619; WO 91/17271; WO 92/20791; WO 92/15679; WO 93/01288; WO 92/01047; WO 92/09690; WO 90/02809; de Haard et al. (1999) *J. Biol. Chem* 274:18218-30; Hoogenboom et al. (1998) *Immunotechnology* 4:1-20; Hoogenboom et al. (2000) *Immunol Today* 2:371-8; Fuchs et al. (1991) *Bio/Technology* 9:1370-1372; Hay et al. (1992) *Hum Antibod Hybridomas* 3:81-85; Huse et al. (1989) *Science* 246:1275-1281; Griffiths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrard et al. (1991) *Bio/Technology* 9:1373-1377; Rebar et al. (1996) *Methods Enzymol.* 267:129-49; Hoogenboom et al. (1991) *Nuc Acid Res* 19:4133-4137; and Barbas et al. (1991) *PNAS* 88:7978-7982.

Phage display systems have been developed for filamentous phage (phage fl, fd, and M13) as well as other bacteriophage (e.g. T7 bacteriophage and lambdoid phages; see, e.g., Santini (1998) *J. Mol. Biol.* 282:125-135; Rosenberg et al. (1996) *Innovations* 6:1-6; Houshmet al. (1999) *Anal*

*Biochem* 268:363-370). The filamentous phage display systems typically use fusions to a minor coat protein, such as gene III protein, and gene VIII protein, a major coat protein, but fusions to other coat proteins such as gene VI protein, gene VII protein, gene IX protein, or domains thereof can also been used (see, e.g., WO 00/71694). In one embodiment, the fusion is to a domain of the gene III protein, e.g., the anchor domain or "stump," (see, e.g., U.S. Pat. No. 5,658,727 for a description of the gene III protein anchor domain). It is also possible to physically associate the protein being displayed to the coat using a non-peptide linkage, e.g., a non-covalent bond or a non-peptide covalent bond. For example, a disulfide bond and/or c-fos and c-jun coiled-coils can be used for physical associations (see, e.g., Crameri et al. (1993) *Gene* 137:69 and WO 01/05950).

The valency of the polypeptide component can also be controlled. For example, cloning of the sequence encoding the polypeptide component into the complete phage genome results in multivariant display since all replicates of the gene III protein are fused to the polypeptide component. For reduced valency, a phagemid system can be utilized. In this system, the nucleic acid encoding the polypeptide component fused to gene III is provided on a plasmid, typically of length less than 7000 nucleotides. The plasmid includes a phage origin of replication so that the plasmid is incorporated into bacteriophage particles when bacterial cells bearing the plasmid are infected with helper phage, e.g. M13K01. The helper phage provides an intact copy of gene III and other phage genes required for phage replication and assembly. The helper phage has a defective origin such that the helper phage genome is not efficiently incorporated into phage particles relative to the plasmid that has a wild type origin.

Bacteriophage displaying the polypeptide component can be grown and harvested using standard phage preparatory methods, e.g. PEG precipitation from growth media.

After selection of individual display phages, the nucleic acid encoding the selected peptide components is amplified by infecting cells using the selected phages. Individual colonies or plaques can be picked, the corresponding nucleic acid can be isolated and sequenced.

Cell-based Display. In still another format the library is a cell-display library. Proteins are displayed on the surface of a cell, e.g., a eukaryotic or prokaryotic cell. Exemplary prokaryotic cells include *E. coli* cells, *B. subtilis* cells, spores (see, e.g., Lu et al. (1995) *Biotechnology* 13:366). Exemplary eukaryotic cells include yeast (e.g., *Saccharomyces cerevisiae, Schizosaccharomyces pombe, Hanseula*, or *Pichia pastoris*). Yeast surface display is described, e.g., in Boder and Wittrup (1997) *Nat. Biotechnol.* 15:553-557 and WO 03/029,456. This application describes a yeast display system that can be used to display immunoglobulin proteins such as Fab fragments, and the use of mating to generate combinations of heavy and light chains.

In one embodiment, variegated nucleic acid sequences are cloned into a vector for yeast display. The cloning joins the variegated sequence with a domain (or complete) yeast cell surface protein, e.g., Aga2, Aga1, Flo1, or Gas1. A domain of these proteins can anchor the polypeptide encoded by the variegated nucleic acid sequence by a transmembrane domain (e.g., Flo1) or by covalent linkage to the phospholipid bilayer (e.g., Gas1). The vector can be configured to express two polypeptide chains on the cell surface such that one of the chains is linked to the yeast cell surface protein. For example, the two chains can be immunoglobulin chains.

Ribosome Display. RNA and the polypeptide encoded by the RNA can be physically associated by stabilizing ribosomes that are translating the RNA and have the nascent polypeptide still attached. Typically, high divalent $Mg^{2+}$ concentrations and low temperature are used. See, e.g., Mattheakis et al. (1994) *Proc. Natl. Acad. Sci. USA* 91:9022 and Hanes et al. (2000) *Nat Biotechnol.* 18:1287-92; Hanes et al. (2000) *Methods Enzymol.* 328:404-30. and Schaffitzel et al. (1999) *J Immunol Methods.* 231(1-2):119-35.

Peptide-Nucleic Acid Fusions. Another format utilizes peptide-nucleic acid fusions. Polypeptide-nucleic acid fusions can be generated by the in vitro translation of mRNA that include a covalently attached puromycin group, e.g., as described in Roberts and Szostak (1997) *Proc. Natl. Acad. Sci. USA* 94:12297-12302, and U.S. Pat. No. 6,207,446. The mRNA can then be reverse transcribed into DNA and crosslinked to the polypeptide.

Other Display Formats. Yet another display format is a non-biological display in which the polypeptide component is attached to a non-nucleic acid tag that identifies the polypeptide. For example, the tag can be a chemical tag attached to a bead that displays the polypeptide or a radiofrequency tag (see, e.g., U.S. Pat. No. 5,874,214).

Scaffolds. Scaffolds for display can include: antibodies (e.g., Fab fragments, single chain Fv molecules (scFV), single domain antibodies, camelid antibodies, and camelized antibodies); T-cell receptors; MHC proteins; extracellular domains (e.g., fibronectin Type III repeats, EGF repeats); protease inhibitors (e.g., Kunitz domains, ecotin, BPTI, and so forth); TPR repeats; trifoil structures; zinc finger domains; DNA-binding proteins; particularly monomeric DNA binding proteins; RNA binding proteins; enzymes, e.g., proteases (particularly inactivated proteases), RNase; chaperones, e.g., thioredoxin, and heat shock proteins; and intracellular signaling domains (such as SH2 and SH3 domains).

Appropriate criteria for evaluating a scaffolding domain can include: (1) amino acid sequence, (2) sequences of several homologous domains, (3) 3-dimensional structure, and/or (4) stability data over a range of pH, temperature, salinity, organic solvent, oxidant concentration. In one embodiment, the scaffolding domain is a small, stable protein domains, e.g., a protein of less than 100, 70, 50, 40 or 30 amino acids. The domain may include one or more disulfide bonds or may chelate a metal, e.g., zinc.

Examples of small scaffolding domains include: Kunitz domains (58 amino acids, 3 disulfide bonds), *Cucurbida maxima* trypsin inhibitor domains (31 amino acids, 3 disulfide bonds), domains related to guanylin (14 amino acids, 2 disulfide bonds), domains related to heat-stable enterotoxin IA from gram negative bacteria (18 amino acids, 3 disulfide bonds), EGF domains (50 amino acids, 3 disulfide bonds), kringle domains (60 amino acids, 3 disulfide bonds), fungal carbohydrate-binding domains (35 amino acids, 2 disulfide bonds), endothelin domains (18 amino acids, 2 disulfide bonds), and Streptococcal G IgG-binding domain (35 amino acids, no disulfide bonds).

Examples of small intracellular scaffolding domains include SH2, SH3, and EVH domains. Generally, any modular domain, intracellular or extracellular, can be used.

Another useful type of scaffolding domain is the immunoglobulin (Ig) domain. Methods using immunoglobulin domains for display are described below (see, e.g., "Antibody Display Libraries").

Display technology can also be used to obtain ligands, e.g., antibody ligands that bind particular epitopes of a target. This can be done, for example, by using competing non-target molecules that lack the particular epitope or are mutated within the epitope, e.g., with alanine. Such non-target molecules can be used in a negative selection procedure as described below, as competing molecules when binding a display library to the target, or as a pre-elution agent, e.g., to capture in a wash solution dissociating display library members that are not specific to the target.

Iterative Selection. In one preferred embodiment, display library technology is used in an iterative mode. A first display library is used to identify one or more ligands for a target. These identified ligands are then varied using a mutagenesis method to form a second display library. Higher affinity ligands are then selected from the second library, e.g., by using higher stringency or more competitive binding and washing conditions.

In some implementations, the mutagenesis is targeted to regions known or likely to be at the binding interface. If, for example, the identified ligands are antibodies, then mutagenesis can be directed to the CDR regions of the heavy or light chains as described herein. Further, mutagenesis can be directed to framework regions near or adjacent to the CDRs. In the case of antibodies, mutagenesis can also be limited to one or a few of the CDRs, e.g., to make precise step-wise improvements. Likewise, if the identified ligands are enzymes, mutagenesis can be directed to the active site and vicinity.

Some exemplary mutagenesis techniques include: error-prone PCR (Leung et al. (1989) *Technique* 1:11-15), recombination, DNA shuffling using random cleavage (Stemmer (1994) *Nature* 389-391; termed "nucleic acid shuffling"), random chimeragenesis on transient templates (RACHITT™) (Coco et al. (2001) *Nature Biotech.* 19:354), site-directed mutagenesis (Zoller et al. (1987) *Nucl Acids Res* 10:6487-6504), cassette mutagenesis (Reidhaar-Olson (1991) *Methods Enzymol.* 208:564-586) and incorporation of degenerate oligonucleotides (Griffiths et al. (1994) *EMBO J* 13: 3245).

In one example of iterative selection, the methods described herein are used to first identify a protein ligand from a display library that binds a ET2 with at least a minimal binding specificity for a target or a minimal activity, e.g., an equilibrium dissociation constant for binding of less than 1 nM, 10 nM, or 100 nM. The nucleic acid sequence encoding the initial identified protein ligands are used as a template nucleic acid for the introduction of variations, e.g., to identify a second protein ligand that has enhanced properties (e.g., binding affinity, kinetics, or stability) relative to the initial protein ligand.

Off-Rate Selection. Since a slow dissociation rate can be predictive of high affinity, particularly with respect to interactions between polypeptides and their targets, the methods described herein can be used to isolate ligands with a desired kinetic dissociation rate (i.e. reduced) for a binding interaction to a target.

To select for slow dissociating ligands from a display library, the library is contacted to an immobilized target. The immobilized target is then washed with a first solution that removes non-specifically or weakly bound biomolecules. Then the bound ligands are eluted with a second solution that includes a saturating amount of free target, i.e., replicates of the target that are not attached to the particle. The free target binds to biomolecules that dissociate from the target. Rebinding is effectively prevented by the saturating amount of free target relative to the much lower concentration of immobilized target.

The second solution can have solution conditions that are substantially physiological or that are stringent. Typically, the solution conditions of the second solution are identical to the solution conditions of the first solution. Fractions of the second solution are collected in temporal order to distinguish early from late fractions. Later fractions include biomolecules that dissociate at a slower rate from the target than biomolecules in the early fractions.

Further, it is also possible to recover display library members that remain bound to the target even after extended incubation. These can either be dissociated using chaotropic conditions or can be amplified while attached to the target. For example, phage bound to the target can be contacted to bacterial cells.

Selecting or Screening for Specificity. The display library screening methods described herein can include a selection or screening process that discards display library members that bind to a non-target molecule. Examples of non-target molecules include, e.g., the Fc domain of the anti-ET2 antibody.

In one implementation, a so-called "negative selection" step is used to discriminate between the target and related non-target molecule and a related, but distinct non-target molecules. The display library or a pool thereof is contacted to the non-target molecule. Members of the sample that do not bind the non-target are collected and used in subsequent selections for binding to the target molecule or even for subsequent negative selections. The negative selection step can be prior to or after selecting library members that bind to the target molecule.

In another implementation, a screening step is used. After display library members are isolated for binding to the target molecule, each isolated library member is tested for its ability to bind to a non-target molecule (e.g., a non-target listed above). For example, a high-throughput ELISA screen can be used to obtain this data. The ELISA screen can also be used to obtain quantitative data for binding of each library member to the target. The non-target and target binding data are compared (e.g., using a computer and software) to identify library members that specifically bind to the target.

Other Expression Libraries

Other types of collections of proteins (e.g., expression libraries) can be used to identify proteins with a particular property (e.g., ability to bind ET2 and/or ability to inhibit ET2), including, e.g., protein arrays of antibodies (see, e.g., De Wildt et al. (2000) *Nat. Biotechnol.* 18:989-994), lambda gt11 libraries, two-hybrid libraries and so forth.

Protein Arrays. Different proteins can be immobilized on a solid support, for example, on a bead or an array. For a protein array, each of the proteins is immobilized at a unique address on a support. Typically, the address is a two-dimensional address.

In some implementations, cells or phage that express the protein can be grown directly on a filter that is used as the array. In other implementations, recombinant protein production is used to produce at least partially purified samples of the protein. The partially purified or pure samples are disposed on the array.

Methods of producing protein arrays are described, e.g., in De Wildt et al. (2000) *Nat. Biotechnol.* 18:989-994; Lueking et al. (1999) *Anal. Biochem.* 270:103-111; Ge (2000) *Nucleic Acids Res.* 28, e3, I-VII; MacBeath and Schreiber (2000) *Science* 289:1760-1763; WO 01/40803 and WO 99/51773A1. Proteins for the array can be spotted at high speed, e.g., using commercially available robotic apparati, e.g., from Genetic MicroSystems or BioRobotics. The array substrate can be, for example, nitrocellulose, plastic, glass, e.g., surface-modified glass. For example, the array can be an array of antibodies, e.g., as described in De Wildt, supra.

Diversity

Display libraries include variation at one or more positions in the displayed polypeptide. The variation at a given position can be synthetic or natural. For some libraries, both synthetic and natural diversity are included.

Synthetic Diversity. Libraries can include regions of diverse nucleic acid sequence that originate from artificially synthesized sequences. Typically, these are formed from degenerate oligonucleotide populations that include a distribution of nucleotides at each given position. The inclusion of a given sequence is random with respect to the distribution. One example of a degenerate source of synthetic diversity is an oligonucleotide that includes NNN wherein N is any of the four nucleotides in equal proportion.

Synthetic diversity can also be more constrained, e.g., to limit the number of codons in a nucleic acid sequence at a given trinucleotide to a distribution that is smaller than NNN. For example, such a distribution can be constructed using less than four nucleotides at some positions of the codon. In addition, trinucleotide addition technology can be used to further constrain the distribution.

So-called "trinucleotide addition technology" is described, e.g., in Wells et al. (1985) *Gene* 34:315-323, U.S. Pat. Nos. 4,760,025 and 5,869,644. Oligonucleotides are synthesized on a solid phase support, one codon (i.e., trinucleotide) at a time. The support includes many functional groups for synthesis such that many oligonucleotides are synthesized in parallel. The support is first exposed to a solution containing a mixture of the set of codons for the first position. The unit is protected so additional units are not added. The solution containing the first mixture is washed away and the solid support is deprotected so a second mixture containing a set of codons for a second position can be added to the attached first unit. The process is iterated to sequentially assemble multiple codons. Trinucleotide addition technology enables the synthesis of a nucleic acid that at a given position can encode a number of amino acids. The frequency of these amino acids can be regulated by the proportion of codons in the mixture. Further the choice of amino acids at the given position is not restricted to quadrants of the codon table as is the case if mixtures of single nucleotides are added during the synthesis.

Natural Diversity. Libraries can include regions of diverse nucleic acid sequence that originate (or are synthesized based on) from different naturally-occurring sequences. An example of natural diversity that can be included in a display library is the sequence diversity present in immune cells (see also below). Nucleic acids are prepared from these immune cells and are manipulated into a format for polypeptide display. Another example of naturally occurring diversity is the diversity of sequences among different species of organisms. For example, diverse nucleic acid sequences can be amplified from environmental samples, such as soil, and used to construct a display library.

Antibody Display Libraries

In one embodiment, the display library presents a diverse pool of polypeptides, each of which includes an immunoglobulin domain, e.g., an immunoglobulin variable domain. Display libraries are particularly useful, for example for identifying human or "humanized" antibodies that recognize human antigens. Such antibodies can be used as therapeutics to treat human disorders such as cancer. Since the constant and framework regions of the antibody are human, these therapeutic antibodies may avoid themselves being recognized and targeted as antigens. The constant regions may also be optimized to recruit effector functions of the human immune system. The in vitro display selection process surmounts the inability of a normal human immune system to generate antibodies against self-antigens. Other types of antibody expression libraries can be used, including, e.g., protein arrays of antibodies (see, e.g., De Wildt et al. (2000) *Nat. Biotechnol.* 18:989-994), lambda gt11 libraries, and so forth.

A typical antibody display library displays a polypeptide that includes a VH domain and a VL domain. An "immunoglobulin domain" refers to a domain from the variable or constant domain of immunoglobulin molecules. Immunoglobulin domains typically contain two β-sheets formed of about seven β-strands, and a conserved disulphide bond (see, e.g., A. F. Williams and A. N. Barclay 1988 *Ann. Rev Immunol.* 6:381-405). The display library can display the antibody as a Fab fragment (e.g., using two polypeptide chains) or a single chain Fv (e.g., using a single polypeptide chain). Other formats can also be used.

As in the case of the Fab and other formats, the displayed antibody can include one or more constant regions as part of a light and/or heavy chain. In one embodiment, each chain includes one constant region, e.g., as in the case of a Fab. In other embodiments, additional constant regions are displayed.

Antibody libraries can be constructed by a number of processes (see, e.g., de Haard et al. (1999) *J. Biol. Chem* 274:18218-30; Hoogenboom et al. (1998) *Immunotechnology* 4:1-20. and Hoogenboom et al. (2000) *Immunol Today* 21:371-8. Further, elements of each process can be combined with those of other processes. The processes can be used such that variation is introduced into a single immunoglobulin domain (e.g., VH or VL) or into multiple immunoglobulin domains (e.g., VH and VL). The variation can be introduced into an immunoglobulin variable domain, e.g., in the region of one or more of CDR1, CDR2, CDR3, FR1, FR2, FR3, and FR4, referring to such regions of either and both of heavy and light chain variable domains. In one embodiment, variation is introduced into all three CDRs of a given variable domain. In another preferred embodiment, the variation is introduced into CDR1 and CDR2, e.g., of a heavy chain variable domain. Any combination is feasible. In one process, antibody libraries are constructed by inserting diverse oligonucleotides that encode CDRs into the corresponding regions of the nucleic acid. The oligonucleotides can be synthesized using monomeric nucleotides or trinucleotides. For example, Knappik et al. (2000) *J. Mol. Biol.* 296:57-86 describe a method for constructing CDR encoding oligonucleotides using trinucleotide synthesis and a template with engineered restriction sites for accepting the oligonucleotides.

In another process, an animal, e.g., a rodent, is immunized with the ET2. The animal is optionally boosted with the antigen to further stimulate the response. Then spleen cells are isolated from the animal, and nucleic acid encoding VH and/or VL domains is amplified and cloned for expression in the display library.

In yet another process, antibody libraries are constructed from nucleic acid amplified from naïve germline immunoglobulin genes. The amplified nucleic acid includes nucleic acid encoding the VH and/or VL domain. Sources of immunoglobulin-encoding nucleic acids are described below. Amplification can include PCR, e.g., with primers that anneal to the conserved constant region, or another amplification method.

Nucleic acid encoding immunoglobulin domains can be obtained from the immune cells of, e.g., a human, a primate, mouse, rabbit, camel, or rodent. In one example, the cells are selected for a particular property. B cells at various stages of maturity can be selected. In another example, the B cells are naïve.

In one embodiment, fluorescent-activated cell sorting (FACS) is used to sort B cells that express surface-bound IgM, IgD, or IgG molecules. Further, B cells expressing different isotypes of IgG can be isolated. In another preferred embodiment, the B or T cell is cultured in vitro. The cells can be stimulated in vitro, e.g., by culturing with feeder cells or by adding mitogens or other modulatory reagents, such as antibodies to CD40, CD40 ligand or CD20, phorbol myristate acetate, bacterial lipopolysaccharide, concanavalin A, phytohemagglutinin or pokeweed mitogen.

In still another embodiment, the cells are isolated from a subject that has an immunological disorder, e.g., systemic lupus erythematosus (SLE), rheumatoid arthritis, vasculitis, Sjogren syndrome, systemic sclerosis, or anti-phospholipid syndrome. The subject can be a human, or an animal, e.g., an animal model for the human disease, or an animal having an analogous disorder. In yet another embodiment, the cells are isolated from a transgenic non-human animal that includes a human immunoglobulin locus.

In one preferred embodiment, the cells have activated a program of somatic hypermutation. Cells can be stimulated to undergo somatic mutagenesis of immunoglobulin genes, for example, by treatment with anti-immunoglobulin, anti-CD40, and anti-CD38 antibodies (see, e.g., Bergthorsdottir et al. (2001) *J Immunol.* 166:2228). In another embodiment, the cells are naïve.

The nucleic acid encoding an immunoglobulin variable domain can be isolated from a natural repertoire by the following exemplary method. First, RNA is isolated from the immune cell. Full length (i.e., capped) mRNAs are separated (e.g. by degrading uncapped RNAs with calf intestinal phosphatase). The cap is then removed with tobacco acid pyrophosphatase and reverse transcription is used to produce the cDNAs.

The reverse transcription of the first (antisense) strand can be done in any manner with any suitable primer. See, e.g., de Haard et al. (1999) *J. Biol. Chem* 274:18218-30. The primer binding region can be constant among different immunoglobulins, e.g., in order to reverse transcribe different isotypes of immunoglobulin. The primer binding region can also be specific to a particular isotype of immunoglobulin. Typically, the primer is specific for a region that is 3' to a sequence encoding at least one CDR. In another embodiment, poly-dT primers may be used (and may be preferred for the heavy-chain genes).

A synthetic sequence can be ligated to the 3' end of the reverse transcribed strand. The synthetic sequence can be used as a primer binding site for binding of the forward primer during PCR amplification after reverse transcription. The use of the synthetic sequence can obviate the need to use a pool of different forward primers to fully capture the available diversity.

The variable domain-encoding gene is then amplified, e.g., using one or more rounds. If multiple rounds are used, nested primers can be used for increased fidelity. The amplified nucleic acid is then cloned into a display library vector.

Any method for amplifying nucleic acid sequences may be used for amplification. Methods that maximize, and do not bias, diversity are preferred. A variety of techniques can be used for nucleic acid amplification. The polymerase chain reaction (PCR; U.S. Pat. Nos. 4,683,195 and 4,683,202, Saiki, et al. (1985) *Science* 230, 1350-1354) utilizes cycles of varying temperature to drive rounds of nucleic acid synthesis. Transcription-based methods utilize RNA synthesis by RNA polymerases to amplify nucleic acid (U.S. Pat. No. 6,066,457; U.S. Pat. No. 6,132,997; U.S. Pat. No. 5,716,785; Sarkar et. al., *Science* (1989) 244:331-34; Stofler et al., *Science* (1988) 239: 491). NASBA (U.S. Pat. Nos. 5,130,238; 5,409,818; and 5,554,517) utilizes cycles of transcription, reverse-transcription, and RnaseH-based degradation to amplify a DNA sample. Still other amplification methods include rolling circle amplification (RCA; U.S. Pat. Nos. 5,854,033 and 6,143,495) and strand displacement amplification (SDA; U.S. Pat. Nos. 5,455,166 and 5,624,825).

Secondary Screening Methods

After selecting candidate display library members that bind to a target, each candidate display library member can be further analyzed, e.g., to further characterize its binding properties for the target. Each candidate display library member can be subjected to one or more secondary screening assays. The assay can be for a binding property, a catalytic property, an inhibitory property, a physiological property (e.g., cytotoxicity, renal clearance, immunogenicity), a structural property (e.g., stability, conformation, oligomerization state) or another functional property. The same assay can be used repeatedly, but with varying conditions, e.g., to determine pH, ionic, or thermal sensitivities.

As appropriate, the assays can use the display library member directly, a recombinant polypeptide produced from the nucleic acid encoding a displayed polypeptide, or a synthetic peptide synthesized based on the sequence of a displayed peptide. Exemplary assays for binding properties include the following.

ELISA. Polypeptides encoded by a display library can also be screened for a binding property using an ELISA assay. For example, each polypeptide is contacted to a microtitre plate whose bottom surface has been coated with the target, e.g., a limiting amount of the target. The plate is washed with buffer to remove non-specifically bound polypeptides. Then the amount of the polypeptide bound to the plate is determined by probing the plate with an antibody that can recognize the polypeptide, e.g., a tag or constant portion of the polypeptide. The antibody is linked to an enzyme such as alkaline phosphatase, which produces a colorimetric product when appropriate substrates are provided. The polypeptide can be purified from cells or assayed in a display library format, e.g., as a fusion to a filamentous bacteriophage coat. In another version of the ELISA assay, each polypeptide of a diversity strand library is used to coat a different well of a microtitre plate. The ELISA then proceeds using a constant target molecule to query each well.

Homogeneous Binding Assays. The binding interaction of candidate polypeptide with a target can be analyzed using a homogenous assay, i.e., after all components of the assay are added, additional fluid manipulations are not required. For example, fluorescence resonance energy transfer (FRET) can be used as a homogenous assay (see, for example, Lakowicz et al., U.S. Pat. No. 5,631,169; Stavrianopoulos, et al., U.S. Pat. No. 4,868,103). A fluorophore label on the first molecule (e.g., the molecule identified in the fraction) is selected such that its emitted fluorescent energy can be absorbed by a fluorescent label on a second molecule (e.g., the target) if the second molecule is in proximity to the first molecule. The fluorescent label on the second molecule fluoresces when it absorbs to the transferred energy. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. A binding event that is configured for monitoring by FRET can be conveniently measured through standard fluorometric detection means well known in the art (e.g., using a fluorimeter). By titrating the amount of the first or second binding molecule, a binding curve can be generated to estimate the equilibrium binding constant.

Another example of a homogenous assay is Alpha Screen (Packard Bioscience, Meriden Conn.). Alpha Screen uses two labeled beads. One bead generates singlet oxygen when excited by a laser. The other bead generates a light signal when singlet oxygen diffuses from the first bead and collides with it. The signal is only generated when the two beads are in proximity. One bead can be attached to the display library member, the other to the target. Signals are measured to determine the extent of binding.

The homogenous assays can be performed while the candidate polypeptide is attached to the display library vehicle, e.g., a bacteriophage.

Surface Plasmon Resonance (SPR). The binding interaction of a molecule isolated from a display library and a target can be analyzed using SPR. SPR or Biomolecular Interaction Analysis (BIA) detects biospecific interactions in real time, without labeling any of the interactants. Changes in the mass at the binding surface (indicative of a binding event) of the BIA chip result in alterations of the refractive index of light near the surface (the optical phenomenon of surface plasmon resonance (SPR)). The changes in the refractivity generate a detectable signal, which are measured as an indication of real-time reactions between biological molecules. Methods for using SPR are described, for example, in U.S. Pat. No. 5,641,640; Raether (1988) *Surface Plasmons* Springer Verlag; Sjolander and Urbaniczky (1991) *Anal. Chem.* 63:2338-2345; Szabo et al. (1995) *Curr. Opin. Struct. Biol.* 5:699-705 and on-line resources provide by BIAcore International AB (Uppsala, Sweden).

Information from SPR can be used to provide an accurate and quantitative measure of the equilibrium dissociation constant ($K_d$), and kinetic parameters, including $K_{on}$ and $K_{off}$, for the binding of a biomolecule to a target. Such data can be used to compare different biomolecules. For example, proteins encoded by nucleic acid selected from a library of diversity strands can be compared to identify individuals that have high affinity for the target or that have a slow $K_{off}$. This information can also be used to develop structure-activity relationships (SAR). For example, the kinetic and equilibrium binding parameters of matured versions of a parent protein can be compared to the parameters of the parent protein. Variant amino acids at given positions can be identified that correlate with particular binding parameters, e.g., high affinity and slow $K_{off}$. This information can be combined with structural modeling (e.g., using homology modeling, energy minimization, or structure determination by x-ray crystallography or NMR). As a result, an understanding of the physical interaction between the protein and its target can be formulated and used to guide other design processes.

Protein Arrays. Polypeptides identified from the display library can be immobilized on a solid support, for example, on a bead or an array. For a protein array, each of the polypeptides is immobilized at a unique address on a support. Typically, the address is a two-dimensional address. Protein arrays are described below (see, e.g., Diagnostics).

Cellular Assays. A library of candidate polypeptides (e.g., previously identified by a display library or otherwise) can be screened by transforming the library into a host cell. For example, the library can include vector nucleic acid sequences that include segments that encode the polypeptides and that direct expression, e.g., such that the polypeptides are produced within the cell, secreted from the cell, or attached to the cell surface. The cells can be screened for polypeptides that bind to the ET2, e.g., as detected by a change in a cellular phenotype or a cell-mediated activity. For example, in the case of an antibody that binds to the ET2, the activity may be cell or complement-mediated cytotoxicity.

Automation

In one embodiment, at least some aspects of the screening method are automated. Automated methods can be used for a high throughput screen, e.g., to detect interactions with ET2 such as binding interactions or enzymatic interaction (e.g., inhibition of ET2 activity). For example, clones isolated from a primary screen and encoding candidate ligands are stored in an arrayed format (e.g., microtitre plates). A robotic device can be automatically controlled to set up assays for each of the candidate ligands in a variety of formats, e.g., ELISA (using purified ligands or phage displaying the ligand), enzyme assays, cell based assays, and so forth. Enzymatic activity, for example, can be detected by any of a variety of methods, including spectroscopically, colorimetircally, using mass spectroscopy, and so forth.

Data indicating the performance of each clone for a particular assay, e.g., a binding assay, an activity assay, or a cell-based assay, can be stored in database. Software can be used to access the database and select clones that meet particular criteria, e.g., exceed a threshold for an assay. The software can then direct a robotic arm to pick the selected clones from the stored array, prepare nucleic acid encoding the ligand, prepare the ligand itself, and/or produce and screen secondary libraries whose members are mutated variants of the initially picked ligand.

Various robotic devices that can be employed in the automation process include multi-well plate conveyance systems, magnetic bead particle processors, liquid handling units, colony picking units. These devices can be built on custom specifications or purchased from commercial sources, such as Autogen (Framingham Mass.), Beckman Coulter (USA), Biorobotics (Woburn Mass.), Genetix (New Milton, Hampshire UK), Hamilton (Reno Nev.), Hudson (Springfield N.J.), Labsystems (Helsinki, Finland), Perkin Elmer Lifesciences (Wellseley Mass.), Packard Bioscience (Meriden Conn.), and Tecan (Mannedorf, Switzerland).

Methods for Obtaining ET2-Binding Antibodies

In addition to the use of display libraries, other methods can be used to obtain a ET2-binding antibody. For example, the ET2 protein or a region thereof can be used as an antigen in a non-human animal, e.g., a rodent.

In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific Mabs derived from the genes with the desired specificity may be produced and selected. See, e.g., XENOMOUSE™, Green et al. Nature Genetics 7:13-21 (1994), U.S. 2003-0070185, WO 96/34096, published Oct. 31, 1996, and PCT Application No. PCT/US96/05928, filed Apr. 29, 1996.

In another embodiment, a monoclonal antibody is obtained from the non-human animal, and then modified, e.g., humanized or deimmunized. Winter describes a CDR-grafting method that may be used to prepare the humanized antibodies of the present invention (UK Patent Application GB 2188638A, filed on Mar. 26, 1987; U.S. Pat. No. 5,225,539. All of the CDRs of a particular human antibody may be replaced with at least a portion of a non-human CDR or only some of the CDRs may be replaced with non-human CDRs. It is only necessary to replace the number of CDRs required for binding of the humanized antibody to a predetermined antigen.

Humanized antibodies can be generated by replacing sequences of the Fv variable region that are not directly involved in antigen binding with equivalent sequences from human Fv variable regions. General methods for generating humanized antibodies are provided by Morrison, S. L., 1985, *Science* 229:1202-1207, by Oi et al., 1986, *BioTechniques* 4:214, and by Queen et al. U.S. Pat. No. 5,585,089, U.S. Pat. No. 5,693,761 and U.S. Pat. No. 5,693,762. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a predetermined target, as described above. The recombinant DNA encoding the humanized antibody, or fragment thereof, can then be cloned into an appropriate expression vector.

A ET2-binding antibody may also be modified by specific deletion of human T cell epitopes or "deimmunization" by the methods disclosed in WO 98/52976 and WO 00/34317, the contents of which are specifically incorporated by reference herein. Briefly, the heavy and light chain variable regions of an antibody can be analyzed for peptides that bind to MHC Class II; these peptides represent potential T-cell epitopes (as defined in WO 98/52976 and WO 00/34317). For detection of potential T-cell epitopes, a computer modeling approach termed "peptide threading" can be applied, and in addition a database of human MHC class II binding peptides can be searched for motifs present in the $V_H$ and $V_L$ sequences, as described in WO 98/52976 and WO 00/34317. These motifs bind to any of the 18 major MHC class II DR allotypes, and thus constitute potential T cell epitopes. Potential T-cell epitopes detected can be eliminated by substituting small numbers of amino acid residues in the variable regions, or preferably, by single amino acid substitutions. As far as possible conservative substitutions are made, often but not exclusively, an amino acid common at this position in human germline antibody sequences may be used. Human germline sequences are disclosed in Tomlinson, I. A. et al. (1992) *J. Mol. Biol.* 227:776-798; Cook, G. P. et al. (1995) *Immunol. Today Vol.* 16 (5): 237-242; Chothia, D. et al. (1992) *J. Mol. Bio.* 227:799-817. The V BASE directory provides a comprehensive directory of human immunoglobulin variable region sequences (compiled by Tomlinson, I. A. et al. MRC Centre for Protein Engineering, Cambridge, UK). After the deimmunizing changes are identified, nucleic acids encoding VH and VL can be constructed by mutagenesis or other synthetic methods (e.g., de novo synthesis, cassette replacement, and so forth). Mutagenized variable sequence can, optionally, be fused to a human constant region, e.g., human IgG1 or κ constant regions.

In some cases a potential T cell epitope will include residues which are known or predicted to be important for antibody function. For example, potential T cell epitopes are usually biased towards the CDRs. In addition, potential T cell epitopes can occur in framework residues important for antibody structure and binding. Changes to eliminate these potential epitopes will in some cases require more scrutiny, e.g., by making and testing chains with and without the change. Where possible, potential T cell epitopes that overlap the CDRs were eliminated by substitutions outside the CDRs. In some cases, an alteration within a CDR is the only option, and thus variants with and without this substitution should be tested. In other cases, the substitution required to remove a potential T cell epitope is at a residue position within the framework that might be critical for antibody binding. In these cases, variants with and without this substitution should be tested. Thus, in some cases several variant deimmunized heavy and light chain variable regions were designed and various heavy/light chain combinations tested in order to identify the optimal deimmunized antibody. The choice of the final deimmunized antibody can then be made by considering the binding affinity of the different variants in conjunction with the extent of deimmunization, i.e., the number of potential T cell epitopes remaining in the variable region. Deimmunization can be used to modify any antibody, e.g., an antibody that includes a non-human sequence, e.g., a synthetic antibody, a murine antibody other non-human monoclonal antibody, or an antibody isolated from a display library.

Germlining Antibodies

It is possible to modify an antibody that binds ET2, e.g., an antibody described herein, in order to make the variable regions of the antibody more similar to one or more germline sequences. For example, an antibody can include one, two, three or more amino acid substitutions, e.g., in a framework or CDR region, to make it more similar to a reference germline sequence. One exemplary germlining method can include: identifying one or more germline sequences that are similar (e.g., most similar in a particular database) to the sequence of the isolated antibody. Then mutations (at the amino acid level) can be made in the isolated antibody, either incrementally, in combination, or both. For example, a nucleic acid library that includes sequences encoding some or all possible germline mutations is made. The mutated antibodies are then evaluated, e.g., to identify an antibody that has one or more additional germline residues relative to the isolated antibody and that is still useful (e.g., has a functional activity). In one embodiment, as many germline residues are introduced into an isolated antibody as possible.

In one embodiment, mutagenesis is used to substitute or insert one or more germline residues into a CDR region. For example, the germline CDR residue can be from a germline sequence that is similar (e.g., most similar) to the variable region being modified. After mutagenesis, activity (e.g., binding or other functional activity) of the antibody can be evaluated to determine if the germline residue or residues are tolerated. Similar mutagenesis can be performed in the framework regions.

Selecting a germline sequence can be performed in different ways. For example, a germline sequence can be selected if it meets a predetermined criteria for selectivity or similarity, e.g., at least a certain percentage identity, e.g., at least 75, 80, 85, 90, 91, 92, 93, 94, 95, 96, 97, 98, 99, or 99.5% identity. The selection can be performed using at least 2, 3, 5, or 10 germline sequences. In the case of CDR1 and CDR2, identifying a similar germline sequence can include selecting one such sequence. In the case of CDR3, identifying a similar germline sequence can include selecting one such sequence, but may including using two germline sequences that separately contribute to the amino-terminal portion and the carboxy-terminal portion. In other implementations more than one or two germline sequences are used, e.g., to form a consensus sequence.

In one embodiment, with respect to a particular reference variable domain sequence, e.g., a sequence described herein, a related variable domain sequence has at at least 30, 40, 50, 60, 70, 80, 90, 95 or 100% of the CDR amino acid positions that are not identical to residues in the reference CDR sequences, residues that are identical to residues at corresponding positions in a human germline sequence (i.e., an amino acid sequence encoded by a human germline nucleic acid).

In one embodiment, with respect to a particular reference variable domain sequence, e.g., a sequence described herein, a related variable domain sequence has at at least 30, 50, 60, 70, 80, 90 or 100% of the FR regions are identical to FR sequence from a human germline sequence, e.g., a germline sequence related to the reference variable domain sequence.

Accordingly, it is possible to isolate an antibody which has similar activity to a given antibody of interest, but is more similar to one or more germline sequences, particularly one or more human germline sequences. For example, an antibody can be at least 90, 91, 92, 93, 94, 95, 96, 97, 98, 99, 99.5% identical to a germline sequence in a region outside the CDRs (e.g., framework regions). Further an antibody can include at least 1, 2, 3, 4, or 5 germline residues in a CDR region, the germline residue being from a germline sequence of similar (e.g., most similar) to the variable region being modified. Germline sequences of primary interest are human germline sequences. The activity of the antibody (e.g., the binding activity) can be within a factor or 100, 10, 5, 2, 0.5, 0.1, and 0.001 of the original antibody.

Exemplary germline reference sequences for Vkappa include: O12/O2, O18/O8, A20, A30, L14, L1, L15, L4/18a, L5/L19, L8, L23, L9, L24, L11, L12, O11/O1, A17, A1, A18, A2, A19/A3, A23, A27, A11, L2/L16, L6, L20, L25, B3, B2, A26/A10, and A14. See, e.g., Tomlinson et al. (1995) EMBO J. 14(18):4628-3.

A germline reference sequence for the HC variable domain can be based on a sequence that has particular canonical structures, e.g., 1-3 structures in the H1 and H2 hypervariable loops. The canonical structures of hypervariable loops of an immunoglobulin variable domain can be inferred from its sequence, as described in Chothia et al. (1992) *J. Mol. Biol.* 227:799-817; Tomlinson et al. (1992) *J. Mol. Biol.* 227:776-798); and Tomlinson et al. (1995) *EMBO J.* 14(18):4628-38. Exemplary sequences with a 1-3 structure include: DP-1, DP-8, DP-12, DP-2, DP-25, DP-15, DP-7, DP-4, DP-31, DP-32, DP-33, DP-35, DP-40, 7-2, hv3005, hv3005f3, DP-46, DP-47, DP-58, DP-49, DP-50, DP-51, DP-53, and DP-54.

Ligand Production

Standard recombinant nucleic acid methods can be used to express a protein ligand that binds to ET2. Generally, a nucleic acid sequence encoding the protein ligand is cloned into a nucleic acid expression vector. Of course, if the protein includes multiple polypeptide chains, each chain must be cloned into an expression vector, e.g., the same or different vectors, that are expressed in the same or different cells.

Antibody Production. Some antibodies, e.g., Fabs, can be produced in bacterial cells, e.g., *E. coli* cells. For example, if the Fab is encoded by sequences in a phage display vector that includes a suppressible stop codon between the display entity and a bacteriophage protein (or fragment thereof), the vector nucleic acid can be transferred into a bacterial cell that cannot suppress a stop codon. In this case, the Fab is not fused to the gene III protein and is secreted into the periplasm and/or media.

Antibodies can also be produced in eukaryotic cells. In one embodiment, the antibodies (e.g., scFv's) are expressed in a yeast cell such as *Pichia* (see, e.g., Powers et al. (2001) *J Immunol Methods.* 251:123-35), *Hanseula*, or *Saccharomyces.*

In one preferred embodiment, antibodies are produced in mammalian cells. Preferred mammalian host cells for expressing the clone antibodies or antigen-binding fragments thereof include Chinese Hamster Ovary (CHO cells) (including dhfr-CHO cells, described in Urlaub and Chasin (1980) *Proc. Natl. Acad. Sci. USA* 77:4216-4220, used with a DHFR selectable marker, e.g., as described in Kaufman and Sharp (1982) *Mol. Biol.* 159:601-621), lymphocytic cell lines, e.g., NS0 myeloma cells and SP2 cells, COS cells, and a cell from a transgenic animal, e.g., a transgenic mammal. For example, the cell is a mammary epithelial cell.

In addition to the nucleic acid sequence encoding the diversified immunoglobulin domain, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in $dhfr^-$ host cells with methotrexate selection/amplification) and the neo gene (for G418 selection).

In an exemplary system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. For example, some antibodies can be isolated by affinity chromatography with a Protein A or Protein G coupled matrix.

For antibodies that include an Fc domain, the antibody production system preferably synthesizes antibodies in which the Fc region is glycosylated. For example, the Fc domain of IgG molecules is glycosylated at asparagine 297 in the CH2 domain. This asparagine is the site for modification with biantennary-type oligosaccharides. It has been demonstrated that this glycosylation is required for effector functions mediated by Fcγ receptors and complement C1q (Burton and Woof (1992) *Adv. Immunol.* 51:1-84; Jefferis et al. (1998) *Immunol. Rev.* 163:59-76). In one embodiment, the Fc domain is produced in a mammalian expression system that appropriately glycosylates the residue corresponding to asparagine 297. The Fc domain can also include other eukaryotic post-translational modifications.

Antibodies can also be produced by a transgenic animal. For example, U.S. Pat. No. 5,849,992 describes a method of expressing an antibody in the mammary gland of a transgenic mammal. A transgene is constructed that includes a milk-specific promoter and nucleic acids encoding the antibody of interest and a signal sequence for secretion. The milk produced by females of such transgenic mammals includes, secreted-therein, the antibody of interest. The antibody can be purified from the milk, or for some applications, used directly.

Generation of transgenic animals are well known in the art. One method for producing a transgenic mouse is as follows. Briefly, a targeting construct that encodes the antibody is microinjected into the male pronucleus of fertilized oocytes. The oocytes are injected into the uterus of a pseudopregnant foster mother for the development into viable pups. Some offspring will have incorproted the transgene.

Assay Systems for ET2 Ligands

Potential ET2 ligands can be further characterized in assays that measure their modulatory activity toward ET2 or fragments thereof in vitro or in vivo. For example, ET2 can be combined with a substrate under assay conditions permitting reaction of the ET2 with the substrate. The assay is performed in the absence of the potential ET2 ligand, and in the presence of increasing concentrations of the potential ET2 ligand. The concentration of ligand at which 50% of the ET2 activity is inhibited by the test compound is the $IC_{50}$ value (Inhibitory Concentration) or $EC_{50}$ (Effective Concentration) value for that compound. Within a series or group of test ligands, those having lower $IC_{50}$ or $EC_{50}$ values are considered more potent inhibitors of ET2 than those compounds having higher $IC_{50}$ or $EC_{50}$ values. Preferred ligands have an $IC_{50}$ value of 100 nM or less as measured in an in vitro assay for inhibition of ET2 activity.

The ligands can also be evaluated for selectivity toward ET2. For example, a potential ET2 ligand can be assayed for its potency toward ET2 and a panel of serine proteases and other enzymes and an $IC_{50}$ value or $EC_{50}$ value can be determined for each enzymatic target. In one embodiment, a compound that demonstrates a low $IC_{50}$ value or $EC_{50}$ value for the ET2, and a higher $IC_{50}$ value or $EC_{50}$ value for other enzymes within the test panel (e.g., urokinase, tissue plasminogen activator, thrombin, Factor Xa) is considered to be selective toward ET2. In one embodiment, a compound that demonstrates a low $IC_{50}$ value or $EC_{50}$ value for the ET2, and a higher $IC_{50}$ value or $EC_{50}$ value for ET1 than ET2 is considered to be selective toward ET2.

Potential ET2 ligands can also be evaluated for their activity in vivo. For example, to evaluate the activity of a ligand to reduce tumor growth through inhibition of endotheliase, the procedures described by Jankun et al., *Canc. Res.,* 57:559-563 (1997) to evaluate PAI-1 can be employed. Briefly, the ATCC cell lines DU145 and LnCaP are injected into SCID mice. After tumors are established, the mice are administered the test ligand. Tumor volume measurements are taken twice a week for about five weeks. A ligand can be deemed active in this assay if an animal to which the ligand was administered exhibited decreased tumor volume, as compared to animals receiving appropriate control compounds (e.g., non-specific antibody molecules).

To evaluate the ability of a ligand to reduce the occurrence of, or inhibit, metastasis, the procedures described by Kobayashi et al., *Int. J. Canc.,* 57:727-733d (1994) can be employed. Briefly, a murine xenograft selected for high lung colonization potential in injected into C57B1/6 mice i.v. (experimental metastasis) or s.c. into the abdominal wall (spontaneous metastasis). Various concentrations of the compound to be tested can be admixed with the tumor cells in Matrigel prior to injection. Daily i.p. injections of the test compound are made either on days 1-6 or days 7-13 after tumor inoculation. The animals are sacrificed about three or four weeks after tumor inoculation, and the lung tumor colonies are counted. Evaluation of the resulting data permits a determination as to efficacy of the test compound, optimal dosing and route of administration.

The activity of the ligands toward decreasing tumor volume and metastasis can be evaluated in model described in Rabbani et al., *Int. J. Cancer* 63: 840-845 (1995). See also Xing et al., *Canc. Res.,* 57: 3585-3593 (1997). There, Mat LyLu tumor cells were injected into the flank of Copenhagen rats. The animals were implanted with osmotic minipumps to continuously administer various doses of test compound for up to three weeks. The tumor mass and volume of experimental and control animals were evaluated during the experiment, as were metastatic growths. Evaluation of the resulting data permits a determination as to efficacy of the test compound, optimal dosing, and route of administration. Some of these authors described a related protocol in Xing et al., *Canc. Res.,* 57: 3585-3593 (1997).

To evaluate the inhibitory activity of a ligand toward neovascularization, a rabbit cornea neovascularization model can be employed. See, e.g., Avery et al., *Arch. Ophthalmol.,* 108: 1474-1475 (1990). In this model, New Zealand albino rabbits are anesthetized. A central corneal incision is made, forming a radial corneal pocket. A slow release prostaglandin pellet is placed in the pocket to induce neovascularization. The test ligand is administered i. p. for five days, then the animals are sacrificed. The effect of the test ligand is evaluated by review of periodic photographs taken of the limbus, which can be used to calculate the area of neovascular response and, therefore, limbal neovascularization. A decreased area of neovascularization as compared with appropriate controls indicates the test ligand was effective at decreasing or inhibiting neovascularization.

An exemplary angiogenesis model used to evaluate the effect of a test compound in preventing angiogenesis is described by Min et al., *Canc. Res.,* 56: 2428-2433 (1996). In this model, C57BL6 mice receive subcutaneous injections of a Matrigel mixture containing bFGF, as the angiogenesis-inducing agent, with and without the test ligand. After five days, the animals are sacrificed and the Matrigel plugs, in which neovascularization can be visualized, are photographed. An experimental animal receiving Matrigel and an effective dose of test ligand will exhibit less vascularization than a control animal or an experimental animal receiving a less- or non-effective does of ligand.

An in vivo system designed to test compound for their ability to limit the spread of primary tumors is described by Crowley et al., *Proc. Natl. Acad. Sci.,* 90: 5021-5025 (1993). Nude mice are injected with tumor cells (PC3) engineered to express CAT (chloramphenicol acetyltransferase). Compounds to be tested for their ability to decrease tumor size and/or metastases are administered to the animals, and subsequent measurements of tumor size and/or metastatic growths are made. In addition, the level of CAT detected in various organs provides an indication of the ability of the test compound to inhibit metastasis; detection of less CAT in tissues of a treated animal versus a control animal indicates less CAT-expressing cells migrated to that tissue.

In vivo experimental modes designed to evaluate the inhibitory potential of a test serine protease inhibitors, using a tumor cell line F311, are described by Alonso et al., *Breast Canc. Res. Treat.,* 40: 209-223 (1996). This group describes in vivo studies for toxicity determination, tumor growth, invasiveness, spontaneous metastasis, experimental lung metastasis, and an angiogenesis assay.

The CAM model (chick embryo chorioallantoic membrane model), first described by L. Ossowski (*J. Cell. Biol.,* 107: 2437-2445 (1988)), provides another method for evaluating the protease inhibitory activity of a test compound. In the CAM model, tumor cells invade through the chorioallantoic membrane containing CAM with tumor cells in the presence of several serine protease inhibitors results in less or no invasion of the tumor cells through the membrane. Thus, the CAM assay is performed with CAM and tumor cells in the presence and absence of various concentrations of test compound. The invasiveness of tumor cells is measured under such conditions to provide an indication of the compound's inhibitory activity. A compound having inhibitory activity correlates with less tumor invasion.

The CAM model is also used in to assay angiogenesis (i.e., effect on formation of new blood vessels (Brooks et al., *Methods in Molecular Biology,* 129: 257-269 (1999)). According to this model, a filter disc containing an angiogenesis inducer, such as basic fibroblast growth factor (bFDG) is placed onto the CAM. Diffusion of the cytokine into the CAM induces local angiogenesis, which may be measured in several ways such as by counting the number of blood vessel branch points within the CAM directly below the filter disc. The ability of identified compounds to inhibit cytokine-induced angiogenesis can be tested using this model. A test compound can either be added to the filter disc that contains the angiogenesis inducer, be placed directly on the membrane or be administered systemically. The extent of new blood vessel formation in the presence and/or absence of test compound can be compared using this model. The formation of fewer new blood vessels in the presence of a test compound would be indicative of anti-angiogenesis activity.

Endothelial cell proliferation. A candidate ET2-binding ligand can be tested for endothelial proliferation inhibiting activity using a biological activity assay such as the bovine capillary endothelial cell proliferation assay, the chick CAM assay, the mouse corneal assay, and evaluating the effect of the ligand on implanted tumors. The chick CAM assay is described, e.g., by O'Reilly, et al. in "Angiogenic Regulation of Metastatic Growth" Cell, vol. 79 (2), Oct. 21, 1994, pp. 315-328. Briefly, three day old chicken embryos with intact yolks are separated from the egg and placed in a petri dish. After three days of incubation a methylcellulose disc containing the protein to be tested is applied to the CAM of individual embryos. After 48 hours of incubation, the embryos and CAMs are observed to determine whether endothelial growth has been inhibited. The mouse corneal assay involves implanting a growth factor-containing pellet, along with another pellet containing the suspected endothelial growth inhibitor, in the cornea of a mouse and observing the pattern of capillaries that are elaborated in the cornea.

Angiogenesis. Angiogenesis may be assayed, e.g., using various human endothelial cell systems, such as umbilical vein, coronary artery, or dermal cells. Suitable assays include Alamar Blue based assays (available from Biosource International) to measure proliferation; migration assays using fluorescent molecules, such as the use of Becton Dickinson Falcon HTS FluoroBlock cell culture inserts to measure migration of cells through membranes in presence or absence of angiogenesis enhancer or suppressors; and tubule formation assays based on the formation of tubular structures by endothelial cells on MATRIGEL™ (Becton Dickinson).

Cell adhesion. Cell adhesion assays measure adhesion of cells to purified adhesion proteins or adhesion of cells to each other, in presence or absence of candidate ET2 binding ligands. Cell-protein adhesion assays measure the ability of agents to modulate the adhesion of cells to purified proteins. For example, recombinant proteins are produced, diluted to 2.5 g/mL in PBS, and used to coat the wells of a microtiter plate. The wells used for negative control are not coated. Coated wells are then washed, blocked with 1% BSA, and washed again. Compounds are diluted to 2× final test concentration and added to the blocked, coated wells. Cells are then added to the wells, and the unbound cells are washed off. Retained cells are labeled directly on the plate by adding a membrane-permeable fluorescent dye, such as calcein-AM, and the signal is quantified in a fluorescent microplate reader.

Cell-cell adhesion assays can be used to measure the ability of candidate ET2 binding ligands to modulate binding of cells to each other. These assays can use cells that naturally or recombinantly express an adhesion protein of choice. In an exemplary assay, cells expressing the cell adhesion protein are plated in wells of a multiwell plate together with other cells (either more of the same cell type, or another type of cell to which the cells adhere). The cells that can adhere are labeled with a membrane-permeable fluorescent dye, such as BCECF, and allowed to adhere to the monolayers in the presence of candidate ligands. Unbound cells are washed off, and bound cells are detected using a fluorescence plate reader. High-throughput cell adhesion assays have also been described. See, e.g., Falsey J R et al., *Bioconjug Chem.* May-June 2001; 12(3): 346-53.

Tubulogenesis. Tubulogenesis assays can be used to monitor the ability of cultured cells, generally endothelial cells, to form tubular structures on a matrix substrate, which generally simulates the environment of the extracellular matrix. Exemplary substrates include MATRIGEL™ (Becton Dickinson), an extract of basement membrane proteins containing laminin, collagen IV, and heparin sulfate proteoglycan, which is liquid at 4° C. and forms a solid gel at 37° C. Other suitable matrices comprise extracellular components such as collagen, fibronectin, and/or fibrin. Cells are stimulated with a pro-angiogenic stimulant, and their ability to form tubules is detected by imaging. Tubules can generally be detected after an overnight incubation with stimuli, but longer or shorter time frames may also be used. Tube formation assays are well known in the art (e.g., Jones M K et al., 1999, Nature Medicine 5:1418-1423). These assays have traditionally involved stimulation with serum or with the growth factors FGF or VEGF. In one embodiment, the assay is performed with cells cultured in serum free medium. In one embodiment, the assay is performed in the presence of one or more pro-angiogenic agents, e.g., inflammatory angiogenic factors, such as TNF-α, FGF, VEGF, phorbol myristate acetate (PMA), TNF-alpha, ephrin, etc.

Cell Migration. An exemplary assay for endothelial cell migration is the human microvascular endothelial (HMVEC) migration assay. See, e.g., Tolsma et al. (1993) *J. Cell Biol* 122, 497-511. Migration assays are known in the art (e.g., Paik J H et al., 2001, J Biol Chem 276:11830-11837). In one example, cultured endothelial cells are seeded onto a matrix-coated porous lamina, with pore sizes generally smaller than typical cell size. The lamina is typically a membrane, such as the transwell polycarbonate membrane (Corning Costar Corporation, Cambridge, Mass.), and is generally part of an upper chamber that is in fluid contact with a lower chamber containing pro-angiogenic stimuli. Migration is generally assayed after an overnight incubation with stimuli, but longer or shorter time frames may also be used. Migration is assessed as the number of cells that crossed the lamina, and may be detected by staining cells with hemotoxylin solution (VWR Scientific.), or by any other method for determining cell number. In another exemplary set up, cells are fluorescently labeled and migration is detected using fluorescent readings, for instance using the Falcon HTS FluoroBlok (Becton Dickinson). While some migration is observed in the absence of stimulus, migration is greatly increased in response to pro-angiogenic factors. The assay can be used to test the effect of a ET2-binding ligand on endothelial cell migration.

Sprouting assay. An exemplary sprouting assay is a three-dimensional in vitro angiogenesis assay that uses a cell-number defined spheroid aggregation of endothelial cells ("spheroid"), embedded in a collagen gel-based matrix. The spheroid can serve as a starting point for the sprouting of capillary-like structures by invasion into the extracellular matrix (termed "cell sprouting") and the subsequent formation of complex anastomosing networks (Korff and Augustin, 1999, J Cell Sci 112:3249-58). In an exemplary experimental set-up, spheroids are prepared by pipetting 400 human umbilical vein endothelial cells (HUMVECs) into individual wells of a nonadhesive 96-well plates to allow overnight spheroidal aggregation (Korff and Augustin, J Cell Biol 143: 1341-52, 1998). Spheroids are harvested and seeded in 900 μl of methocel-collagen solution and pipetted into individual wells of a 24 well plate to allow collagen gel polymerization. Test agents are added after 30 min by pipetting 100 μl of 10-fold concentrated working dilution of the test substances on top of the gel. Plates are incubated at 37° C. for 24 h. Dishes are fixed at the end of the experimental incubation period by addition of paraformaldehyde. Sprouting intensity of endothelial cells can be quantitated by an automated image analysis system to determine the cumulative sprout length per spheroid.

In some embodiments, an ET2 binding ligand has a statistically significant effect in an assay described herein, e.g., a cellular assay described herein.

Pharmaceutical Compositions

In another aspect, the present invention provides compositions, e.g., pharmaceutically acceptable compositions, which include an ET2-ligand, e.g., an antibody molecule, other polypeptide or peptide identified as binding to ET2, or described herein, formulated together with a pharmaceutically acceptable carrier. As used herein, "pharmaceutical compositions" encompass labeled ligands for in vivo imaging as well as therapeutic compositions.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., protein ligand may be coated in a material to protect the compound from the action of acids and other natural conditions that may inactivate the compound.

A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for administration of humans with antibodies. The preferred mode of administration is parenteral (e.g., intravenous, subcutaneous, intraperitoneal, intramuscular). In one embodiment, the ET2-ligand is administered by intravenous infusion or injection. In another preferred embodiment, the ET2-ligand is administered by intramuscular or subcutaneous injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Pharmaceutical compositions typically must be sterile and stable under the conditions of manufacture and storage. A pharmaceutical composition can also be tested to insure it meets regulatory and industry standards for administration. For example, endotoxin levels in the preparation can be tested using the *Limulus amebocyte* lysate assay (e.g., using the kit from Bio Whittaker lot # 7L3790, sensitivity 0.125 EU/mL) according to the USP 24/NF 19 methods. Sterility of pharmaceutical compositions can be determined using thioglycollate medium according to the USP 24/NF 19 methods. For example, the preparation is used to inoculate the thioglycollate medium and incubated at 35° C. for 14 or more days. The medium is inspected periodically to detect growth of a microorganism.

The composition can be formulated as a solution, microemulsion, dispersion, liposome, or other ordered structure suitable to high drug concentration. Sterile injectable solutions can be prepared by incorporating the active compound (i.e., the ligand) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The anti-ET2 protein ligands of the present invention can be administered by a variety of methods known in the art, although for many applications, the preferred route/mode of administration is intravenous injection or infusion. For example, for therapeutic applications, the ET2-ligand can be administered by intravenous infusion at a rate of less than 30, 20, 10, 5, or 1 mg/min to reach a dose of about 1 to 100 $mg/m^2$ or 7 to 25 $mg/m^2$. The route and/or mode of administration will vary depending upon the desired results. In certain embodiments, the active compound may be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., *Sustained and Controlled Release Drug Delivery Systems*, J. R. Robinson, ed., Marcel Dekker, Inc., New York, 1978.

In certain embodiments, the ligand may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Pharmaceutical compositions can be administered with medical devices known in the art. For example, in one embodiment, a pharmaceutical composition of the invention can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Of course, many other such implants, delivery systems, and modules are also known.

In certain embodiments, the compounds of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties that are selectively transported into specific cells or organs, thus enhance targeted drug delivery (see, e.g., V. V. Ranade (1989) *J. Clin. Pharmacol.* 29:685).

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of an antibody of the invention is 0.1-20 mg/kg, more preferably 1-10 mg/kg. The anti-ET2 antibody can be administered by intravenous infusion at a rate of less than 30, 20, 10, 5, or 1 mg/min to reach a dose of about 1 to 100 $mg/m^2$ or about 5 to 30 $mg/m^2$. For ligands smaller in molecular weight than an antibody, appropriate amounts can be proportionally less. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The pharmaceutical compositions of the invention may include a "therapeutically effective amount" or a "prophylactically effective amount" of an ET2-ligand of the invention. A "therapeutically effective amount" refers to an amount effective, at dosages and for periods of time necessary, to achieve the desired therapeutic result. A therapeutically effective amount of the composition may vary according to factors such as the disease state, age, sex, and weight of the individual, and the ability of the protein ligand to elicit a desired response in the individual. A therapeutically effective amount is also one in which any toxic or detrimental effects of the composition is outweighed by the therapeutically beneficial effects. A "therapeutically effective dosage" preferably inhibits a measurable parameter, e.g., tumor growth rate by at least about 20%, more preferably by at least about 40%, even more preferably by at least about 60%, and still more preferably by at least about 80% relative to untreated subjects. The ability of a compound to inhibit a measurable parameter, e.g., cancer, can be evaluated in an animal model system predictive of efficacy in human tumors. Alternatively, this property of a composition can be evaluated by examining the ability of the compound to inhibit, such inhibition in vitro by assays known to the skilled practitioner.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Also within the scope of the invention are kits comprising the protein ligand that binds to ET2 and instructions for use, e.g., treatment, prophylactic, or diagnostic use. In one embodiment, the instructions for diagnostic applications include the use of the ET2-ligand (e.g., antibody or antigen-binding fragment thereof, or other polypeptide or peptide) to detect ET2, in vitro, e.g., in a sample, e.g., a biopsy or cells from a patient having a cancer or neoplastic disorder, or in vivo. In another embodiment, the instructions for therapeutic applications include suggested dosages and/or modes of administration in a patient with a cancer or neoplastic disorder. The kit can further contain a least one additional reagent, such as a diagnostic or therapeutic agent, e.g., a diagnostic or therapeutic agent as described herein, and/or one or more additional ET2-ligands, formulated as appropriate, in one or more separate pharmaceutical preparations.

Stabilization and Retention

In one embodiment, an ET2-ligand is physically associated with a moiety that improves its stabilization and/or retention in circulation, e.g., in blood, serum, lymph, or other tissues, e.g., by at least 1.5, 2, 5, 10, or 50 fold.

For example, an ET2-ligand can be associated with a polymer, e.g., a substantially non-antigenic polymers, such as polyalkylene oxides or polyethylene oxides. Suitable polymers will vary substantially by weight. Polymers having molecular number average weights ranging from about 200 to about 35,000 (or about 1,000 to about 15,000, and 2,000 to about 12,500) can be used.

For example, an ET2-ligand can be conjugated to a water soluble polymer, e.g., hydrophilic polyvinyl polymers, e.g. polyvinylalcohol and polyvinylpyrrolidone. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene (Pluronics); polymethacrylates; carbomers; branched or unbranched polysaccharides which comprise the saccharide monomers D-mannose, D- and L-galactose, fucose, fructose, D-xylose, L-arabinose, D-glucuronic acid, sialic acid, D-galacturonic acid, D-mannuronic acid (e.g. polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextrane sulfate, dextran, dextrins, glycogen, or the polysaccharide subunit of acid mucopolysaccharides, e.g. hyaluronic acid; polymers of sugar alcohols such as polysorbitol and polymannitol; heparin or heparon.

Other compounds can also be attached to the same polymer, e.g., a cytotoxin, a label, or another targeting agent, e.g., another ET2-ligand or an unrelated ligand. Mono-activated, alkoxy-terminated polyalkylene oxides (PAO's), e.g., monomethoxy-terminated polyethylene glycols (mPEG's); $C_{1-4}$ alkyl-terminated polymers; and bis-activated polyethylene oxides (glycols) can be used for crosslinking. See, e.g., U.S. Pat. No. 5,951,974.

In one embodiment, the polymer prior to cross-linking to the ligand need not be, but preferably is, water soluble. Generally, after crosslinking, the product is water soluble, e.g., exhibits a water solubility of at least about 0.01 mg/ml, and more preferably at least about 0.1 mg/ml, and still more preferably at least about 1 mg/ml. In addition, the polymer should not be highly immunogenic in the conjugate form, nor should it possess viscosity that is incompatible with intravenous infusion or injection if the conjugate is intended to be administered by such routes.

In one embodiment, the polymer contains only a single group which is reactive. This helps to avoid cross-linking of ligand molecules to one another. However, it is within the scope herein to maximize reaction conditions to reduce cross-linking between ligand molecules, or to purify the reaction products through gel filtration or ion exchange chromatography to recover substantially homogenous derivatives. In other embodiments, the polymer contains two or more reactive groups for the purpose of linking multiple ligands to the polymer backbone. Again, gel filtration or ion exchange chromatography can be used to recover the desired derivative in substantially homogeneous form.

The molecular weight of the polymer can range up to about 500,000 D, and preferably is at least about 20,000 D, or at least about 30,000 D, or at least about 40,000 D. The molecular weight chosen can depend upon the effective size of the conjugate to be achieved, the nature (e.g. structure, such as linear or branched) of the polymer, and the degree of derivatization.

A covalent bond can be used to attach an ET2-ligand to a polymer, for example, crosslinking to the N-terminal amino group of the ligand and epsilon amino groups found on lysine residues of the ligand, as well as other amino, imino, carboxyl, sulfhydryl, hydroxyl or other hydrophilic groups. The polymer may be covalently bonded directly to the ET2-ligand without the use of a multifunctional (ordinarily bifunctional) crosslinking agent. Covalent binding to amino groups is accomplished by known chemistries based upon cyanuric chloride, carbonyl diimidazole, aldehyde reactive groups (PEG alkoxide plus diethyl acetal of bromoacetaldehyde; PEG plus DMSO and acetic anhydride, or PEG chloride plus the phenoxide of 4-hydroxybenzaldehyde, activated succinimidyl esters, activated dithiocarbonate PEG, 2,4,5-trichlorophenylcloroformate or P-nitrophenylcloroformate activated PEG.) Carboxyl groups can be derivatized by coupling PEG-amine using carbodiimide. Sulfhydryl groups can be derivatized by coupling to maleimido-substituted PEG (e.g. alkoxy-PEG amine plus sulfosuccinimidyl 4-(N-maleimidomethyl)cyclohexane-1-carboxylate) WO 97/10847 or PEG-maleimide commercially available from Shearwater Polymers, Inc., Huntsville, Ala.). Alternatively, free amino groups on the ligand (e.g. epsilon amino groups on lysine residues) can be thiolated with 2-imino-thiolane (Traut's reagent) and then coupled to maleimide-containing derivatives of PEG, e.g., as described in Pedley et al., Br. J. Cancer, 70: 1126-1130 (1994).

Functionalized PEG polymers that can be attached to an ET2-ligand are available, e.g., from Shearwater Polymers, Inc. (Huntsville, Ala.). Such commercially available PEG derivatives include, e.g., amino-PEG, PEG amino acid esters, PEG-hydrazide, PEG-thiol, PEG-succinate, carboxymethylated PEG, PEG-propionic acid, PEG amino acids, PEG succinimidyl succinate, PEG succinimidyl propionate, succinimidyl ester of carboxymethylated PEG, succinimidyl carbonate of PEG, succinimidyl esters of amino acid PEGs, PEG-oxycarbonylimidazole, PEG-nitrophenyl carbonate, PEG tresylate, PEG-glycidyl ether, PEG-aldehyde, PEG vinylsulfone, PEG-maleimide, PEG-orthopyridyl-disulfide, heterofunctional PEGs, PEG vinyl derivatives, PEG silanes, and PEG phospholides. The reaction conditions for coupling these PEG derivatives may vary depending on the ET2-ligand, the desired degree of PEGylation, and the PEG derivative utilized. Some factors involved in the choice of PEG derivatives include: the desired point of attachment (such as lysine or cysteine R-groups), hydrolytic stability and reactivity of the derivatives, stability, toxicity and antigenicity of the linkage, suitability for analysis, etc. Specific instructions for the use of any particular derivative are available from the manufacturer.

The conjugates of an ET2-ligand and a polymer can be separated from the unreacted starting materials, e.g., by gel filtration or ion exchange chromatography, e.g., HPLC. Heterologous species of the conjugates are purified from one another in the same fashion. Resolution of different species (e.g. containing one or two PEG residues) is also possible due to the difference in the ionic properties of the unreacted amino acids. See, e.g., WO 96/34015.

Kits

An ET2 ligand described herein can be provided in a kit, e.g., as a component of a kit. For example, the kit includes (a) an ET2 ligand, e.g., a composition that includes an ET2 ligand, and, optionally (b) informational material. The informational material can be descriptive, instructional, marketing or other material that relates to the methods described herein and/or the use of an ET2 ligand for the methods described herein.

The informational material of the kits is not limited in its form. In one embodiment, the informational material can include information about production of the compound, molecular weight of the compound, concentration, date of expiration, batch or production site information, and so forth. In one embodiment, the informational material relates to using the ligand to treat, prevent, or diagnosis a disorder described herein, e.g., an angiogenesis or an endothelial-cell related disorder.

In one embodiment, the informational material can include instructions to administer an ET2 ligand in a suitable manner to perform the methods described herein, e.g., in a suitable dose, dosage form, or mode of administration (e.g., a dose, dosage form, or mode of administration described herein). In another embodiment, the informational material can include instructions to administer an ET2 ligand to a suitable subject, e.g., a human, e.g., a human having, or at risk for, increased angiogenesis (e.g., cancer or metastatic cancer. For example, the material can include instructions to administer an ET2 ligand to a cancer patient, a patient with an inflammatory disorder, or a patient with excessive endothelial cell activity.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as computer readable material, video recording, or audio recording. In another embodiment, the informational material of the kit is contact information, e.g., a physical address, email address, website, or telephone number, where a user of the kit can obtain substantive information about an ET2 ligand and/or its use in the methods described herein. Of course, the informational material can also be provided in any combination of formats.

In addition to an ET2 ligand, the composition of the kit can include other ingredients, such as a solvent or buffer, a stabilizer, a preservative, a flavoring agent (e.g., a bitter antagonist or a sweetener), a fragrance or other cosmetic ingredient, and/or a second agent for treating a condition or disorder described herein, e.g., cancer or inflammation. Alternatively, the other ingredients can be included in the kit, but in different compositions or containers than an ET2 ligand. In such embodiments, the kit can include instructions for admixing an ET2 ligand and the other ingredients, or for using an ET2 ligand together with the other ingredients.

An ET2 ligand can be provided in any form, e.g., liquid, dried or lyophilized form. It is preferred that an ET2 ligand be substantially pure and/or sterile. When an ET2 ligand is provided in a liquid solution, the liquid solution preferably is an aqueous solution, with a sterile aqueous solution being preferred. When an ET2 ligand is provided as a dried form, reconstitution generally is by the addition of a suitable solvent. The solvent, e.g., sterile water or buffer, can optionally be provided in the kit.

The kit can include one or more containers for the composition containing an ET2 ligand. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of an ET2 ligand, For example, the kit includes a plurality of syringes, ampules, foil packets, or blister packs, each containing a single unit dose of an ET2 ligand. The containers of the kits can be air tight, waterproof (e.g., impermeable to changes in moisture or evaporation), and/or light-tight.

The kit optionally includes a device suitable for administration of the composition, e.g., a syringe, inhalant, pipette, forceps, measured spoon, dropper (e.g., eye dropper), swab (e.g., a cotton swab or wooden swab), or any such delivery device. In a preferred embodiment, the device is an implantable device that dispenses metered doses of the ligand.

Treatments

Protein ligands that bind to ET2 and identified by the method described herein and/or detailed herein have therapeutic and prophylactic utilities. For example, these ligands can be administered to cells in culture, e.g. in vitro or ex vivo, or in a subject, e.g., in vivo, to treat, prevent, and/or diagnose a variety of disorders, such as diseases characterized by unwanted angiogenesis, e.g., cancers.

As used herein, the term “treat” or “treatment” is defined as the application or administration of an anti-ET2 antibody, alone or in combination with, a second agent to a subject, e.g., a patient, or application or administration of the agent to an isolated tissue or cell, e.g., cell line, from a subject, e.g., a patient, who has a disorder (e.g., a disorder as described herein), a symptom of a disorder or a predisposition toward a disorder, with the purpose to cure, heal, alleviate, relieve, alter, remedy, ameliorate, improve or affect the disorder, the symptoms of the disorder or the predisposition toward the disorder. Treating a cell refers to the inhibition, ablation or killing of a cell in vitro or in vivo, or otherwise reducing capacity of a cell, e.g., an aberrant cell, to mediate a disorder, e.g., a disorder as described herein (e.g., a cancerous disorder). In one embodiment, "treating a cell" refers to a reduction in the activity and/or proliferation of a cell, e.g., a hyperproliferative cell. Such reduction does not necessarily indicate a total elimination of the cell, but a reduction, e.g., a statistically significant reduction, in the activity or the growth rate of the cell.

As used herein, an amount of an ET2-ligand effective to treat a disorder, or a "therapeutically effective amount" refers to an amount of the ligand which is effective, upon single or multiple dose administration to a subject, in treating a cell, e.g., a cancer cell (e.g., a ET2-expressing cancer cell), or in prolonging life of, curing, alleviating, relieving or improving the condition of a subject with a disorder as described herein beyond that expected in the absence of such treatment. As used herein, "inhibiting the growth" of the neoplasm refers to slowing, interrupting, arresting or stopping its growth and metastases and does not necessarily indicate a total elimination of the neoplastic growth.

As used herein, an amount of an ET2-ligand effective to prevent a disorder, or a "a prophylactically effective amount" of the ligand refers to an amount of an ET2-ligand, e.g., an anti-ET2 antibody described herein, which is effective, upon single- or multiple-dose administration to the subject, in preventing or delaying the occurrence of the onset or recurrence of a disorder, e.g., a cancer.

The terms "induce", "inhibit", "potentiate", "elevate", "increase", "decrease" or the like, e.g., which denote quantitative differences between two states, refer to a difference, e.g., a statistically significant difference, between the two states. For example, "an amount effective to inhibit the proliferation of the ET2-expressing hyperproliferative cells" means that the rate of growth of the cells will be different, e.g., statistically significantly different, from the untreated cells.

As used herein, the term "subject" is intended to include human and non-human animals. Preferred human animals include a human patient having a disorder characterized by abnormal cell proliferation or cell differentiation. The term "non-human animals" of the invention includes all vertebrates, e.g., non-mammals (such as chickens, amphibians, reptiles) and mammals, such as non-human primates, sheep, dog, cow, pig, etc.

In one embodiment, the subject is a human subject. Alternatively, the subject can be a mammal expressing a ET2-like antigen with which an antibody of the invention cross-reacts. A protein ligand of the invention can be administered to a human subject for therapeutic purposes (discussed further below). Moreover, an ET2-ligand can be administered to a non-human mammal expressing the ET2-like antigen to which the ligand binds (e.g., a primate, pig or mouse) for veterinary purposes or as an animal model of human disease. Regarding the latter, such animal models may be useful for evaluating the therapeutic efficacy of the ligand (e.g., testing of dosages and time courses of administration).

In one embodiment, the invention provides a method of treating (e.g., ablating, killing, reducing growth of cell division of) a cell (e.g., a non-cancerous cell, e.g., a normal, benign or hyperplastic cell, or a cancerous cell, e.g., a malignant cell, e.g., cell found in a solid tumor, a soft tissue tumor, or a metastatic lesion (e.g., a cell found in renal, urothelial, colonic, rectal, pulmonary, breast or hepatic, cancers and/or metastasis))s. Methods of the invention include the steps of contacting the cell with an ET2-ligand, e.g., an anti-ET2 antibody described herein, in an amount sufficient to treat, e.g., inhibit cell growth or division, or ablate or kill the cell.

The subject method can be used on cells in culture, e.g. in vitro or ex vivo. For example, cancerous or metastatic cells (e.g., renal, urothelial, colon, rectal, lung, breast, ovarian, prostatic, or liver cancerous or metastatic cells) can be cultured in vitro in culture medium and the contacting step can be effected by adding the ET2-ligand to the culture medium. The method can be performed on cells (e.g., cancerous or metastatic cells) present in a subject, as part of an in vivo (e.g., therapeutic or prophylactic) protocol. For in vivo embodiments, the contacting step is effected in a subject and includes administering the ET2-ligand to the subject under conditions effective to permit both binding of the ligand to the cell and the treating, e.g., the inhibition of growth or division, or the killing or ablating of the cell.

The inhibitors of ET2 can reduce angiogenesis (e.g., uncontrolled or unwanted angiogenesis)—such as angiogenesis associated with vascular malformations and cardiovascular disorders (e.g., atherosclerosis, restenosis and arteriovenous malformations), chronic inflammatory diseases (e.g., diabetes mellitus, inflammatory bowel disease, psoriasis and rheumatoid arthritis), aberrant wound repairs (e.g., those that are observed following excimer laser eye surgery), circulatory disorders (e.g., Raynaud's phenomenon), crest syndromes (e.g., calcinosis, esophageal and dyomotiloty), dermatological disorders (e.g., Port-wine stains, arterial ulcers, systemic vasculitis and scleroderma), or ocular disorders (e.g., blindness caused by neovascular disease, neovascular glaucoma, corneal neovascularization, trachoma, diabetic retinopathy and myopic degeneration). See, e.g., Carmeliet and Jain, *Nature,* 407: 249-257, 2000.

The method can be used to treat a cancer. As used herein, the terms "cancer", "hyperproliferative", "malignant", and "neoplastic" are used interchangeably, and refer to those cells in an abnormal state or condition characterized by rapid proliferation or neoplasm. The terms include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth.

The common medical meaning of the term "neoplasia" refers to "new cell growth" that results as a loss of responsiveness to normal growth controls, e.g. to neoplastic cell growth. A "hyperplasia" refers to cells undergoing an abnormally high rate of growth. However, as used herein, the terms neoplasia and hyperplasia can be used interchangeably, as their context will reveal, referring generally to cells experiencing abnormal cell growth rates. Neoplasias and hyperplasias include "tumors," which may be benign, premalignant or malignant.

Examples of cancerous disorders include, but are not limited to, solid tumors, soft tissue tumors, and metastatic lesions. Examples of solid tumors include malignancies, e.g., sarcomas, adenocarcinomas, and carcinomas, of the various organ systems, such as those affecting lung, breast, lymphoid, gastrointestinal (e.g., colon), and genitourinary tract (e.g., renal, urothelial cells), pharynx, prostate, ovary as well as adenocarcinomas which include malignancies such as most colon cancers, rectal cancer, renal-cell carcinoma, liver cancer, non-small cell carcinoma of the lung, cancer of the small intestine and so forth. Metastatic lesions of the aforementioned cancers can also be treated or prevented using the methods and compositions of the invention.

The subject method can be useful in treating malignancies of the various organ systems, such as those affecting lung, breast, lymphoid, gastrointestinal (e.g., colon), and genitourinary tract, prostate, ovary, pharynx, as well as adenocarcinomas which include malignancies such as most colon cancers, renal-cell carcinoma, prostate cancer and/or testicular tumors, non-small cell carcinoma of the lung, cancer of the small intestine and cancer of the esophagus. Exemplary solid tumors that can be treated include: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

The term "carcinoma" is recognized by those skilled in the art and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is recognized by those skilled in the art and refers to malignant tumors of mesenchymal derivation.

The subject method can also be used to inhibit the proliferation of hyperplastic/neoplastic cells of hematopoietic origin, e.g., arising from myeloid, lymphoid or erythroid lineages, or precursor cells thereof. For instance, the present invention contemplates the treatment of various myeloid disorders including, but not limited to, acute promyeloid leukemia (APML), acute myelogenous leukemia (AML) and chronic myelogenous leukemia (CML) (reviewed in Vaickus, L. (1991) *Crit Rev. in Oncol./Hemotol.* 11:267-97). Lymphoid malignancies which may be treated by the subject method include, but are not limited to acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas contemplated by the treatment method of the present invention include, but are not limited to, non-Hodgkin's lymphoma and variants thereof, peripheral T-cell lymphomas, adult T-cell leukemia/lymphoma (ATL), cutaneous T-cell lymphoma (CTCL), large granular lymphocytic leukemia (LGF) and Hodgkin's disease.

ET2 ligands that are agonists can be used to stimulate angiogenesis, e.g., aid wound healing, burns, and other disorders which require increased angiogenesis.

Methods of administering ET2-ligands are described in "Pharmaceutical Compositions". Suitable dosages of the molecules used will depend on the age and weight of the subject and the particular drug used. The ligands can be used as competitive agents to inhibit, reduce an undesirable interaction, e.g., between a natural or pathological agent and the ET2.

In one embodiment, the ET2-ligands are used to kill, ablate, or inhibit the growth of cancerous cells and normal, benign hyperplastic, and cancerous cells in vivo. The ligands can be used by themselves or conjugated to an agent, e.g., a cytotoxic drug, radioisotope. This method includes: administering the ligand alone or attached to a cytotoxic drug, to a subject requiring such treatment.

The terms "cytotoxic agent" and "cytostatic agent" and "anti-tumor agent" are used interchangeably herein and refer to agents that have the property of inhibiting the growth or proliferation (e.g., a cytostatic agent), or inducing the killing, of hyperproliferative cells, e.g., an aberrant cancer cell. In cancer therapeutic embodiment, the term "cytotoxic agent" is used interchangeably with the terms "anti-cancer" or "anti-tumor" to mean an agent, which inhibits the development or progression of a neoplasm, particularly a solid tumor, a soft tissue tumor, or a metastatic lesion.

Nonlimiting examples of anti-cancer agents include, e.g., antimicrotubule agents, topoisomerase inhibitors, antimetabolites, mitotic inhibitors, alkylating agents, intercalating agents, agents capable of interfering with a signal transduction pathway, agents that promote apoptosis, radiation, and antibodies against other tumor-associated antigens (including naked antibodies, immunotoxins and radioconjugates). Examples of the particular classes of anti-cancer agents are provided in detail as follows: antitubulin/antimicrotubule, e.g., paclitaxel, vincristine, vinblastine, vindesine, vinorelbin, taxotere; topoisomerase I inhibitors, e.g., topotecan, camptothecin, doxorubicin, etoposide, mitoxantrone, daunorubicin, idarubicin, teniposide, amsacrine, epirubicin, merbarone, piroxantrone hydrochloride; antimetabolites, e.g., 5-fluorouracil (5-FU), methotrexate, 6-mercaptopurine, 6-thioguanine, fludarabine phosphate, cytarabine/Ara-C, trimetrexate, gemcitabine, acivicin, alanosine, pyrazofurin, N-Phosphoracetyl-L-Asparate=PALA, pentostatin, 5-azacitidine, 5-Aza 2'-deoxycytidine, ara-A, cladribine, 5-fluorouridine, FUDR, tiazofurin, N-[5-[N-(3,4-dihydro-2-methyl-4-oxoquinazolin-6-ylmethyl)-N-methylamino]-2-thenoyl]-L-glutamic acid; alkylating agents, e.g., cisplatin, carboplatin, mitomycin C, BCNU=Carmustine, melphalan, thiotepa, busulfan, chlorambucil, plicamycin, dacarbazine, ifosfamide phosphate, cyclophosphamide, nitrogen mustard, uracil mustard, pipobroman, 4-ipomeanol; agents acting via other mechanisms of action, e.g., dihydrolenperone, spiromustine, and desipeptide; biological response modifiers, e.g., to enhance anti-tumor responses, such as interferon; apoptotic agents, such as actinomycin D; and anti-hormones, for example anti-estrogens such as tamoxifen or, for example antiandrogens such as 4'-cyano-3-(4-fluorophenylsulphonyl)-2-hydroxy-2-methyl-3'-(trifluoromethyl)propionanilide.

ET2-ligands can recognize normal, endothelial cells. The ligands can also bind to cells in the vicinity of the cancerous cells. The ligands can inhibit the growth of, and/or kill these cells. In this manner, the ligands may indirectly attack the cancerous cells which may rely on surrounding cells for nutrients, growth signals and so forth. Thus, the ET2-ligands (e.g., modified with a cytotoxin) can selectively target cells in cancerous tissue (including the cancerous cells themselves).

The ligands may be used to deliver a variety of cytotoxic drugs including therapeutic drugs, a compound emitting radiation, molecules of plants, fungal, or bacterial origin, biological proteins, and mixtures thereof. The cytotoxic drugs can be intracellularly acting cytotoxic drugs, such as short-range radiation emitters, including, for example, short-range, high-energy α-emitters, as described herein.

Enzymatically active toxins and fragments thereof are exemplified by diphtheria toxin A fragment, nonbinding active fragments of diphtheria toxin, exotoxin A (from *Pseudomonas aeruginosa*), ricin A chain, abrin A chain, modeccin A chain, α-sacrin, certain *Aleurites fordii* proteins, certain Dianthin proteins, *Phytolacca americana* proteins (PAP, PAPII and PAP-S), *Morodica charantia* inhibitor, curcin, crotin, *Saponaria officinalis* inhibitor, gelonin, mitogillin, restrictocin, phenomycin, and enomycin. Procedures for preparing enzymatically active polypeptides of the immunotoxins are described in W084/03508 and W085/03508. Examples of cytotoxic moieties that can be conjugated to the antibodies include adriamycin, chlorambucil, daunomycin, methotrexate, neocarzinostatin, and platinum.

In the case of polypeptide toxins, recombinant nucleic acid techniques can be used to construct a nucleic acid that encodes the ligand (e.g., antibody or antigen-binding fragment thereof) and the cytotoxin (or a polypeptide component thereof) as translational fusions. The recombinant nucleic acid is then expressed, e.g., in cells and the encoded fusion polypeptide isolated.

Procedures for conjugating protein ligands (e.g., antibodies) with the cytotoxic agents have been previously described. Procedures for conjugating chlorambucil with antibodies are described by Flechner (1973) *European Journal of Cancer,* 9:741-745; Ghose et al. (1972) *British Medical Journal,* 3:495-499; and Szekerke, et al. (1972) *Neoplasma,* 19:211-215. Procedures for conjugating daunomycin and adriamycin to antibodies are described by Hurwitz, E. et al. (1975) *Cancer Research,* 35:1175-1181 and Arnon et al. (1982) *Cancer Surveys,* 1:429-449. Procedures for preparing antibody-ricin conjugates are described in U.S. Pat. No. 4,414,148 and by Osawa, T., et al. (1982) *Cancer Surveys,* 1:373-388 and the references cited therein. Coupling procedures as also described in EP 86309516.2.

To kill or ablate normal, benign hyperplastic, or cancerous cells, a first protein ligand is conjugated with a prodrug which is activated only when in close proximity with a prodrug activator. The prodrug activator is conjugated with a second protein ligand, preferably one which binds to a non-competing site on the target molecule. Whether two protein ligands bind to competing or non-competing binding sites can be determined by conventional competitive binding assays. Drug-prodrug pairs suitable for use in the practice of the present invention are described in Blakey et al., (1996) *Cancer Research,* 56:3287-3292.

Alternatively, the ET2-ligand can be coupled to high energy radiation emitters, for example, a radioisotope, such as $^{131}I$, a γ-emitter, which, when localized at the tumor site, results in a killing of several cell diameters. See, e.g., S. E. Order, "Analysis, Results, and Future Prospective of the Therapeutic Use of Radiolabeled Antibody in Cancer Therapy", *Monoclonal Antibodies for Cancer Detection and Therapy*, R. W. Baldwin et al. (eds.), pp 303-316 (Academic Press 1985). Other suitable radioisotopes include α-emitters, such as $^{212}Bi$, $^{213}Bi$, and $^{211}At$, and β-emitters, such as $^{186}Re$ and $^{90}Y$. Moreover, $Lu^{117}$ may also be used as both an imaging and cytotoxic agent.

Radioimmunotherapy (RIT) using antibodies labeled with $^{131}I$, $^{90}Y$, and $^{177}Lu$ is under intense clinical investigation. There are significant differences in the physical characteristics of these three nuclides and as a result, the choice of radionuclide is very critical in order to deliver maximum radiation dose to the tumor. The higher beta energy particles of $^{90}Y$ may be good for bulky tumors. The relatively low energy beta particles of $^{131}I$ are ideal, but in vivo dehalogenation of radioiodinated molecules is a major disadvantage for internalizing antibody. In contrast, $^{177}Lu$ has low energy beta particle with only 0.2-0.3 mm range and delivers much lower radiation dose to bone marrow compared to $^{90}Y$. In addition, due to longer physical half-life (compared to $^{90}Y$), the tumor residence times are higher. As a result, higher activities (more mCi amounts) of $^{177}Lu$ labeled agents can be administered with comparatively less radiation dose to marrow. There have been several clinical studies investigating the use of $^{177}Lu$ labeled antibodies in the treatment of various cancers. (Mulligan T et al. (1995) *Clin Cancer Res.* 1: 1447-1454; Meredith R F, et al. (1996) *J Nucl Med* 37:1491-1496; Alvarez R D, et al. (1997) *Gynecologic Oncology* 65:94-101).

The ET2-ligands can be used directly in vivo to eliminate antigen-expressing cells via natural complement-dependent cytotoxicity (CDC) or antibody-dependent cellular cytotoxicity (ADCC). The protein ligands of the invention, can include complement binding effector domain, such as the Fc portions from IgG1, -2, or -3 or corresponding portions of IgM which bind complement. In one embodiment, a population of target cells is ex vivo treated with a binding agent of the invention and appropriate effector cells. The treatment can be supplemented by the addition of complement or serum containing complement. Further, phagocytosis of target cells coated with a protein ligand of the invention can be improved by binding of complement proteins. In another embodiment target, cells coated with the protein ligand that includes a complement binding effector domain are lysed by complement.

Also encompassed by the present invention is a method of killing or ablating which involves using the ET2-ligand for prophylaxis. For example, these materials can be used to prevent or delay development or progression of cancers.

Use of the therapeutic methods of the present invention to treat cancers has a number of benefits. Since the protein ligands specifically recognize ET2, other tissue is spared and high levels of the agent are delivered directly to the site where therapy is required. Treatment in accordance with the present invention can be effectively monitored with clinical parameters. Alternatively, these parameters can be used to indicate when such treatment should be employed.

ET2-ligands of the invention can be administered in combination with one or more of the existing modalities for treating cancers, including, but not limited to: surgery; radiation therapy, and chemotherapy.

Diagnostic Uses

Protein ligands that bind to ET2 and identified by the method described herein and/or detailed herein have in vitro and in vivo diagnostic, therapeutic and prophylactic utilities.

In one aspect, the present invention provides a diagnostic method for detecting the presence of a ET2, in vitro (e.g., a biological sample, such as tissue, biopsy, e.g., a cancerous tissue) or in vivo (e.g., in vivo imaging in a subject).

The method includes: (i) contacting a sample with ET2-ligand; and (ii) detecting formation of a complex between the ET2-ligand and the sample. The method can also include contacting a reference sample (e.g., a control sample) with the ligand, and determining the extent of formation of the complex between the ligand an the sample relative to the same for the reference sample. A change, e.g., a statistically significant change, in the formation of the complex in the sample or subject relative to the control sample or subject can be indicative of the presence of ET2 in the sample.

Another method includes: (i) administering the ET2-ligand to a subject; and (iii) detecting formation of a complex between the ET2-ligand, and the subject. The detecting can include determining location or time of formation of the complex.

The ET2-ligand can be directly or indirectly labeled with a detectable substance to facilitate detection of the bound or unbound antibody. Suitable detectable substances include various enzymes, prosthetic groups, fluorescent materials, luminescent materials and radioactive materials.

Complex formation between the ET2-ligand and ET2 can be detected by measuring or visualizing either the ligand bound to the ET2 or unbound ligand. Conventional detection assays can be used, e.g., an enzyme-linked immunosorbent assays (ELISA), a radioimmunoassay (RIA) or tissue immunohistochemistry. Further to labeling the ET2-ligand, the presence of ET2 can be assayed in a sample by a competition immunoassay utilizing standards labeled with a detectable substance and an unlabeled ET2-ligand. In one example of this assay, the biological sample, the labeled standards and the ET2 binding agent are combined and the amount of labeled standard bound to the unlabeled ligand is determined. The amount of ET2 in the sample is inversely proportional to the amount of labeled standard bound to the ET2 binding agent.

Fluorophore and chromophore labeled protein ligands can be prepared. Since antibodies and other proteins absorb light having wavelengths up to about 310 nm, the fluorescent moieties should be selected to have substantial absorption at wavelengths above 310 nm and preferably above 400 nm. A variety of suitable fluorescers and chromophores are described by Stryer (1968) *Science,* 162:526 and Brand, L. et al. (1972) *Annual Review of Biochemistry,* 41:843-868. The protein ligands can be labeled with fluorescent chromophore groups by conventional procedures such as those disclosed in U.S. Pat. Nos. 3,940,475, 4,289,747, and 4,376,110. One group of fluorescers having a number of the desirable properties described above is the xanthene dyes, which include the fluoresceins and rhodamines. Another group of fluorescent compounds are the naphthylamines. Once labeled with a fluorophore or chromophore, the protein ligand can be used to detect the presence or localization of the ET2 in a sample, e.g., using fluorescent microscopy (such as confocal or deconvolution microscopy).

Histological Analysis. Immunohistochemistry can be performed using the protein ligands described herein. For example, in the case of an antibody, the antibody can synthesized with a label (such as a purification or epitope tag), or can be detectably labeled, e.g., by conjugating a label or label-binding group. For example, a chelator can be attached to the antibody. The antibody is then contacted to a histological preparation, e.g., a fixed section of tissue that is on a microscope slide. After an incubation for binding, the preparation is washed to remove unbound antibody. The preparation is then analyzed, e.g., using microscopy, to identify if the antibody bound to the preparation.

Of course, the antibody (or other polypeptide or peptide) can be unlabeled at the time of binding. After binding and washing, the antibody is labeled in order to render it detectable.

Protein Arrays. The ET2-ligand can also be immobilized on a protein array. The protein array can be used as a diagnostic tool, e.g., to screen medical samples (such as isolated cells, blood, sera, biopsies, and the like). Of course, the protein array can also include other ligands, e.g., that bind to ET2 or to other target molecules.

Methods of producing polypeptide arrays are described, e.g., in De Wildt et al. (2000) *Nat. Biotechnol.* 18:989-994; Lueking et al. (1999) *Anal. Biochem.* 270:103-111; Ge (2000) *Nucleic Acids Res.* 28, e3, I-VII; MacBeath and Schreiber (2000) *Science* 289:1760-1763; WO 01/40803 and WO 99/51773A1. Polypeptides for the array can be spotted at high speed, e.g., using commercially available robotic apparati, e.g., from Genetic MicroSystems or BioRobotics. The array substrate can be, for example, nitrocellulose, plastic, glass, e.g., surface-modified glass. The array can also include a porous matrix, e.g., acrylamide, agarose, or another polymer.

For example, the array can be an array of antibodies, e.g., as described in De Wildt, supra. Cells that produce the protein ligands can be grown on a filter in an arrayed format. Polypeptide production is induced, and the expressed polypeptides are immobilized to the filter at the location of the cell.

A protein array can be contacted with a labeled target to determine the extent of binding of the target to each immobilized polypeptide from the diversity strand library. If the target is unlabeled, a sandwich method can be used, e.g., using a labeled probed, to detect binding of the unlabeled target.

Information about the extent of binding at each address of the array can be stored as a profile, e.g., in a computer database. The protein array can be produced in replicates and used to compare binding profiles, e.g., of a target and a non-target. Thus, protein arrays can be used to identify individual members of the diversity strand library that have desired binding properties with respect to one or more molecules.

FACS. (Fluorescent Activated Cell Sorting). The ET2-ligand can be used to label cells, e.g., cells in a sample (e.g., a patient sample). The ligand is also attached (or attachable) to a fluorescent compound. The cells can then be sorted using fluorescent activated cell sorted (e.g., using a sorter available from Becton Dickinson Immunocytometry Systems, San Jose Calif.; see also U.S. Pat. Nos. 5,627,037; 5,030,002; and 5,137,809). As cells pass through the sorter, a laser beam excites the fluorescent compound while a detector counts cells that pass through and determines whether a fluorescent compound is attached to the cell by detecting fluorescence. The amount of label bound to each cell can be quantified and analyzed to characterize the sample.

The sorter can also deflect the cell and separate cells bound by the ligand from those cells not bound by the ligand. The separated cells can be cultured and/or characterized.

In vivo Imaging. In still another embodiment, the invention provides a method for detecting the presence of a ET2-expressing cancerous tissues in vivo. The method includes (i) administering to a subject (e.g., a patient having a cancer or neoplastic disorder) an anti-ET2 antibody, conjugated to a detectable marker; (ii) exposing the subject to a means for detecting said detectable marker to the ET2- expressing tissues or cells. For example, the subject is imaged, e.g., by NMR or other tomographic means.

Examples of labels useful for diagnostic imaging in accordance with the present invention include radiolabels such as $^{131}I$, $^{111}In$, $^{123}I$, $^{99m}Tc$, $^{32}P$, $^{125}I$, $^{3}H$, $^{14}C$, and $^{188}Rh$, fluorescent labels such as fluorescein and rhodamine, nuclear magnetic resonance active labels, positron emitting isotopes detectable by a positron emission tomography ("PET") scanner, chemiluminescers such as luciferin, and enzymatic markers such as peroxidase or phosphatase. Short-range radiation emitters, such as isotopes detectable by short-range detector probes can also be employed. The protein ligand can be labeled with such reagents using known techniques. For example, see Wensel and Meares (1983) *Radioimmunoimaging and Radioimmunotherapy*, Elsevier, N.Y. for techniques relating to the radiolabeling of antibodies and D. Colcher et al. (1986) *Meth. Enzymol.* 121: 802-816.

A radiolabeled ligand of this invention can also be used for in vitro diagnostic tests. The specific activity of a isotopically-labeled ligand depends upon the half-life, the isotopic purity of the radioactive label, and how the label is incorporated into the antibody.

Procedures for labeling polypeptides with the radioactive isotopes (such as $^{14}C$, $^{3}H$, $^{35}S$, $^{125}I$, $^{32}P$, $^{131}I$) are generally known. For example, tritium labeling procedures are described in U.S. Pat. No. 4,302,438. Iodinating, tritium labeling, and $^{35}S$ labeling procedures, e.g., as adapted for murine monoclonal antibodies, are described, e.g., by Goding, J. W. (*Monoclonal antibodies: principles and practice: production and application of monoclonal antibodies in cell biology, biochemistry, and immunology* 2nd ed. London; Orlando: Academic Press, 1986. pp 124-126) and the references cited therein. Other procedures for iodinating polypeptides, such as antibodies, are described by Hunter and Greenwood (1962) *Nature* 144:945, David et al. (1974) *Biochemistry* 13:1014-1021, and U.S. Pat. Nos. 3,867,517 and 4,376,110. Radiolabeling elements which are useful in imaging include $^{123}I$, $^{131}I$, $^{111}In$, and $^{99m}Tc$, for example. Procedures for iodinating antibodies are described by Greenwood, F. et al. (1963) *Biochem. J.* 89:114-123; Marchalonis, J. (1969) *Biochem. J.* 113:299-305; and Morrison, M. et al. (1971) *Immunochemistry* 289-297. Procedures for $^{99m}Tc$-labeling are described by Rhodes, B. et al. in Burchiel, S. et al. (eds.), *Tumor Imaging: The Radioimmunochemical Detection of Cancer*, New York: Masson 111-123 (1982) and the references cited therein. Procedures suitable for $^{111}$-labeling antibodies are described by Hnatowich, D. J. et al. (1983) *J. Immul. Methods,* 65:147-157, Hnatowich, D. et al. (1984) *J. Applied Radiation,* 35:554-557, and Buckley, R. G. et al. (1984) *F.E.B.S.* 166:202-204.

In the case of a radiolabeled ligand, the ligand is administered to the patient, is localized to the tumor bearing the antigen with which the ligand reacts, and is detected or "imaged" in vivo using known techniques such as radionuclear scanning using e.g., a gamma camera or emission tomography. See e.g., A. R. Bradwell et al., "Developments in Antibody Imaging", *Monoclonal Antibodies for Cancer Detection and Therapy*, R. W. Baldwin et al., (eds.), pp 65-85 (Academic Press 1985). Alternatively, a positron emission transaxial tomography scanner, such as designated Pet VI located at Brookhaven National Laboratory, can be used where the radiolabel emits positrons (e.g., $^{11}C$, $^{18}F$, $^{15}O$, and $^{13}N$).

MRI Contrast Agents. Magnetic Resonance Imaging (MRI) uses NMR to visualize internal features of living subject, and is useful for prognosis, diagnosis, treatment, and surgery. MRI can be used without radioactive tracer compounds for obvious benefit. Some MRI techniques are summarized in EP-A-0 502 814. Generally, the differences related to relaxation time constants T1 and T2 of water protons in different environments is used to generate an image. However, these differences can be insufficient to provide sharp high resolution images.

The differences in these relaxation time constants can be enhanced by contrast agents. Examples of such contrast agents include a number of magnetic agents paramagnetic agents (which primarily alter T1) and ferromagnetic or superparamagnetic (which primarily alter T2 response). Chelates (e.g., EDTA, DTPA and NTA chelates) can be used to attach (and reduce toxicity) of some paramagnetic substances (e.g., $Fe^{+3}$, $Mn^{+2}$, $Gd^{+3}$). Other agents can be in the form of particles, e.g., less than 10 μm to about 10 nM in diameter). Particles can have ferromagnetic, antiferromagnetic or superparamagnetic properties. Particles can include, e.g., magnetite ($Fe_3O_4$), γ-$Fe_2O_3$, ferrites, and other magnetic mineral compounds of transition elements. Magnetic particles may include: one or more magnetic crystals with and without nonmagnetic material. The nonmagnetic material can include synthetic or natural polymers (such as sepharose, dextran, dextrin, starch and the like.

The ET2-ligands can also be labeled with an indicating group containing of the NMR-active $^{19}F$ atom, or a plurality of such atoms inasmuch as (i) substantially all of naturally abundant fluorine atoms are the $^{19}F$ isotope and, thus, substantially all fluorine-containing compounds are NMR-active; (ii) many chemically active polyfluorinated compounds such as trifluoracetic anhydride are commercially available at relatively low cost, and (iii) many fluorinated compounds have been found medically acceptable for use in humans such as the perfluorinated polyethers utilized to carry oxygen as hemoglobin replacements. After permitting such time for incubation, a whole body MRI is carried out using an apparatus such as one of those described by Pykett (1982) *Scientific American,* 246:78-88 to locate and image cancerous tissues.

Also within the scope of the invention are kits comprising the protein ligand that binds to ET2 and instructions for diagnostic use, e.g., the use of the ET2-ligand (e.g., antibody or antigen-binding fragment thereof, or other polypeptide or peptide) to detect ET2, in vitro, e.g., in a sample, e.g., a biopsy or cells from a patient having a cancer or neoplastic disorder, or in vivo, e.g., by imaging a subject. The kit can further contain a least one additional reagent, such as a label or additional diagnostic agent. For in vivo use the ligand can be formulated as a pharmaceutical composition.

The following invention is further illustrated by the following examples, which should not be construed as further limiting. The contents of all references, pending patent applications and published patents, cited throughout this application are hereby expressly incorporated by reference.

EXAMPLE 1

Selection and Primary Screening

In order to isolate antibodies that bind ET2, a phagemid Fab library was screened against the protease domain of ET2.

The biotinylated protease domain of ET2 was captured on streptavidin coated magnetic beads (M280-DYNAL). The ET2 coated beads were washed three times with 2% non-fat milk in PBS prior to addition of library phage. Library phage ($10^{12}$ particles) were added to the magnetic beads in a final volume of 100 μl. The mix was allowed to incubate at room temperature with end over end mixing for two hours. After this time, the supernatant was removed and the beads washed three times with 0.1% Tween 2% non-fat milk in PBS. After the final wash, the beads were transferred to a new tube. Phage were eluted from the beads by addition of 1 ml of 100 mM Triethanolamine buffer (TEA). After a 10 min incubation at room temperature the supernatant was removed and added to 500 μl of Tris-HCl pH 7.5. The eluted phage were then amplified and used for a further round of selection. After three rounds of selection the output was analyzed as described below. (For methods, see also Chames et al. (2002) *Methods Mol. Biol.* 178:147-57).

Library members recovered from the selections were tested for ET2 binding by phage ELISA (FIG. 3). Each isolate was tested for binding to ET2, and a blank streptavidin well. Isolates that gave an ELISA signal for ET2 twice that for streptavidin binding were considered 'positives' and selected for small scale soluble Fab production. A total of 184 isolates were tested in the phage ELISA, of which 171 tested positive for ET-2 binding, according to this method. Exemplary data is provided in Table 4 below:

TABLE 4

Exemplary Phage ELISA data

| BSA-Strept-rET2 | BSA-STrept |
|---|---|
| 0.342 | 0.120 |
| 0.323 | 0.090 |
| 0.320 | 0.086 |
| 0.278 | 0.082 |
| 0.261 | 0.090 |
| 0.280 | 0.086 |
| 0.247 | 0.091 |
| 0.244 | 0.088 |
| 0.263 | 0.131 |
| 0.264 | 0.102 |
| 0.172 | 0.087 |
| 0.223 | 0.088 |
| 0.200 | 0.100 |
| 0.272 | 0.083 |
| 0.263 | 0.087 |
| 0.233 | 0.097 |
| 0.158 | 0.129 |
| 0.490 | 0.111 |
| 0.225 | 0.092 |
| 0.191 | 0.092 |
| 0.193 | 0.113 |
| 0.210 | 0.089 |
| 0.186 | 0.103 |
| 0.259 | 0.098 |
| 0.198 | 0.143 |
| 0.177 | 0.116 |
| 0.197 | 0.097 |
| 0.173 | 0.094 |

TABLE 4-continued

Exemplary Phage ELISA data

| BSA-Strept-rET2 | BSA-STrept |
|---|---|
| 0.198 | 0.148 |
| 0.202 | 0.102 |
| 0.270 | 0.108 |
| 0.204 | 0.095 |
| 0.189 | 0.164 |
| 0.202 | 0.128 |
| 0.163 | 0.110 |
| 0.188 | 0.106 |
| 0.199 | 0.122 |
| 0.187 | 0.109 |
| 0.246 | 0.120 |
| 0.215 | 0.102 |
| 0.178 | 0.162 |
| 0.169 | 0.158 |
| 0.189 | 0.114 |
| 0.210 | 0.125 |
| 0.192 | 0.134 |
| 0.182 | 0.151 |
| 0.251 | 0.115 |
| 0.185 | 0.114 |

EXAMPLE 2

Fab Production and Screening

Small scale amounts of soluble Fab were produced in a 96-well format and tested for binding to ET2. To help further characterize the Fabs, the ELISA was performed in the presence and absence of a competing ligand that binds to the active site of ET2. When the Fab ELISA signal is reduced in the presence of the competing ligand, it is likely that these Fabs bind at or close to the active site. Exemplary data is provided in Table 5 below:

TABLE 5

Exemplary Soluble Fab ELISA data

| | Soluble Fab + rET pept. Inhib. | Soluable Fab − rET pept. Inhib. |
|---|---|---|
| A1 | 0.21 | 0.31 |
| B1 | 0.89 | 0.947 |
| C1 | 0.135 | 0.143 |
| D1 | 0.267 | 0.351 |
| E1 | 0.118 | 0.204 |
| F1 | 0.124 | 0.239 |
| G1 | 0.22 | 0.392 |
| H1 | 0.271 | 0.472 |
| A2 | 0.872 | 0.992 |
| B2 | 0.172 | 0.23 |
| C2 | 0.154 | 0.191 |
| D2 | 0.611 | 0.599 |
| E2 | 0.128 | 0.205 |
| F2 | 0.872 | 1.248 |
| G2 | 0.126 | 0.192 |
| H2 | 0.128 | 0.232 |
| A3 | 0.241 | 0.435 |
| B3 | 0.132 | 0.168 |
| C3 | 0.114 | 0.145 |
| D3 | 0.822 | 0.83 |
| E3 | 0.118 | 0.143 |
| F3 | 0.224 | 0.388 |
| G3 | 0.332 | 0.591 |
| H3 | 0.173 | 0.304 |
| A4 | 0.168 | 0.167 |

TABLE 5-continued

| Exemplary Soluble Fab ELISA data | | |
|---|---|---|
| | Soluble Fab + rET pept. Inhib. | Soluable Fab − rET pept. Inhib. |
| B4 | 0.173 | 0.229 |
| C4 | 0.112 | 0.155 |
| D4 | 0.134 | 0.172 |
| E4 | 0.119 | 0.168 |
| F4 | 0.138 | 0.189 |

TABLE 5-continued

| Exemplary Soluble Fab ELISA data | | |
|---|---|---|
| | Soluble Fab + rET pept. Inhib. | Soluable Fab − rET pept. Inhib. |
| G4 | 0.652 | 0.735 |
| H4 | 0.321 | 0.42 |
| A5 | 0.182 | 0.26 |
| B5 | 0.184 | 0.325 |
| C5 | 0.236 | 0.419 |
| D5 | 0.958 | 0.758 |
| E5 | 0.154 | 0.169 |
| F5 | 0.127 | 0.219 |
| G5 | 0.315 | 0.322 |
| H5 | 0.225 | 0.277 |
| A6 | 0.133 | 0.128 |
| B6 | 0.155 | 0.146 |
| C6 | 1.091 | 1.063 |
| D6 | 0.122 | 0.163 |
| E6 | 0.137 | 0.15 |
| F6 | 0.186 | 0.224 |

A total of 64 soluble Fabs were identified that bound ET2 in this assay. Of these, 31 were strongly competed by the peptide, a further 8 showed weak competition in the presence of the peptide. We found that competition of the Fab binding to the target enzyme by a peptide inhibitor was a useful method to identify inhibitors. This was done by examining the inhibition by the Fabs by another type of assay. Soluble Fabs that bound ET2 were prepared on a large scale (450 ml cultures) and used to determine inhibition of ET2 in a continuous in vitro enzyme assay.

An assay for evaluating inhibitors of ET2 can be performed as follows: Test compounds for inhibition of the protease activity of the protease domain of ET2 are assayed in Costar 96 well tissue culture plates (Corning N.Y.). Approximately 2-3 nM ET2 is mixed with varying concentrations of inhibitor in 29.2 mM Tris, pH 8.4, 29.2 mM imidazole, 217 mM NaCl (100 mL final volume), and allowed to incubate at room temperature for 30 minutes. 400 mM substrate S 2765 (DiaPharma, Westchester, Ohio) is added, and the reaction is monitored in a SpectraMAX Plus microplate reader (Molecular Devices, Sunnyvale Calif.) by following the change in absorbance at 405 nm for 1 hour at 37° C. All reagents unless indicated were obtained from Sigma Chemical Co. (St. Louis, Mo.). Additional details can be in accordance with the ET1 assay provided further below.

An exemplary structure of S 2765 is:

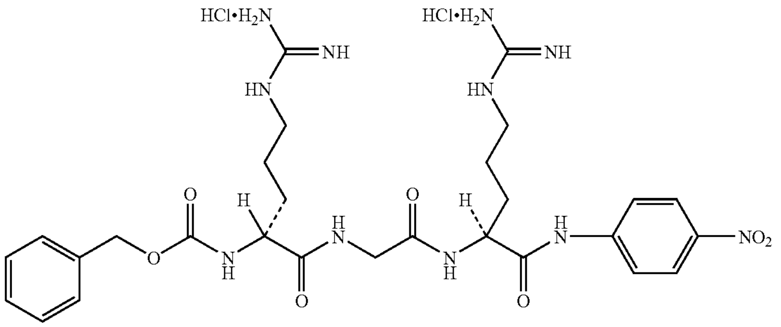

We showed that those Fabs that show strong competition by the peptide are good enzyme inhibitors of ET2. The Ki values for the best inhibitors are shown in Table 6. These clones were subsequently sequenced.

TABLE 6

| Inhibition Data for Fab Inhibitors | | | |
|---|---|---|---|
| Clone | Coding | Library | Ki |
| D5: | R3 rET2 MP3 | CJ Phagemid | 70 ± 10 pM |
| D2: | R3 rET2 MP1 | CJ Phagemid | 90 ± 30 pM |
| A2: | R3 rET2 MP1 | CJ Phagemid | 160 ± 50 pM |
| H10: | R3 rET2 MP1 | CJ Phagemid | 190 ± 10 pM |
| F8: | R3 rET2 MP1 | CJ Phagemid | 240 ± 20 pM |
| B5: | R3 rET2 MP3 | CJ Phagemid | 250 ± 60 pM |
| C9: | R3 rET2 MP3 | CJ Phagemid | 260 ± 50 pM |

The following is an assay for ET1 activity. The assay buffer for assaying ET1 activity was HBSA (10 mM Hepes, 150 mM sodium chloride, pH 7.4, 0.1% bovine serum albumin). All reagents were from Sigma Chemical Co. (St. Louis, Mo.), unless otherwise indicated. Two $IC_{50}$ assays at 30-minute (a 30-minute preincubation of test Fab and enzyme) and at 0-minutes (no preincubation of test Fab and enzyme) were conducted. For the $IC_{50}$ assay at 30-minute, the following reagents were combined in appropriate wells of a Corning microtiter plate: 50 microliters of HBSA, 50 microliters of the test compound, diluted (covering a broad concentration range) in HBSA (or HBSA alone for uninhibited velocity measurement), and 50 microliters of the rET1 (Corvas International) diluted in buffer, yielding a final enzyme concentration of 250 pM. Following a 30-minute incubation at ambient temperature, the assay was initiated by the addition of 50 microliters of the substrate Spectrozyme tPA (Methylsulfonyl-D-cyclohexyltyrosyl-L-glycyl-L-arginine-p-nitroaniline acetate, obtained from American Diagnostica, Inc. (Greenwich, Conn.) and reconstituted in deionized water, followed by dilution in HBSA prior to the assay) were added to the wells, yielding a final volume of 200 microliters and a final substrate concentration of 300 μM (about 1.5-times Km).

For the $IC_{50}$ assay at 0-minute, the same reagents were combined: 50 microliters of HBSA, 50 microliters of the test compound, diluted (covering the identical concentration range) in HBSA (or HBSA alone for uninhibited velocity measurement), and 50 microliters of the substrate Spectrozyme tPA. The assay was initiated by the addition of 50 microliters of rET2. The final concentrations of all components were identical in both $IC_{50}$ assays (at 30- and 0-minute incubations).

The initial velocity of chromogenic substrate hydrolysis was measured in both assays by the change of absorbance at 405 nM using a Thermo Max Kinetic Microplate Reader (Molecular Devices) over a 5 minute period, in which less than 5% of the added substrate was used. The concentration of added inhibitor, which caused a 50% decrease in the initial rate of hydrolysis was defined as the respective $IC_{50}$ value in each of the two assays (30- and 0-minute).

EXAMPLE 3

Selectivity of Fab Inhibitors

The sequence data for the Fab inhibitors is shown in Table 1 (above, in the Summary section). Four clones (A2, B5, D2 & H10) share the same heavy chain sequence. This sequence contains a lysine to amber stop codon mutation. Although one would normally expect such a mutation to result in truncation of the heavy chain, and consequently result in a non-functional Fab, all propagations were performed in a supE mutant of *E. coli*. This mutant strain inserts a glutamine residue, shown as q in the sequence data, at the amber stop codon thus allowing production of the mature Fab.

The seven Fabs described above were reformatted into IgG1 antibodies. Fab reformatting is a two step process in which the Fab is first cloned into the IgG1 expression vector (pRRV) which provides a eukaryotic promoter to drive expression of the heavy and light chains and the heavy chain constant sequence. In the second step, the *E. coli* promoter used to drive expression of the heavy chain is replaced with a eukaryotic internal ribosome entry sequence (IRES). To allow expression in the mammalian system the four clones that had amber stop mutations, A2, B5, D2 & H10, had the amber mutation replaced with a lysine, the naturally occurring amino acid at this position.

Once expression vector construction was complete the antibodies were transiently expressed in HEK 293T cells and subsequently purified from the cell culture media using protein A affinity chromatography. The purified antibody was tested in the same continuous in vitro assay previously used for analysis of the Fabs. The Ki values are shown in Table 7.

In a selectivity screen all IgG's demonstrated <5% activity at 100 nM against proteases Trypsinogen-IV, MTSP-1, MTSP-6, MTSP-7, MTSP-10 and ET1.

TABLE 7

Comparison of Inhibition Data for Fab & IgG Inhibitors

| Clone | Target | Ki (Fab) | Ki (IgG) |
|---|---|---|---|
| D5 | rET2 | 70 pM | 86 pM |
| D2 | rET2 | 95 pM | 44 pM |
| A2 | rET2 | 150 pM | 53 pM |
| H10 | rET2 | 315 pM | 136 pM |
| F8 | rET2 | 410 pM | 840 pM |
| B5 | rET2 | 325 pM | 102 pM |
| C9 | rET2 | 310 pM | 110 pM |

EXAMPLE 4

Reduction in Tumor Growth

One antibody that binds to ET-2 was evaluated in a small animal efficacy study.

DU-145 tumor cells injected subcutaneously into the animal's flank 6-8 week old SCID mice (Charles River). Five to 10 days after tumor implantation the animals were randomized into groups of 10-15 animals. Treatment was by IP injection, either once a day with Fab (0, 200 or 400 μg/animal), or once every other day with IgG (0, 10, 50 or 500 μg/animal). The study was allowed to continue until the tumors reached the maximal allowable size. Tumor sizes were measured vernier calipers (Mitutoyo Model 573) and tumor volumes calculated. At the end of the study tumors were excised and weighed. Animal health was assessed during the study by regular weighing. Treatment with 400 μg of Fab H10 reduced the rate of tumor growth relative to the rate in animals given the control treatments. For example, 35 days after the first dose, average tumor volumes (FIG. 3A) and tumor weights (FIG. 3B) were reduced for animals treated with 400 μg of Fab H10. Other useful antibodies can similarly reduce tumor growth, e.g., reduce tumor weight by at least 10, 20, 30, 40, 50% relative to a control, e.g., after 35 days.

EXAMPLE 5

Exemplary Sequences—A10

```
Translation of A10 HC (1-344)
  1 EVQLLESGGG LVQPGGSLRL SCAASGFTFS RYRMWWVRQA PGKGLEWVSY          (SEQ ID NO:25)

 51 ISSSGGFTNY ADSVKGRFTI SRDNSKNTLY LQMNSLRAED TAVYYCAKNA

101 RPALPSMDVW GKGT

Translation of A10 LC (1-354)
  1 QSALTQPPSA SGTPGQRVTI SCSGSSSNIG SNYVYWYQQL PGTAPKLLIY          (SEQ ID NO:26)

 51 SNNQRPSGVP DRFSGSKSGT SASLAISGLR SEDEADYYCA AWDDSLSGPV

101 FGGGTKLTVL GQPKAAPS
```

-continued

A10 HC Nucleic Acid Sequence
GAAGTTCAATTGTTAGAGTCTGGTGGCGGTCTTGTTCAGCCTGGTGGTTCTTTACGTCTTTCTTGCGCTG   (SEQ ID NO:27)

CTTCCGGATTCACTTTCTCTCGTTACCGTATGTGGTGGGTTCGCCAAGCTCCTGGTAAAGGTTTGGAGTG

GGTTTCTTATATCTCTTCTTCTGGTGGCTTTACTAATTATGCTGACTCCGTTAAAGGTCGCTTCACTATC

TCTAGAGACAACTCTAAGAATACTCTCTACTTGCAGATGAACAGCTTAAGGGCTGAGGACACTGCAGTCT

ACTATTGTGCGAAAAACGCGCGAAGAGCTCTTCCCTCCATGGACGTCTGGGGCAAAGGGACCAC

A10 LC Nucleic Acid Sequence
CAGAGCGCTTTGACTCAGCCACCCTCAGCGTCTGGGACCCCCGGGCAGAGGGTCACCATCTCTTGTTCTG   (SEQ ID NO:28)

GAAGCAGCTCCAACATCGGAAGTAATTATGTATACTGGTACCAGCAGCTCCCAGGAACGGCCCCCAAACT

CCTCATCTATAGTAATAATCAGCGGCCCTCAGGGGTCCCTGACCGATTCTCTGGCTCCAAGTCTGGCACC

TCAGCCTCCCTGGCCATCAGTGGGCTCCGGTCCGAGGATGAGGCTGATTATTACTGTGCAGCATGGGATG

ACAGCCTGAGTGGTCCGGTGTTCGGCGGAGGGACCAAGCTGACCGTCCTAGGTCAGCCCAAGGCTGCCCC

CTCG

EXAMPLE 6

Exemplary Sequences—G3

```
Translation of G3 HC (1-342)
  1 EVQLLESGGG LVQPGGSLRL SCAASGFTFS RYGMSWVRQA PGKGLEWVSV             (SEQ ID NO:29)

 51 IYSSGGITRY ADSVKGRFTI SRDNSKNTLY LQMNSLRAED TAVYYCARRA

101 PRGEVAFDIW GQGT

Translation of G3 LC (1-345)
  1 QDIQMTQSPS FLSASIGDRV TITCWASQGI SNYLAWYQQK PGKAPKLLIS             (SEQ ID NO:30)

 51 SASTLQSGVP SRFSGSGSGT EFTLTISSLQ PEDSATYYCQ QANSFPWTFG

101 QGTRVEIRRT VAAPS
```

G3 HC Nucleic Acid Sequence
GAAGTTCAATTGTTAGAGTCTGGTGGCGGTCTTGTTCAGCCTGGTGGTTCTTTACGTCTTTCTTGCGCTG   (SEQ ID NO:31)

CTTCCGGATTCACTTTCTCTCGTTACGGTATGTCTTGGGTTCGCCAAGCTCCTGGTAAAGGTTTGGAGTG

GGTTTCTGTTATCTATTCTTCTGGTGGCATTACTCGTTATGCTGACTCCGTTAAAGGTCGCTTCACTATC

TCTAGAGACAACTCTAAGAATACTCTCTACTTGCAGATGAACAGCTTAAGGGCTGAGGACACTGCAGTCT

ACTACTGTGCGAGACGGGCCCCGAGGGGGGAGGTCGCTTTTGATATCTGGGGCCAAGGGACA

G3 LC Nucleic Acid Sequence
CAAGACATCCAGATGACCCAGTCTCCATCCTTCCTGTCTGCATCTATAGGAGACAGAGTCACCATCACTT   (SEQ ID NO:32)

GCTGGGCCAGTCAGGGCATTAGTAATTATTTAGCCTGGTATCAGCAAAAACCAGGGAAAGCCCCTAAGCT

CCTGATCTCTTCTGCATCCACTTTGCAAAGTGGGGTCCCATCAAGGTTCAGCGGCAGTGGATCTGGGACA

GAATTCACTCTCACAATCAGCAGCCTGCAGCCTGAAGATTCTGCAACTTACTATTGTCAACAGGCTAACA

GTTTCCCGTGGACGTTCGGCCAAGGGACCAGGGTGGAAATCAGACGAACTGTGGCTGCACCATCT

EXAMPLE 7

Exemplary Sequences—A6

```
Translation of A6 HC (1-344)
  1 EVQLLESGGG LVQPGGSLRL SCAASGFTFS RYKMWWVRQA PGKGLEWVSY             (SEQ ID NO:33)

 51 ISPSGGYTGY ADSVKGRFTI SRDNSKNTLY LQMNSLRAED TAVYYCAKNA

101 RRAFPSMDVW GKGT
```

-continued

Translation of A6 LC (1-345)
1QSALTQDPAV SVALGQTVRI TCRGDRLRSY YSSWYQQKPR QAPVLVMFGR (SEQ ID NO:34)

51NNRPSGIPDR FSGSTSGSTA SLTITATQAD DEADYFCSSR DGSGNFLFGG

101GTKLTVLGQP KAAPS

A6 HC Nucleic Acid Sequence
GAAGTTCAATTGTTAGAGTCTGGTGGCGGTCTTGTTCAGCCTGGTGGTTCTTTACGTCTTTCTTGCGCTG (SEQ ID NO:35)

CTTCCGGATTCACTTTCTCTCGTTACAAGATGTGGTGGGTTCGCCAAGCTCCTGGTAAAGGTTTGGAGTG

GGTTTCTTATATCTCTCCTTCTGGTGGCTATACTGGTTATGCTGACTCCGTTAAAGGTCGCTTCACTATC

TCTAGAGACAACTCTAAGAATACTCTCTACTTGCAGATGAACAGCTTAAGGGCTGAGGACACTGCAGTCT

ACTATTGTGCGAAAAACGCGCGAAGAGCTTTTCCCTCCATGGACGTCTGGGGCAAAGGGACCAC

A6 LC Nucleic Acid Sequence
CAGAGCGCTTTGACTCAGGACCCTGCTGTGTCTGTGGCCTTGGGGCAGACAGTCAGGATCACATGCCGAG (SEQ ID NO:36)

GAGACAGACTCAGAAGTTATTATTCAAGTTGGTACCAGCAGAAGCCACGACAGGCCCCTGTTCTTGTCAT

GTTTGGTAGAAACAACCGGCCCTCAGGGATCCCAGACCGATTCTCTGGCTCCACCTCAGGAAGCACAGCT

TCCTTGACCATCACTGCGACTCAGGCGGACGATGAGGCTGACTATTTCTGTAGTTCCCGGGACGGCAGTG

GTAATTTCCTCTTCGGCGGAGGGACCAAACTGACCGTCCTTGGTCAGCCCAAGGCTGCCCCCTCG

EXAMPLE 8

Exemplary Sequences—A7

Translation of A7 HC (1-342)
1EVQLLESGGG LVQPGGSLRL SCAASGFTFS RYRMSWVRQA PGKGLEWVSS (SEQ ID NO:37)

51ISSSGGITTY ADSVKGRFTI SRDNSKNTLY LQMNSLRAED AAIYYCAKNA

101RRAFPSMDVW GKGT

Translation of A7 LC (1-348)
1QDIQMTQSPS SLSASVGDRV TITCRASQSI SSYLNWYQQK PGKAPKLLIY (SEQ ID NO:38)

51AASSLQSGVP SRFSGSGSGT EFTLTINSLQ PEDFATYYCQ QLTGYPSITF

101GQGTRLDIKR TVAAPS

A7 HC Nucleic Acid Sequence
GAAGTTCAATTGTTAGAGTCTGGTGGCGGTCTTGTTCAGCCTGGTGGTTCTTTACGTCTTTCTTGCGCTG (SEQ ID NO:39)

CTTCCGGATTCACTTTCTCTCGTTACCGTATGTCTTGGGTTCGCCAAGCTCCTGGTAAAGGTTTGGAGTG

GGTTTCTTCTATCTCTTCTTCTGGTGGCATTACTACTTATGCTGACTCCGTTAAAGGTCGCTTCACTATC

TCTAGAGACAACTCTAAGAATACTCTCTACTTGCAGATGAACAGCTTAAGGGCTGAGGACGCTGCAATCT

ACTATTGTGCGAAAAACGCGCGAAGAGCTTTTCCCTCCATGGACGTCTGGGGCAAAGGGACC

A7 LC Nucleic Acid Sequence
CAAGACATCCAGATGACCCAGTCTCCATCCTCCCTGTCTGCATCTGTAGGAGACAGAGTCACCATCACTT (SEQ ID NO:40)

GCCGGGCAAGTCAGAGCATTAGCAGCTATTTAAATTGGTATCAGCAGAAACCAGGGAAAGCCCCTAAGCT

CCTGATCTATGCTGCATCCAGTTTGCAAAGTGGGGTCCCATCAAGGTTCAGCGGCAGTGGATCTGGGACA

GAATTCACTCTCACAATCAACAGCCTGCAGCCTGAAGATTTTGCAACTTATTACTGTCAACAACTTACTG

GTTACCCCTCGATCACCTTCGGCCAAGGGACACGACTGGACATTAAACGAACTGTGGCTGCACCATCT

EXAMPLE 9

Exemplary Sequences—C8

Translation of C8 HC (1-342)
1 EVQLLESGGG LVQPGGSLRL SCAASGFTFS RYTMSWVRQA PGKGLEWVSY (SEQ ID NO:41)

51 IVPSGGMTKY ADSVKGRFTI SRDNSKNTLY LQMNSLRAED TAVYYCARRA

101 PRGEVAFDIW GQGT

Translation of C8 LC (1-354)
1 QSVLTQPASV SGSPGQSITI SCTGTSSDVG GYNYVSWYQQ HPGKAPKLMI (SEQ ID NO:42)

51 YDVSKRPSGV SNRFSGSKSG NTASLTISGL QAEDEADYYC TSYTSSSTWV

101 FGGGTKLTVL GQPKAAPS

C8 HC Nucleic Acid Sequence
GAAGTTCAATTGTTAGAGTCTGGTGGCGGTCTTGTTCAGCCTGGTGGTTCTTTACGTCTTTCTTGCGCTG (SEQ ID NO:43)

CTTCCGGATTCACTTTCTCTCGTTACACTATGTCTTGGGTTCGCCAAGCTCCTGGTAAAGGTTTGGAGTG

GGTTTCTTATATCGTTCCTTCTGGTGGCATGACTAAGTATGCTGACTCCGTTAAAGGTCGCTTCACTATC

TCTAGAGACAACTCTAAGAATACTCTCTACTTGCAGATGAACAGCTTAAGGGCTGAGGACACTGCAGTCT

ACTATTGTGCGAGACGGGCCCCGAGGGGGGAGGTCGCTTTTGATATCTGGGGCCAAGGGACA

C8 LC Nucleic Acid Sequence
CAGAGCGTCTTGACTCAGCCTGCCTCCGTGTCTGGGTCTCCTGGACAGTCGATCACCATCTCCTGCACTG (SEQ ID NO:44)

GAACCAGCAGTGACGTTGGTGGTTATAACTATGTCTCCTGGTACCAACAGCACCCAGGCAAAGCCCCCAA

ACTCATGATTTATGATGTCAGTAAGCGGCCCTCAGGGGTTTCTAATCGCTTCTCTGGCTCCAAGTCTGGC

AACACGGCCTCCCTGACCATCTCTGGGCTCCAGGCTGAGGACGAGGCTGATTATTACTGCACCTCATATA

CAAGTAGCAGCACTTGGGTGTTCGGCGGAGGGACCAAGCTGACCGTCCTAGGTCAGCCCAAGGCTGCCCC

CTCG

EXAMPLE 10

Exemplary Sequences—H9

Translation of H9 HC (1-344)
1 EVQLLESGGG LVQPGGSLRL SCAASGFTFS RYSMHWVRQA PGKGLEWVSS (SEQ ID NO:45)

51 IGPSGGKTKY ADSVKGRFTI SRDNSKNTLY LQMNSLRAED TAVYYCARPF

101 RGSYYYFDYW GQGT

Translation of H9 LC (1-345)
1 QDIQMTQSPS SLSASIGDRV TITCQASQDT YNRLHWYQQK SGKAPKLLIY (SEQ ID NO:46)

51 DAVNLKRGVP SRFRGSGSGT NFILTITNLQ PEDTATYFCQ HSDDLSLAFG

101 GGTKVEIKRT VAAPS

H9 HC Nucleic Acid Sequence
GAAGTTCAATTGTTAGAGTCTGGTGGCGGTCTTGTTCAGCCTGGTGGTTCTTTACGTCTTTCTTGCGCTG (SEQ ID NO:47)

CTTCCGGATTCACTTTCTCTCGTTACTCTATGCATTGGGTTCGCCAAGCTCCTGGTAAAGGTTTGGAGTG

GGTTTCTTCTATCGGTCCTTCTGGTGGCAAGACTAAGTATGCTGACTCCGTTAAAGGTCGCTTCACTATC

TCTAGAGACAACTCTAAGAATACTCTCTACTTGCAGATGAACAGCTTAAGGGCTGAGGACACTGCAGTCT

ACTATTGTGCGAGACCCTTCCGTGGGAGCTACTACTACTTTGACTACTGGGGCCAGGGAACCCT

H9 LC Nucleic Acid Sequence
CAAGACATCCAGATGACCCAGTCTCCATCCTCCCTGTCTGCATCTATAGGAGACAGAGTCACCATAACTT (SEQ ID NO:48)

GCCAGGCGAGTCAGGACACTTACAACCGTCTACATTGGTATCAGCAGAAATCAGGGAAAGCCCCTAAACT

-continued

CCTCATCTACGATGCAGTCAATTTGAAAAGGGGGGTCCCTTCAAGGTTCCGTGGAAGTGGATCTGGGACA

AATTTTATTTTGACCATCACCAACCTGCAGCCTGAAGATACTGCAACATATTTCTGTCAACATTCTGATG

ATCTGTCACTCGCTTTCGGCGGAGGGACCAAGGTGGAGATCAAACGAACTGTGGCTGCACCATCT

EXAMPLE 11

Exemplary Sequences—G10-R2

Translation of G10-R2 HC (1-382)
1 EVQLLESGGG LVQPGGSLRL SCAASGFTFS RYKMWWVRQA PGKGLEWVSY (SEQ ID NO:49)

51 ISPSGGYTGY ADSVKGRFTI SRDNSKNTLY LQMNSLRAED TAVYYCAKNA

101 RRAFPSMDVW GKGTTVTVSS ASTKGPS

Translation of G10-APSR2 LC (1-360)
1 QDIQMTQSPL SLPVTPGEPA SISCRSSQSL LYSNGYNYLD WYLQRPGQSP (SEQ ID NO:50)

51 QLLIYLGSNR ASGVPDRFSG SGSGTDFTLK ISRVEAKDVG VYYCMQALQI

101 PRTFGQGTKV EIKRTVAAPS

G1 HC Coding Sequence0-R2
GAAGTTCAATTGTTAGAGTCTGGTGGCGGTCTTGTTCAGCCTGGTGGTTCTTTACGTCTTTCTTGCGCTGCTTCCGG (SEQ ID NO:51)

ATTCACTTTCTCTCGTTACAAGATGTGGTGGGTTCGCCAAGCTCCTGGTAAAGGTTTGGAGTGGGTTTCTTATATCT

CTCCTTCTGGTGGCTATACTGGTTATGCTGACTCCGTTAAAGGTCGCTTCACTATCTCTAGAGACAACTCTAAGAAT

ACTCTCTACTTGCAGATGAACAGCTTAAGGGCTGAGGACACTGCAGTCTACTATTGTGCGAAAAACGCGCGAAGAGC

TTTTCCCTCCATGGACGTCTGGGGCAAAGGGACCACGGTCACCGTCTCAAGCGCCTCCACCAAGGGCCCATCGG

G1 LC Coding Sequence0-R2
CAAGACATCCAGATGACCCAGTCTCCACTCTCCCTGCCCGTCACCCCTGGAGAGCCGGCCTCCATCTCCTGCAGGTC (SEQ ID NO:52)

TAGTCAGAGCCTCCTGTATAGTAATGGATACAACTATTTGGATTGGTACCTGCAGAGACCAGGGCAGTCTCCACAGC

TCCTGATCTATTTGGGTTCTAATCGGGCCTCCGGGGTCCCTGACAGGTTCAGTGGCAGTGGATCAGGCACAGATTTC

ACACTGAAAATCAGCAGAGTGGAGGCTAAGGATGTTGGGGTTTATTACTGCATGCAAGCTCTACAAATTCCTCGGAC

GTTCGGCCAAGGGACCAAGGTGGAAATCAAACGAACTGTGGCTGCACCATCT

EXAMPLE 12

Exemplary Sequences—F3-R2

Translation of F3-R2 HC (1-382)
1 EVQLLESGGG LVQPGGSLRL SCAASGFTFS RYRMHWVRQA PGKGLEWVSG (SEQ ID NO:53)

51 ISSSGGDTNY ADSVKGRFTI SRDNSKNTLY LQMNSLRAED TAVYYCAKNA

101 RRAFPSMDVW GKGTTVTVSS ASTKGPS

Translation of F3-R2 LC (1-345)
1 QDIQMTQSPS SVSASVGDTV TITCRASLPV NTWLAWYQQK PGKAPKLLLY (SEQ ID NO:54)

51 AASRLQSGVP SRFSGSGSGT DFTLNISSLQ PEDFATYYCQ QANTFPYTFG

101 QGTKVDIKRT VAAPS

F3 HC Coding Sequence-R2
GAAGTTCAATTGTTAGAGTCTGGTGGCGGTCTTGTTCAGCCTGGTGGTTCTTTACGTCTTTCTTGCGCTG (SEQ ID NO:55)

CTTCCGGATTCACTTTCTCTCGTTACCGTATGCATTGGGTTCGCCAAGCTCCTGGTAAAGGTTTGGAGTG

GGTTTCTGGTATCTCTTCTTCTGGTGGCGATACTAATTATGCTGACTCCGTTAAAGGTCGCTTCACTATC

-continued

TCTAGAGACAACTCTAAGAATACTCTCTACTTGCAGATGAACAGCTTAAGGGCTGAGGACACTGCAGTCT

ACTATTGTGCGAAAAACGCGCGAAGAGCTTTTCCCTCCATGGACGTCTGGGGCAAAGGGACCACGGTCAC

CGTCTCAAGCGCCTCCACCAAGGGCCCATCGG

F3 LC Coding Sequence-R2

CAAGACATCCAGATGACCCAGTCTCCATCTTCCGTGTCTGCATCTGTAGGAGACACAGTCACCATCACTT (SEQ ID NO:56)

GTCGGGCGAGTCTGCCTGTTAACACCTGGTTAGCCTGGTATCAGCAGAAACCCGGGAAAGCCCCTAAACT

CCTGCTCTATGCTGCATCCAGATTACAAAGTGGGGTCCCATCAAGGTTCAGCGGCAGTGGCTCTGGGACA

GATTTCACTCTCAACATCAGCAGTCTGCAGCCTGAGGATTTTGCAACCTACTATTGTCAACAGGCGAACA

CTTTCCCGTACACTTTTGGCCAGGGGACCAAAGTGGATATCAAACGAACTGTGGCTGCACCATCT

EXAMPLE 13

Exemplary Sequences—C6-R2

Translation of C6-R2 HC (1-382)

1 EVQLLESGGG LVQPGGSLRL SCAASGFTFS RYSMHWVRQA PGKGLEWVSR (SEQ ID NO:57)

51 IVPSGGTTFY ADSVKGRFTI SRDNSKNTLY LQMNSLRAED TAVYYCAKNA

101 RRAFPSMDVW GKGTTVTVSS ASTKGPS

Translation of C6-R2 LC (1-348)

1 QSALTQDPAV SVALGQTVRI TCQGDSLRSY YASWYQQKPG QAPVLVIYSK (SEQ ID NO:58)

51 SNRPSGIPDR FSGSSSGSTA SLTITGAQAE DEADYYCNSR DSSGNHLVFG

101 GGTKLTVLGQ PKAAPS

C6 HC Coding Sequence-R

GAAGTTCAATTGTTAGAGTCTGGTGGCGGTCTTGTTCAGCCTGGTGGTTCTTTACGTCTTTCTTGCGCTG (SEQ ID NO:59)

CTTCCGGATTCACTTTCTCTCGTTACTCTATGCATTGGGTTCGCCAAGCTCCTGGTAAAGGTTTGGAGTG

GGTTTCTCGTATCGTTCCTTCTGGTGGCACTACTTTTTATGCTGACTCCGTTAAAGGTCGCTTCACTATC

TCTAGAGACAACTCTAAGAATACTCTCTACTTGCAGATGAACAGCTTAAGGGCTGAGGACACTGCAGTCT

ACTATTGTGCGAAAAACGCGCGAAGAGCTTTTCCCTCCATGGACGTCTGGGGCAAAGGGACCACGGTCAC

CGTCTCAAGCGCCTCCACCAAGGGCCCATCGG

C6 LC Coding Sequence-R2

CAGAGCGCTTTGACTCAGGACCCTGCTGTGTCTGTGGCCTTGGGACAGACAGTCAGGATCACATGCCAAG (SEQ ID NO:60)

GAGACAGCCTCAGAAGCTATTATGCAAGCTGGTACCAGCAGAAGCCAGGACAGGCCCCTGTACTTGTCAT

ATATAGTAAAAGTAACCGGCCCTCAGGGATCCCAGACCGATTCTCTGGCTCCAGCTCAGGAAGCACAGCT

TCCTTGACCATCACTGGGGCTCAGGCGGAAGATGAGGCTGACTATTATTGTAACTCCCGGGACAGCAGTG

GTAACCATCTGGTATTCGGCGGAGGGACCAAGCTGACCGTCCTAGGTCAGCCCAAGGCTGCCCCCTCG

EXAMPLE 14

Exemplary Sequences—A4-R3

Translation of A4-R3 HC (1-382)

1 EVQLLESGGG LVQPGGSLRL SCAASGFTFS RYNMYWVRQA PGKGLEWVSG (SEQ ID NO:61)

51 IRPSGGSTQY ADSVKGRFTI SRDNSKNTLY LQMNSLRAED TAVYYCAKNA

101 RRAFPSMDVW GKGTTVTVSS ASTKGPS

-continued

Translation of A4-R3 LC (1-345)

1QSELTQDPAV SVALGQTVRI TCRGDRLRSY YSSWYQQKPR QAPVLVMFGR (SEQ ID NO:62)

51KNRPSGIPDR FSGSTSGSTA SLTITATQAD DEADYFCSSR DGSGNFLFGG

101GTKLTVLGQP KAAPS

A4 HC Coding Sequence-R3

GAAGTTCAATTGTTAGAGTCTGGTGGCGGTCTTGTTCAGCCTGGTGGTTCTTTACGTCTTTCTTGCGCTG (SEQ ID NO:63)

CTTCCGGATTCACTTTCTCTCGTTACAATATGTATTGGGTTCGCCAAGCTCCTGGTAAAGGTTTGGAGTG

GGTTTCTGGTATCCGTCCTTCTGGTGGCTCTACTCAGTATGCTGACTCCGTTAAAGGTCGCTTCACTATC

TCTAGAGACAACTCTAAGAATACTCTCTACTTGCAGATGAACAGCTTAAGGGCTGAGGACACTGCAGTCT

ACTATTGTGCGAAAAACGCGCGAAGAGCTTTTCCCTCCATGGACGTCTGGGGCAAAGGGACCACGGTCAC

CGTCTCAAGCGCCTCCACCAAGGGCCCATCGG

A4 LC Coding Sequence-R3

CAGAGCGAATTGACTCAGGACCCTGCTGTGTCTGTGGCCTTGGGGCAGACAGTCAGGATTACATGCCGAG (SEQ ID NO:64)

GAGACAGACTCAGAAGTTATTATTCAAGTTGGTACCAGCAGAAGCCACGACAGGCCCCTGTTCTTGTCAT

GTTTGGTAGAAAGAACCGGCCCTCAGGGATCCCAGACCGATTCTCTGGCTCCACCTCAGGAAGCACAGCT

TCCTTGACCATCACTGCGACTCAGGCGGACGATGAGGCTGACTATTTCTGTAGTTCCCGGGACGGCAGTG

GTAATTTCCTCTTCGGCGGAGGGACCAAACTGACCGTCCTTGGTCAGCCCAAGGCTGCCCCCTCG

EXAMPLE 15

Exemplary Sequences—C1-R3

Translation of C1-R3 HC (1-382)

1EVQLLESGGG LVQPGGSLRL SCAASGFTFS RYSMHWVRQA PGKGLEWVSG (SEQ ID NO:65)

51IRPSGGSTKY ADSVKGRFTI SRDNSKNTLY LQMNSLRAED TAVYYCAKNA

101RRAFPSMDVW GKGTTVTVSS ASTKGPS

Translation of C1-R3 LC (1-345)

1QDIQMTQSPS SLSASVGDRV TITCRASQSI STYLNWYQQR PGEAPKLLIY (SEQ ID NO:66)

51GASSLVSGVP SRFSGSGSGT DFTLTISSLQ PEDFATYYCH QSYITSWTFG

101QGTKVEIKRT VA

C1 HC Coding Sequence-R3

GAAGTTCAATTGTTAGAGTCTGGTGGCGGTCTTGTTCAGCCTGGTGGTTCTTTACGTCTTTCTTGCGCTG (SEQ ID NO:67)

CTTCCGGATTCACTTTCTCTCGTTACTCTATGCATTGGGTTCGCCAAGCTCCTGGTAAAGGTTTGGAGTG

GGTTTCTGGTATCCGTCCTTCTGGTGGCTCTACTAAGTATGCTGACTCCGTTAAAGGTCGCTTCACTATC

TCTAGAGACAACTCTAAGAATACTCTCTACTTGCAGATGAACAGCTTAAGGGCTGAGGACACTGCAGTCT

ACTATTGTGCGAAAAACGCGCGAAGAGCTTTTCCCTCCATGGACGTCTGGGGCAAAGGGACCACGGTCAC

CGTCTCAAGCGCCTCCACCAAGGGCCCATCGG

C1 LC Coding Sequence-R3

CAAGACATCCAGATGACCCAGTCTCCTTCCTCCCTGTCTGCATCTGTAGGAGACAGAGTCACCATCACTT (SEQ ID NO:68)

GCCGGGCAAGTCAGAGCATTAGCACCTACTTAAACTGGTATCAGCAGAGACCAGGGGAAGCCCCTAAACT

CCTGATCTATGGTGCATCCAGTTTGGTGAGTGGGGTCCCATCAAGATTTAGTGGCAGCGGATCTGGGACA

GATTTCACTCTCACCATCTCCAGTCTGCAACCTGAAGATTTTGCAACTTACTACTGTCACCAGAGTTACA

TTACCTCGTGGACGTTCGGCCAAGGGACCAAGGTGGAAATCAAACGAACTGTGGCTGCACCATCT

EXAMPLE 16

Exemplary Sequences—A2

```
Translation of A2 HC (1-341)
  1EVQLLESGGG LVQPGGSLRL SCAASGFTFS RYRMYWVRQA PGKGLEWVSS              (SEQ ID NO:69)

 51ISPSGGDTRY ADSVKGRFTI SRDNSKNTLY LQMNSLRAED TAVYYCARGG

101PRGNKYYFDY WGQ

Translation of A2 LC (1-337)
  1QDIQMTQSPS FLSAFVGDRV TITCRASQDI RSDLAWYQQT PGKAPKLLIY              (SEQ ID NO:70)

 51AASTLKDGAP SRFSGSGSGT EFTLTISSLH PEDLATYYCQ HLNGHPAFGP

101GTKVNIQRTV AA

A2 HC coding nucleic acid
GAAGTTCAATTGTTAGAGTCTGGTGGCGGTCTTGTTCAGCCTGGTGGTTCTTTACGTCTTTCTTGCGCTG  (SEQ ID NO:71)

CTTCCGGATTCACTTTCTCTCGTTACCGTATGTATTGGGTTCGCCAAGCTCCTGGTAAAGGTTTGGAGTG

GGTTTCTTCTATCTCTCCTTCTGGTGGCGATACTCGTTATGCTGACTCCGTTAAAGGTCGCTTCACTATC

TCTAGAGACAACTCTTAGAATACTCTCTACTTGCAGATGAACAGCTTAAGGGCTGAGGACACTGCAGTCT

ACTATTGTGCGAGAGGGGGACCGCGGGGTAACAAGTACTACTTTGACTACTGGGGCCAGGG

A2 LC coding nucleic acid
CAAGACATCCAGATGACCCAGTCTCCATCCTTCCTGTCTGCATTTGTAGGAGACAGGGTCACCATCACTT  (SEQ ID NO:72)

GCCGGGCCAGTCAGGACATTAGAAGTGATTTAGCCTGGTATCAGCAAACACCAGGGAAAGCCCCAAAGCT

CCTGATCTATGCTGCATCCACTTTGAAAGATGGGGCCCCATCAAGATTCAGCGGCAGTGGATCTGGGACA

GAATTTACTCTCACAATCAGCAGCCTGCACCCTGAAGATCTTGCGACTTATTACTGTCAACACCTTAATG

GTCACCCTGCTTTCGGCCCTGGGACCAAAGTGAATATCCAAAGAACTGTGGCTGCAC
```

EXAMPLE 17

Exemplary Sequences—B5

```
Translation of B5 HC (1-341)
  1EVQLLESGGG LVQPGGSLRL SCAASGFTFS RYRMYWVRQA PGKGLEWVSS              (SEQ ID NO:73)

 51ISPSGGDTRY ADSVKGRFTI SRDNSKNTLY LQMNSLRAED TAVYYCARGG

101PRGNKYYFDY WGQ

Translation of B5 LC (1-334)
  1QYELTQPPSV SVSLGQAANI SCSGDRLGDK YTSWYQQQSG QSPVLVIYQD              (SEQ ID NO:74)

 51KKRPSGIPER FSGSSSGNTA TLTISGAQAI DEAAYYCQAW ATNVVFGAGT

101KLTVLGQPKA A

B5 HC coding nucleic acid
GAAGTTCAATTGTTAGAGTCTGGTGGCGGTCTTGTTCAGCCTGGTGGTTCTTTACGTCTTTCTTGCGCTG  (SEQ ID NO:75)

CTTCCGGATTCACTTTCTCTCGTTACCGTATGTATTGGGTTCGCCAAGCTCCTGGTAAAGGTTTGGAGTG

GGTTTCTTCTATCTCTCCTTCTGGTGGCGATACTCGTTATGCTGACTCCGTTAAAGGTCGCTTCACTATC

TCTAGAGACAACTCTTAGAATACTCTCTACTTGCAGATGAACAGCTTAAGGGCTGAGGACACTGCAGTCT

ACTATTGTGCGAGAGGGGGACCGCGGGGTAACAAGTACTACTTTGACTACTGGGGCCAGGG

B5 LC coding nucleic acid
CAGTACGAATTGACTCAGCCACCCTCAGTGTCCGTGTCCCTAGGACAGGCAGCCAACATCTCCTGCTCTG  (SEQ ID NO:76)

GAGATAGATTGGGGGATAAATATACTTCCTGGTATCAACAACAGTCAGGACAGTCCCCTGTCCTGGTCAT

CTATCAAGATAAGAAGCGACCCTCAGGGATCCCCGAGCGATTCTCTGGCTCCTCCTCTGGGAACACAGCC
```

-continued

ACTCTGACCATCAGCGGGGCCCAGGCCATAGATGAGGCTGCCTATTACTGTCAGGCGTGGGCCACCAATG

TGGTTTTCGGCGCTGGGACCAAGCTGACCGTCCTAGGTCAGCCCAAGGCTGCCC

EXAMPLE 18

Exemplary Sequences—D2

Translation of D2 HC (1-341)
1 EVQLLESGGG LVQPGGSLRL SCAASGFTFS RYRMYWVRQA PGKGLEWVSS (SEQ ID NO:77)

51 ISPSGGDTRY ADSVKGRFTI SRDNSKNTLY LQMNSLRAED TAVYYCARGG

101 PRGNKYYFDY WGQ

Translation of D2 LC (1-340)
1 QDIQMTQSPS SLSASVGDRV TITCRASQTI DNYLNWYQQK PGKAPKLVVY (SEQ ID NO:78)

51 AASTLQTRVP SRFSGSGSGT DFTLTIDSLK PEDFATYFCQ QGFSNPWTFG

101 QGTTVAMIRT VAA

D2 HC coding nucleic acid
GAAGTTCAATTGTTAGAGTCTGGTGGCGGTCTTGTTCAGCCTGGTGGTTCTTTACGTCTTTCTTGCGCTG (SEQ ID NO:79)

CTTCCGGATTCACTTTCTCTCGTTACCGTATGTATTGGGTTCGCCAAGCTCCTGGTAAAGGTTTGGAGTG

GGTTTCTTCTATCTCTCCTTCTGGTGGCGATACTCGTTATGCTGACTCCGTTAAAGGTCGCTTCACTATC

TCTAGAGACAACTCTTAGAATACTCTCTACTTGCAGATGAACAGCTTAAGGGCTGAGGACACTGCAGTCT

ACTATTGTGCGAGAGGGGGACCGCGGGGTAACAAGTACTACTTTGACTACTGGGGCCAGGG

D2 LC coding nucleic acid
CAAGACATCCAGATGACCCAGTCTCCATCCTCCCTGTCTGCTTCTGTTGGAGACAGAGTCACCATCACTT (SEQ ID NO:80)

GCCGGGCAAGCCAGACCATTGACAATTATTTGAATTGGTATCAGCAGAAACCAGGGAAAGCCCCCAAACT

CGTGGTCTATGCTGCATCCACTTTGCAAACTAGGGTCCCATCAAGGTTCAGTGGCAGTGGGTCTGGGACA

GACTTCACTCTCACCATCGACAGTCTGAAACCTGAAGATTTTGCAACTTACTTCTGTCAACAGGGTTTCA

GTAATCCTTGGACGTTCGGCCAAGGGACCACGGTGGCAATGATACGAACTGTGGCTGCAC

EXAMPLE 19

Exemplary Sequences—D5

Translation of D5 HC (1-332)
1 EVQLLESGGG LVQPGGSLRL SCAASGFTFS RYDMHWVRQA PGKGLEWVSS (SEQ ID NO:81)

51 ISSSGGYTAY ADSVKGRFTI SRDNSKNTLY LQMNSLRAED TAVYYCARGA

101 RGTSQGYWGQ

Translation of D5 LC (1-346)
1 QDIQMTQSPG TLSLSPGERG TLSCRASQFV SYSYLAWYQQ KPGQAPRLLI (SEQ ID NO:82)

51 YGASSRAKGI PDRFSGSGSG TDFTLTITRL EPEDFAVYYC QQYVPSVPWT

101 FGQGTKVEVK RTVAA

D5 HC coding nucleic acid
GAAGTTCAATTGTTAGAGTCTGGTGGCGGTCTTGTTCAGCCTGGTGGTTCTTTACGTCTTTCTTGCGCTG (SEQ ID NO:83)

CTTCCGGATTCACTTTCTCTCGTTACGATATGCATTGGGTTCGCCAAGCTCCTGGTAAAGGTTTGGAGTG

GGTTTCTTCTATCTCTTCTTCTGGTGGCTATACTGCTTATGCTGACTCCGTTAAAGGTCGCTTCACTATC

-continued

TCTAGAGACAACTCTAAGAATACTCTCTACTTGCAGATGAACAGCTTAAGGGCTGAGGACACTGCAGTCT

ACTATTGTGCGAGAGGCGCCCGAGGTACCAGCCAAGGCTACTGGGGCCAGGG

D5 LC coding nucleic acid
CAAGACATCCAGATGACTCAGTCTCCAGGCACCCTGTCATTGTCTCCAGGGGAAAGAGGCACCCTCTCCT (SEQ ID NO:84)

GCAGGGCCAGTCAGTTTGTTAGTTACAGCTACTTAGCCTGGTACCAGCAGAAGCCTGGCCAGGCTCCCCG

GCTCCTCATCTATGGCGCATCCAGCAGGGCCAAAGGCATCCCAGACAGGTTCAGTGGCAGTGGGTCTGGG

ACAGACTTCACTCTCACCATCACCAGACTGGAGCCTGAAGACTTTGCAGTTTATTACTGTCAGCAGTATG

TTCCCTCAGTTCCGTGGACGTTCGGCCAAGGGACCAAGGTGGAAGTCAAACGAACTGTGGCTGCAC

EXAMPLE 20

Exemplary Sequences—F8

Translation of F8 HC (1-341)
1EVQLLESGGG LVQPGGSLRL SCAASGFTFS RYHMWWVRQA PGKGLEWVSG (SEQ ID NO:85)

51ISSSRGITKY ADSVKGRFTI SRDNSKNTLY LQMNSLRAED TAVYYCARGG

101PRGNKYYFDY WGQ

Translation of F8 LC (1-343)
1QDIQMTQSPG TLSLSPGERV TLSCRASQSV TSSDLAWYQQ KPGQAPRLLI (SEQ ID NO:86)

51SGASSRATGI PDRFSGSGSG TDFTLTISRL EPEDFAVYYC QQYGNSPGTF

101GQGTKVEIKR TVAA

F8 HC coding nucleic acid
GAAGTTCAATTGTTAGAGTCTGGTGGCGGTCTTGTTCAGCCTGGTGGTTCTTTACGTCTTTCTTGCGCTG (SEQ ID NO:87)

CTTCCGGATTCACTTTCTCTCGTTACCATATGTGGTGGGTTCGCCAAGCTCCTGGTAAAGGTTTGGAGTG

GGTTTCTGGTATCTCTTCTTCTCGTGGCATTACTAAGTATGCTGACTCCGTTAAAGGTCGCTTCACTATC

TCTAGAGACAACTCTAAGAATACTCTCTACTTGCAGATGAACAGCTTAAGGGCTGAGGACACTGCAGTCT

ACTATTGTGCGAGAGGGGGACCGCGGGGTAACAAGTACTACTTTGACTACTGGGGCCAGGG

F8 LC coding nucleic acid
CAAGACATCCAGATGACCCAGTCTCCAGGCACCCTGTCTTTGTCTCCAGGGGAAAGAGTCACCCTCTCCT (SEQ ID NO:88)

GCAGGGCCAGTCAGAGTGTTACCAGCAGCGACTTAGCCTGGTACCAGCAGAAACCTGGTCAGGCTCCCAG

GCTCCTCATTTCTGGTGCATCCAGCAGGGCCACTGGCATCCCAGACAGGTTCAGTGGCAGTGGGTCTGGG

ACAGACTTCACCCTCACCATCAGCAGACTGGAACCTGAAGATTTTGCAGTGTATTACTGTCAGCAGTATG

GTAACTCACCTGGGACGTTCGGCCAAGGGACCAAGGTGGAAATCAAACGAACTGTGGCTGCAC

EXAMPLE 21

Exemplary Sequences—H10

Translation of H10 HC (1-341)
1EVQLLESGGG LVQPGGSLRL SCAASGFTFS RYRMYWVRQA PGKGLEWVSS (SEQ ID NO:89)

51ISPSGGDTRY ADSVKGRFTI SRDNSKNTLY LQMNSLRAED TAVYYCARGG

101PRGNKYYFDY WGQ

Translation of H10 LC (1-343)
1QDIQMTQSPG TLSLSPGERA TLSCRASQSV SSSYLAWYQQ KPGQAPRLLI (SEQ ID NO:90)

51YGASSRATGI PDRFSGSGSG TDFTLTISRL EPEDFAVYYC QQYGSSTWTF

101GQGTKVEIKR TVAA

-continued

H10 HC coding nucleic acid
GAAGTTCAATTGTTAGAGTCTGGTGGCGGTCTTGTTCAGCCTGGTGGTTCTTTACGTCTTTCTTGCGCTGCTTCCGG (SEQ ID NO:91)

ATTCACTTTCTCTCGTTACCGTATGTATTGGGTTCGCCAAGCTCCTGGTAAAGGTTTGGAGTGGGTTTCTTCTATCT

CTCCTTCTGGTGGCGATACTCGTTATGCTGACTCCGTTAAAGGTCGCTTCACTATCTCTAGAGACAACTCTTAGAAT

ACTCTCTACTTGCAGATGAACAGCTTAAGGGCTGAGGACACTGCAGTCTACTATTGTGCGAGAGGGGGACCGCGGGG

TAACAAGTACTACTTTGACTACTGGGGCCAGGG

H10 LC coding nucleic acid
CAAGACATCCAGATGACCCAGTCTCCAGGCACCCTGTCTTTGTCTCCAGGGGAAAGAGCCACCCTCTCCT (SEQ ID NO:92)

GCAGGGCCAGTCAGAGTGTTAGCAGCAGCTACTTAGCCTGGTACCAGCAGAAACCTGGCCAGGCTCCCAG

GCTCCTCATCTATGGTGCATCCAGCAGGGCCACTGGCATCCCAGACAGGTTCAGTGGCAGTGGGTCTGGG

ACAGACTTCACTCTCACCATCAGCAGACTGGAGCCTGAAGATTTTGCAGTGTATTACTGTCAGCAGTATG

GTAGCTCAACGTGGACGTTCGGCCAAGGGACCAAAGTGGAAATCAAACGAACTGTGGCTGCAC

The stop codon in the middle of a coding nucleic acid can be replaced by another codon, e.g., a codon that encodes lysine. Alternatively, a bacterial strain with a tRNA suppressor can be used to introduce a lysine or other amino acid at this position.

A number of embodiments of the invention have been described. Nevertheless, it will be understood that various modifications may be made without departing from the spirit and scope of the invention. Accordingly, other embodiments are within the scope of the following claims.

What is claimed is:

1. An isolated antibody comprising a heavy chain (HC) immunoglobulin variable domain sequence comprising an HC CDR1, an HC CDR2, and an HC CDR3, and a light chain (LC) immunoglobulin variable domain sequence comprising an LC CDR1, an LC CDR2, and an LC CDR3, wherein all of said HC CDR1, HC CDR2, HC CDR3, LC CDR1, LC CDR2, and LC CDR3 are selected from any one antibody selected from the group consisting of A2, B5, D2, D5, F8, H10, and C9; and wherein the HC and LC immunoglobulin variable domain sequences form an antigen binding site that specifically binds to human endotheliase-2 (ET2) of SEQ ID NO:2 or SEQ ID NO:94.

2. The antibody of claim 1, wherein the antibody accumulates at sites of angiogenesis in vivo.

3. The antibody of claim 1, wherein the antibody inhibits proteolysis of vessel basement membrane.

4. The antibody of claim 1, wherein the antibody inhibits angiogenesis in vitro or in vivo.

5. The antibody of claim 1, wherein the antibody is a single chain antibody.

6. The antibody of claim 1, wherein the antibody is a Fab fragment, a $F(ab')_2$ fragment, a Fd fragments, a Fv fragment, or a dAb fragment.

7. The antibody of claim 1, wherein the antibody is a full-length antibody.

8. The antibody of claim 1, wherein the antibody is a human or humanized antibody.

9. The antibody of claim 1, wherein the antibody comprises a human antibody framework region.

10. The antibody of claim 1, wherein the antibody comprises an Fc domain.

11. The antibody of claim 1, wherein antibody comprises the amino acid sequence of SEQ ID NO:77 and the amino acid sequence of SEQ ID NO:78.

12. A pharmaceutical composition comprising the antibody of claim 1 and a pharmaceutically acceptable carrier.

13. The antibody of claim 1, wherein the antibody inhibits ET2 protease activity with an inhibition constant (Ki) of less than 300 nM.

* * * * *

SEQUENCE LISTING

```
<160> NUMBER OF SEQ ID NOS: 113

<210> SEQ ID NO 1
<211> LENGTH: 2067
<212> TYPE: DNA
<213> ORGANISM: Homo sapiens
<220> FEATURE:
<221> NAME/KEY: CDS
<222> LOCATION: (1)...(2064)

<400> SEQUENCE: 1

atg gag agg gac agc cac ggg aat gca tct cca gca aga aca cct tca       48
Met Glu Arg Asp Ser His Gly Asn Ala Ser Pro Ala Arg Thr Pro Ser
 1               5                  10                  15

gct gga gca tct cca gcc cag gca tct cca gct ggg aca cct cca ggc       96
Ala Gly Ala Ser Pro Ala Gln Ala Ser Pro Ala Gly Thr Pro Pro Gly
            20                  25                  30

cgg gca tct cca gcc cag gca tct cca gcc cag gca tct cca gct ggg      144
Arg Ala Ser Pro Ala Gln Ala Ser Pro Ala Gln Ala Ser Pro Ala Gly
        35                  40                  45

aca cct ccg ggc cgg gca tct cca gcc cag gca tct cca gct ggt aca      192
Thr Pro Pro Gly Arg Ala Ser Pro Ala Gln Ala Ser Pro Ala Gly Thr
    50                  55                  60

cct cca ggc cgg gca tct cca ggc cgg gca tct cca gcc cag gca tct      240
Pro Pro Gly Arg Ala Ser Pro Gly Arg Ala Ser Pro Ala Gln Ala Ser
65                  70                  75                  80

cca gcc cgg gca tct ccg gct ctg gca tca ctt tcc agg tcc tca tcc      288
Pro Ala Arg Ala Ser Pro Ala Leu Ala Ser Leu Ser Arg Ser Ser Ser
                85                  90                  95

ggc agg tca tca tcc gcc agg tca gcc tcg gtg aca acc tcc cca acc      336
Gly Arg Ser Ser Ser Ala Arg Ser Ala Ser Val Thr Thr Ser Pro Thr
            100                 105                 110

aga gtg tac ctt gtt aga gca aca cca gtg ggg gct gta ccc atc cga      384
Arg Val Tyr Leu Val Arg Ala Thr Pro Val Gly Ala Val Pro Ile Arg
```

-continued

```
        115                 120                 125

tca tct cct gcc agg tca gca cca gca acc agg gcc acc agg gag agc      432
Ser Ser Pro Ala Arg Ser Ala Pro Ala Thr Arg Ala Thr Arg Glu Ser
    130                 135                 140

cca ggt acg agc ctg ccc aag ttc acc tgg cgg gag ggc cag aag cag      480
Pro Gly Thr Ser Leu Pro Lys Phe Thr Trp Arg Glu Gly Gln Lys Gln
145                 150                 155                 160

cta ccg ctc atc ggg tgc gtg ctc ctc ctc att gcc ctg gtg gtt tcg      528
Leu Pro Leu Ile Gly Cys Val Leu Leu Leu Ile Ala Leu Val Val Ser
                165                 170                 175

ctc atc atc ctc ttc cag ttc tgg cag ggc cac aca ggg atc agg tac      576
Leu Ile Ile Leu Phe Gln Phe Trp Gln Gly His Thr Gly Ile Arg Tyr
            180                 185                 190

aag gag cag agg gag agc tgt ccc aag cac gct gtt cgc tgt gac ggg      624
Lys Glu Gln Arg Glu Ser Cys Pro Lys His Ala Val Arg Cys Asp Gly
        195                 200                 205

gtg gtg gac tgc aag ctg aag agt gac gag ctg ggc tgc gtg agg ttt      672
Val Val Asp Cys Lys Leu Lys Ser Asp Glu Leu Gly Cys Val Arg Phe
    210                 215                 220

gac tgg gac aag tct ctg ctt aaa atc tac tct ggg tcc tcc cat cag      720
Asp Trp Asp Lys Ser Leu Leu Lys Ile Tyr Ser Gly Ser Ser His Gln
225                 230                 235                 240

tgg ctt ccc atc tgt agc agc aac tgg aat gac tcc tac tca gag aag      768
Trp Leu Pro Ile Cys Ser Ser Asn Trp Asn Asp Ser Tyr Ser Glu Lys
                245                 250                 255

acc tgc cag cag ctg ggt ttc gag agt gct cac cgg aca acc gag gtt      816
Thr Cys Gln Gln Leu Gly Phe Glu Ser Ala His Arg Thr Thr Glu Val
            260                 265                 270

gcc cac agg gat ttt gcc aac agc ttc tca atc ttg aga tac aac tcc      864
Ala His Arg Asp Phe Ala Asn Ser Phe Ser Ile Leu Arg Tyr Asn Ser
        275                 280                 285

acc atc cag gaa agc ctc cac agg tct gaa tgc cct tcc cag cgg tat      912
Thr Ile Gln Glu Ser Leu His Arg Ser Glu Cys Pro Ser Gln Arg Tyr
    290                 295                 300

atc tcc ctc cag tgt tcc cac tgc gga ctg agg gcc atg acc ggg cgg      960
Ile Ser Leu Gln Cys Ser His Cys Gly Leu Arg Ala Met Thr Gly Arg
305                 310                 315                 320

atc gtg gga ggg gcg ctg gcc tcg gat agc aag tgg cct tgg caa gtg     1008
Ile Val Gly Gly Ala Leu Ala Ser Asp Ser Lys Trp Pro Trp Gln Val
                325                 330                 335

agt ctg cac ttc ggc acc acc cac atc tgt gga ggc acg ctc att gac     1056
Ser Leu His Phe Gly Thr Thr His Ile Cys Gly Gly Thr Leu Ile Asp
            340                 345                 350

gcc cag tgg gtg ctc act gcc gcc cac tgc ttc ttc gtg acc cgg gag     1104
Ala Gln Trp Val Leu Thr Ala Ala His Cys Phe Phe Val Thr Arg Glu
        355                 360                 365

aag gtc ctg gag ggc tgg aag gtg tac gcg ggc acc agc aac ctg cac     1152
Lys Val Leu Glu Gly Trp Lys Val Tyr Ala Gly Thr Ser Asn Leu His
    370                 375                 380

cag ttg cct gag gca gcc tcc att gcc gag atc atc atc aac agc aat     1200
Gln Leu Pro Glu Ala Ala Ser Ile Ala Glu Ile Ile Ile Asn Ser Asn
385                 390                 395                 400

tac acc gat gag gag gac gac tat gac atc gcc ctc atg cgg ctg tcc     1248
Tyr Thr Asp Glu Glu Asp Asp Tyr Asp Ile Ala Leu Met Arg Leu Ser
                405                 410                 415

aag ccc ctg acc ctg tcc gct cac atc cac cct gct tgc ctc ccc atg     1296
Lys Pro Leu Thr Leu Ser Ala His Ile His Pro Ala Cys Leu Pro Met
            420                 425                 430

cat gga cag acc ttt agc ctc aat gag acc tgc tgg atc aca ggc ttt     1344
```

-continued

```
His Gly Gln Thr Phe Ser Leu Asn Glu Thr Cys Trp Ile Thr Gly Phe
        435                 440                 445

ggc aag acc agg gag aca gat gac aag aca tcc ccc ttc ctc cgg gag      1392
Gly Lys Thr Arg Glu Thr Asp Asp Lys Thr Ser Pro Phe Leu Arg Glu
    450                 455                 460

gtg cag gtc aat ctc atc gac ttc aag aaa tgc aat gac tac ttg gtc      1440
Val Gln Val Asn Leu Ile Asp Phe Lys Lys Cys Asn Asp Tyr Leu Val
465                 470                 475                 480

tat gac agt tac ctt acc cca agg atg atg tgt gct ggg gac ctt cgt      1488
Tyr Asp Ser Tyr Leu Thr Pro Arg Met Met Cys Ala Gly Asp Leu Arg
                485                 490                 495

ggg ggc aga gac tcc tgc cag gga gac agc ggg ggg cct ctt gtc tgt      1536
Gly Gly Arg Asp Ser Cys Gln Gly Asp Ser Gly Gly Pro Leu Val Cys
            500                 505                 510

gag cag aac aac cgc tgg tac ctg gca ggt gtc acc agc tgg ggc aca      1584
Glu Gln Asn Asn Arg Trp Tyr Leu Ala Gly Val Thr Ser Trp Gly Thr
        515                 520                 525

ggc tgt ggc cag aga aac aaa cct ggt gtg tac acc aaa gtg aca gaa      1632
Gly Cys Gly Gln Arg Asn Lys Pro Gly Val Tyr Thr Lys Val Thr Glu
    530                 535                 540

gtt ctt ccc tgg att tac agc aag atg gag aac aga gct cag cgg gtt      1680
Val Leu Pro Trp Ile Tyr Ser Lys Met Glu Asn Arg Ala Gln Arg Val
545                 550                 555                 560

gaa aaa gcg tgg acc tac agg cca ggc agg cag ttg ctg ggc aga tgt      1728
Glu Lys Ala Trp Thr Tyr Arg Pro Gly Arg Gln Leu Leu Gly Arg Cys
                565                 570                 575

tct ccc aga agt att ttt ttg tgt aag gtt gca atg gac ttt gaa aac      1776
Ser Pro Arg Ser Ile Phe Leu Cys Lys Val Ala Met Asp Phe Glu Asn
            580                 585                 590

gtt tca gtt tct gca gag gat ttt gtg ata gtt ttt gtt atc aag cat      1824
Val Ser Val Ser Ala Glu Asp Phe Val Ile Val Phe Val Ile Lys His
        595                 600                 605

tta tgc atg gga atc cgc tct tca tgg cct ttc cca gct ctg ttt gtt      1872
Leu Cys Met Gly Ile Arg Ser Ser Trp Pro Phe Pro Ala Leu Phe Val
    610                 615                 620

tta gtc ttt ttg att ttc ttt ttg ttg ttg ttg ttg tct ttt tta aaa      1920
Leu Val Phe Leu Ile Phe Phe Leu Leu Leu Leu Leu Ser Phe Leu Lys
625                 630                 635                 640

aac aca agt gac tcc att ttg act ctg aca act ttc aca gct gtc acc      1968
Asn Thr Ser Asp Ser Ile Leu Thr Leu Thr Thr Phe Thr Ala Val Thr
                645                 650                 655

aga atg ctc cct gag aac tac cat tct ttc cct ttc cca ctt aaa ata      2016
Arg Met Leu Pro Glu Asn Tyr His Ser Phe Pro Phe Pro Leu Lys Ile
            660                 665                 670

ttt cat cag aac ctc act act atc ata aaa gag tat aaa gta ata aaa      2064
Phe His Gln Asn Leu Thr Thr Ile Ile Lys Glu Tyr Lys Val Ile Lys
        675                 680                 685

taa                                                                  2067


<210> SEQ ID NO 2
<211> LENGTH: 688
<212> TYPE: PRT
<213> ORGANISM: Homo sapiens

<400> SEQUENCE: 2

Met Glu Arg Asp Ser His Gly Asn Ala Ser Pro Ala Arg Thr Pro Ser
 1               5                  10                  15

Ala Gly Ala Ser Pro Ala Gln Ala Ser Pro Ala Gly Thr Pro Pro Gly
            20                  25                  30
```

-continued

```
Arg Ala Ser Pro Ala Gln Ala Ser Pro Ala Gln Ala Ser Pro Ala Gly
        35                  40                  45

Thr Pro Pro Gly Arg Ala Ser Pro Ala Gln Ala Ser Pro Ala Gly Thr
    50                  55                  60

Pro Pro Gly Arg Ala Ser Pro Gly Arg Ala Ser Pro Ala Gln Ala Ser
65                  70                  75                  80

Pro Ala Arg Ala Ser Pro Ala Leu Ala Ser Leu Ser Arg Ser Ser Ser
                85                  90                  95

Gly Arg Ser Ser Ser Ala Arg Ser Ala Ser Val Thr Thr Ser Pro Thr
            100                 105                 110

Arg Val Tyr Leu Val Arg Ala Thr Pro Val Gly Ala Val Pro Ile Arg
        115                 120                 125

Ser Ser Pro Ala Arg Ser Ala Pro Ala Thr Arg Ala Thr Arg Glu Ser
    130                 135                 140

Pro Gly Thr Ser Leu Pro Lys Phe Thr Trp Arg Glu Gly Gln Lys Gln
145                 150                 155                 160

Leu Pro Leu Ile Gly Cys Val Leu Leu Leu Ile Ala Leu Val Val Ser
                165                 170                 175

Leu Ile Ile Leu Phe Gln Phe Trp Gln Gly His Thr Gly Ile Arg Tyr
            180                 185                 190

Lys Glu Gln Arg Glu Ser Cys Pro Lys His Ala Val Arg Cys Asp Gly
        195                 200                 205

Val Val Asp Cys Lys Leu Lys Ser Asp Glu Leu Gly Cys Val Arg Phe
    210                 215                 220

Asp Trp Asp Lys Ser Leu Leu Lys Ile Tyr Ser Gly Ser Ser His Gln
225                 230                 235                 240

Trp Leu Pro Ile Cys Ser Ser Asn Trp Asn Asp Ser Tyr Ser Glu Lys
                245                 250                 255

Thr Cys Gln Gln Leu Gly Phe Glu Ser Ala His Arg Thr Thr Glu Val
            260                 265                 270

Ala His Arg Asp Phe Ala Asn Ser Phe Ser Ile Leu Arg Tyr Asn Ser
        275                 280                 285

Thr Ile Gln Glu Ser Leu His Arg Ser Glu Cys Pro Ser Gln Arg Tyr
    290                 295                 300

Ile Ser Leu Gln Cys Ser His Cys Gly Leu Arg Ala Met Thr Gly Arg
305                 310                 315                 320

Ile Val Gly Gly Ala Leu Ala Ser Asp Ser Lys Trp Pro Trp Gln Val
                325                 330                 335

Ser Leu His Phe Gly Thr Thr His Ile Cys Gly Gly Thr Leu Ile Asp
            340                 345                 350

Ala Gln Trp Val Leu Thr Ala Ala His Cys Phe Phe Val Thr Arg Glu
        355                 360                 365

Lys Val Leu Glu Gly Trp Lys Val Tyr Ala Gly Thr Ser Asn Leu His
    370                 375                 380

Gln Leu Pro Glu Ala Ala Ser Ile Ala Glu Ile Ile Ile Asn Ser Asn
385                 390                 395                 400

Tyr Thr Asp Glu Glu Asp Asp Tyr Asp Ile Ala Leu Met Arg Leu Ser
                405                 410                 415

Lys Pro Leu Thr Leu Ser Ala His Ile His Pro Ala Cys Leu Pro Met
            420                 425                 430

His Gly Gln Thr Phe Ser Leu Asn Glu Thr Cys Trp Ile Thr Gly Phe
        435                 440                 445

Gly Lys Thr Arg Glu Thr Asp Asp Lys Thr Ser Pro Phe Leu Arg Glu
```

-continued

```
    450                 455                 460

Val Gln Val Asn Leu Ile Asp Phe Lys Lys Cys Asn Asp Tyr Leu Val
465                 470                 475                 480

Tyr Asp Ser Tyr Leu Thr Pro Arg Met Met Cys Ala Gly Asp Leu Arg
                485                 490                 495

Gly Gly Arg Asp Ser Cys Gln Gly Asp Ser Gly Gly Pro Leu Val Cys
            500                 505                 510

Glu Gln Asn Asn Arg Trp Tyr Leu Ala Gly Val Thr Ser Trp Gly Thr
        515                 520                 525

Gly Cys Gly Gln Arg Asn Lys Pro Gly Val Tyr Thr Lys Val Thr Glu
    530                 535                 540

Val Leu Pro Trp Ile Tyr Ser Lys Met Glu Asn Arg Ala Gln Arg Val
545                 550                 555                 560

Glu Lys Ala Trp Thr Tyr Arg Pro Gly Arg Gln Leu Leu Gly Arg Cys
                565                 570                 575

Ser Pro Arg Ser Ile Phe Leu Cys Lys Val Ala Met Asp Phe Glu Asn
            580                 585                 590

Val Ser Val Ser Ala Glu Asp Phe Val Ile Val Phe Val Ile Lys His
        595                 600                 605

Leu Cys Met Gly Ile Arg Ser Ser Trp Pro Phe Pro Ala Leu Phe Val
    610                 615                 620

Leu Val Phe Leu Ile Phe Phe Leu Leu Leu Leu Leu Ser Phe Leu Lys
625                 630                 635                 640

Asn Thr Ser Asp Ser Ile Leu Thr Leu Thr Thr Phe Thr Ala Val Thr
                645                 650                 655

Arg Met Leu Pro Glu Asn Tyr His Ser Phe Pro Phe Pro Leu Lys Ile
            660                 665                 670

Phe His Gln Asn Leu Thr Thr Ile Ile Lys Glu Tyr Lys Val Ile Lys
        675                 680                 685
```

<210> SEQ ID NO 3
<211> LENGTH: 657
<212> TYPE: DNA
<213> ORGANISM: Artificial Sequence
<220> FEATURE:
<223> OTHER INFORMATION: Synthetically generated oligonucleotide

<400> SEQUENCE: 3

```
cagagcgtct tgactcagcc tgcctccgtg tctgggtctc ctggacagtc gatcaccatc     60

tcctgcactg gaaccagtag tgacgttggt cattataatt atgtctcctg gtaccaacag    120

cacccaggca aagcccccaa agtcatgatt tatgatgtca gtagtcggcc ctccggggtt    180

tctgatcgct tctctgggtc caagtctggc aacacggcct ccctggccat ctctgggctc    240

caggctgagg acgaggctga ttattactgc agttcgtata caagcggtga cactctttat    300

gtcttcggaa ctgggaccaa ggtcaccgtc ctaggtcagc ccaaggccaa ccccactgtc    360

actctgttcc cgccctcctc tgaggagctc caagccaaca aggccacact agtgtgtctg    420

atcagtgact tctacccggg agctgtgaca gtggcctgga aggcagatgg cagccccgtc    480

aaggcgggag tggagaccac caaaccctcc aaacagagca acaacaagta cgcggccagc    540

agctacctga gcctgacgcc cgagcagtgg aagtcccaca gaagctacag ctgccaggtc    600

acgcatgaag ggagcaccgt ggagaagaca gtggcccctg cagaatgctc ttaataa       657
```

<210> SEQ ID NO 4
<211> LENGTH: 217

-continued

<212> TYPE: PRT
<213> ORGANISM: Artificial Sequence
<220> FEATURE:
<223> OTHER INFORMATION: Synthetically generated peptide

<400> SEQUENCE: 4

```
Gln Ser Val Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly His Tyr
            20                  25                  30

Asn Tyr Val Ser Trp Tyr Gln Gln His Pro Gly Lys Ala Pro Lys Val
        35                  40                  45

Met Ile Tyr Asp Val Ser Ser Arg Pro Ser Gly Val Ser Asp Arg Phe
    50                  55                  60

Ser Gly Ser Lys Ser Gly Asn Thr Ala Ser Leu Ala Ile Ser Gly Leu
65                  70                  75                  80

Gln Ala Glu Asp Glu Ala Asp Tyr Tyr Cys Ser Ser Tyr Thr Ser Gly
                85                  90                  95

Asp Thr Leu Tyr Val Phe Gly Thr Gly Thr Lys Val Thr Val Leu Gly
            100                 105                 110

Gln Pro Lys Ala Asn Pro Thr Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Gly Ser Pro Val
145                 150                 155                 160

Lys Ala Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Ala Glu Cys Ser
    210                 215
```

<210> SEQ ID NO 5
<211> LENGTH: 398
<212> TYPE: DNA
<213> ORGANISM: Artificial Sequence
<220> FEATURE:
<223> OTHER INFORMATION: Synthetically generated oligonucleotide

<400> SEQUENCE: 5

```
gaagttcaat tgttagagtc tggtggcggt cttgttcagc ctggtggttc tttacgtctt      60

tcttgcgctg cttccggatt cactttctct cgttacccta tgttttgggt tcgccaagct     120

cctggtaaag gtttggagtg ggtttcttat atctcttctt ctggtggctt tactggttat     180

gctgactccg ttaaaggtcg cttcactatc tctagagaca actctaagaa tactctctac     240

ttgcagatga acagcttaag ggctgaggac actgcagtct actattgtgc gagaggggga     300

ccgcggggta acaagtacta ctttgactac tggggccagg gaaccctggt caccgtctca     360

agcgcctcca ccaagggccc atcggtcttc ccgctagc                             398
```

<210> SEQ ID NO 6
<211> LENGTH: 132
<212> TYPE: PRT
<213> ORGANISM: Artificial Sequence
<220> FEATURE:

-continued

<223> OTHER INFORMATION: Synthetically generated peptide

<400> SEQUENCE: 6

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Pro Met Phe Trp Val Arg Gln Ala Pro Gly Lys Gly Leu Glu Trp Val
        35                  40                  45

Ser Tyr Ile Ser Ser Ser Gly Gly Phe Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Pro Arg Gly Asn Lys Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu
    130
```

<210> SEQ ID NO 7
<211> LENGTH: 639
<212> TYPE: DNA
<213> ORGANISM: Artificial Sequence
<220> FEATURE:
<223> OTHER INFORMATION: Synthetically generated oligonucleotide

<400> SEQUENCE: 7

```
agctacgaat tgactcagcc accctcagtg tccgtgtccc taggacaggc agccaacatc     60

tcctgctctg gagatagatt gggggataaa tatacttcct ggtatcaaca acagtcagga    120

cagtcccctg tcctggtcat ctatcaagat aagaagcgac cctcagggat ccccgagcga    180

ttctctggct cctcctctgg gaacacagcc actctgacca tcagcggggc ccaggccata    240

gatgaggctg cctattactg tcaggcgtgg gccaccaatg tggttttcgg cgctgggacc    300

aagctgaccg tcctaggtca gcccaaggct gccccctcgg tcactctgtt cccgccctcc    360

tctgaggagc ttcaagccaa caaggccaca ctggtgtgtc tcataagtga cttctacccg    420

ggagccgtga cagtggcctg gaaggcagat agcagccccg tcaaggcggg agtggagacc    480

accacaccct ccaaacaaag caacaacaag tacgcggcca gcagctatct gagcctgacg    540

cctgagcagt ggaagtccca cagaagctac agctgccagg tcacgcatga agggagcacc    600

gtggagaaga cagtggcccc tacaggatgt tcataataa                           639
```

<210> SEQ ID NO 8
<211> LENGTH: 211
<212> TYPE: PRT
<213> ORGANISM: Artificial Sequence
<220> FEATURE:
<223> OTHER INFORMATION: Synthetically generated peptide

<400> SEQUENCE: 8

```
Ser Tyr Glu Leu Thr Gln Pro Pro Ser Val Ser Val Ser Leu Gly Gln
 1               5                  10                  15

Ala Ala Asn Ile Ser Cys Ser Gly Asp Arg Leu Gly Asp Lys Tyr Thr
            20                  25                  30
```

-continued

```
Ser Trp Tyr Gln Gln Gln Ser Gly Gln Ser Pro Val Leu Val Ile Tyr
        35                  40                  45

Gln Asp Lys Lys Arg Pro Ser Gly Ile Pro Glu Arg Phe Ser Gly Ser
    50                  55                  60

Ser Ser Gly Asn Thr Ala Thr Leu Thr Ile Ser Gly Ala Gln Ala Ile
65                  70                  75                  80

Asp Glu Ala Ala Tyr Tyr Cys Gln Ala Trp Ala Thr Asn Val Val Phe
                85                  90                  95

Gly Ala Gly Thr Lys Leu Thr Val Leu Gly Gln Pro Lys Ala Ala Pro
            100                 105                 110

Ser Val Thr Leu Phe Pro Pro Ser Ser Glu Glu Leu Gln Ala Asn Lys
        115                 120                 125

Ala Thr Leu Val Cys Leu Ile Ser Asp Phe Tyr Pro Gly Ala Val Thr
    130                 135                 140

Val Ala Trp Lys Ala Asp Ser Ser Pro Val Lys Ala Gly Val Glu Thr
145                 150                 155                 160

Thr Thr Pro Ser Lys Gln Ser Asn Asn Lys Tyr Ala Ala Ser Ser Tyr
                165                 170                 175

Leu Ser Leu Thr Pro Glu Gln Trp Lys Ser His Arg Ser Tyr Ser Cys
            180                 185                 190

Gln Val Thr His Glu Gly Ser Thr Val Glu Lys Thr Val Ala Pro Thr
        195                 200                 205

Gly Cys Ser
    210


<210> SEQ ID NO 9
<211> LENGTH: 398
<212> TYPE: DNA
<213> ORGANISM: Artificial Sequence
<220> FEATURE:
<223> OTHER INFORMATION: Synthetically generated oligonucleotide

<400> SEQUENCE: 9

gaagttcaat tgttagagtc tggtggcggt cttgttcagc ctggtggttc tttacgtctt      60

tcttgcgctg cttccggatt cactttctct cgttaccgta tgtattgggt tcgccaagct     120

cctggtaaag gtttggagtg ggtttcttct atctctcctt ctggtggcga tactcgttat     180

gctgactccg ttaaaggtcg cttcactatc tctagagaca actcttagaa tactctctac     240

ttgcagatga acagcttaag ggctgaggac actgcagtct actattgtgc gagaggggga     300

ccgcggggta acaagtacta ctttgactac tggggccagg gaaccctggt caccgtctca     360

agcgcctcca ccaagggccc atcggtcttc ccgctagc                             398


<210> SEQ ID NO 10
<211> LENGTH: 131
<212> TYPE: PRT
<213> ORGANISM: Artificial Sequence
<220> FEATURE:
<223> OTHER INFORMATION: Synthetically generated peptide

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Arg Met Tyr Trp Val Arg Gln Ala Pro Gly Lys Gly Leu Glu Trp Val
        35                  40                  45
```

-continued

```
Ser Ser Ile Ser Pro Ser Gly Gly Asp Thr Arg Tyr Ala Asp Ser Val
    50                  55                  60

Lys Gly Arg Phe Thr Ile Ser Arg Asp Asn Ser Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Gly Pro Arg Gly Asn Lys Tyr Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu
    130


<210> SEQ ID NO 11
<211> LENGTH: 651
<212> TYPE: DNA
<213> ORGANISM: Artificial Sequence
<220> FEATURE:
<223> OTHER INFORMATION: Synthetically generated oligonucleotide

<400> SEQUENCE: 11

gacatccaga tgacccagtc tccaggcacc ctgtctttgt ctccagggga aagagtcacc      60

ctctcctgca gggccagtca gagtgttacc agcagcgact tagcctggta ccagcagaaa     120

cctggtcagg ctcccaggct cctcatttct ggtgcatcca gcagggccac tggcatccca     180

gacaggttca gtggcagtgg gtctgggaca gacttcaccc tcaccatcag cagactggaa     240

cctgaagatt ttgcagtgta ttactgtcag cagtatggta actcacctgg gacgttcggc     300

caagggacca aggtggaaat caaacgaact gtggctgcac catctgtctt catcttcccg     360

ccatctgatg agcagttgaa atctggaact gcctctgttg tgtgcctgct gaataacttc     420

tatcccagag aggccaaagt acagtggaag gtggataacg ccctccaatc gggtaactcc     480

caggagagtg tcacagagca ggacagcaag gacagcacct acagcctcag cagcaccctg     540

acgctgagca aagcagacta cgagaaacac aaagtctacg cctgcgaagt cacccatcag     600

ggcctgagct cgcccgtcac aaagagcttc aacaggggag agtgttaata a              651


<210> SEQ ID NO 12
<211> LENGTH: 215
<212> TYPE: PRT
<213> ORGANISM: Artificial Sequence
<220> FEATURE:
<223> OTHER INFORMATION: Synthetically generated peptide

<400> SEQUENCE: 12

Asp Ile Gln Met Thr Gln Ser Pro Gly Thr Leu Ser Leu Ser Pro Gly
 1               5                  10                  15

Glu Arg Val Thr Leu Ser Cys Arg Ala Ser Gln Ser Val Thr Ser Ser
            20                  25                  30

Asp Leu Ala Trp Tyr Gln Gln Lys Pro Gly Gln Ala Pro Arg Leu Leu
        35                  40                  45

Ile Ser Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asn Ser Pro
                85                  90                  95

Gly Thr Phe Gly Gln Gly Thr Lys Val Glu Ile Lys Arg Thr Val Ala
```

-continued

```
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 13
<211> LENGTH: 398
<212> TYPE: DNA
<213> ORGANISM: Artificial Sequence
<220> FEATURE:
<223> OTHER INFORMATION: Synthetically generated oligonucleotide

<400> SEQUENCE: 13

gaagttcaat tgttagagtc tggtggcggt cttgttcagc ctggtggttc tttacgtctt     60

tcttgcgctg cttccggatt cactttctct cgttaccata tgtggtgggt tcgccaagct    120

cctggtaaag gtttggagtg ggtttctggt atctcttctt ctcgtggcat tactaagtat    180

gctgactccg ttaaaggtcg cttcactatc tctagagaca actctaagaa tactctctac    240

ttgcagatga acagcttaag ggctgaggac actgcagtct actattgtgc gagaggggga    300

ccgcggggta acaagtacta ctttgactac tggggccagg gaaccctggt caccgtctca    360

agcgcctcca ccaagggccc atcggtcttc ccgctagc                            398


<210> SEQ ID NO 14
<211> LENGTH: 132
<212> TYPE: PRT
<213> ORGANISM: Artificial Sequence
<220> FEATURE:
<223> OTHER INFORMATION: Synthetically generated peptide

<400> SEQUENCE: 14

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

His Met Trp Trp Val Arg Gln Ala Pro Gly Lys Gly Leu Glu Trp Val
        35                  40                  45

Ser Gly Ile Ser Ser Ser Arg Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Pro Arg Gly Asn Lys Tyr Tyr Phe Asp Tyr Trp Gly
            100                 105                 110

Gln Gly Thr Leu Val Thr Val Ser Ser Ala Ser Thr Lys Gly Pro Ser
```

-continued

```
        115                 120                 125

Val Phe Pro Leu
    130


<210> SEQ ID NO 15
<211> LENGTH: 651
<212> TYPE: DNA
<213> ORGANISM: Artificial Sequence
<220> FEATURE:
<223> OTHER INFORMATION: Synthetically generated oligonucleotide

<400> SEQUENCE: 15

gacatccaga tgacccagtc tccaggcacc ctgtctttgt ctccagggga aagagccacc     60

ctctcctgca gggccagtca gagtgttagc agcagctact tagcctggta ccagcagaaa    120

cctggccagg ctcccaggct cctcatctat ggtgcatcca gcagggccac tggcatccca    180

gacaggttca gtggcagtgg gtctgggaca gacttcactc tcaccatcag cagactggag    240

cctgaagatt ttgcagtgta ttactgtcag cagtatggta gctcaacgtg gacgttcggc    300

caagggacca aagtggaaat caaacgaact gtggctgcac catctgtctt catcttcccg    360

ccatctgatg agcagttgaa atctggaact gcctctgttg tgtgcctgct gaataacttc    420

tatcccagag aggccaaagt acagtggaag gtggataacg ccctccaatc gggtaactcc    480

caggagagtg tcacagagca ggacagcaag gacagcacct acagcctcag cagcaccctg    540

acgctgagca aagcagacta cgagaaacac aaagtctacg cctgcgaagt cacccatcag    600

ggcctgagct cgcccgtcac aaagagcttc aacaggggag agtgttaata a             651


<210> SEQ ID NO 16
<211> LENGTH: 215
<212> TYPE: PRT
<213> ORGANISM: Artificial Sequence
<220> FEATURE:
<223> OTHER INFORMATION: Synthetically generated peptide

<400> SEQUENCE: 16

Asp Ile Gln Met Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Thr
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175
```

-continued

Ser Ser Thr Leu Thr Leu Ser Lys Ala Asp Tyr Glu Lys His Lys Val
180 185 190

Tyr Ala Cys Glu Val Thr His Gln Gly Leu Ser Ser Pro Val Thr Lys
195 200 205

Ser Phe Asn Arg Gly Glu Cys
210 215

<210> SEQ ID NO 17
<211> LENGTH: 645
<212> TYPE: DNA
<213> ORGANISM: Artificial Sequence
<220> FEATURE:
<223> OTHER INFORMATION: Synthetically generated oligonucleotide

<400> SEQUENCE: 17
gacatccaga tgacccagtc tccatccttc ctgtctgcat ttgtaggaga cagggtcacc 60
atcacttgcc gggccagtca ggacattaga agtgatttag cctggtatca gcaaacacca 120
gggaaagccc caaagctcct gatctatgct gcatccactt tgaaagatgg ggccccatca 180
agattcagcg gcagtggatc tgggacagaa tttactctca caatcagcag cctgcaccct 240
gaagatcttg cgacttatta ctgtcaacac cttaatggtc accctgcttt cggccctggg 300
accaaagtga atatccaaag aactgtggct gcaccatctg tcttcatctt cccgccatct 360
gatgagcagt tgaaatctgg aactgcctct gttgtgtgcc tgctgaataa cttctatccc 420
agagaagcca aagtacagtg gaaggtggat aacgccctcc aatcgggtaa ctcccaggag 480
agtgtcacag agcaggacag caaagacagc acctacagcc tcagcagcac cctgacgctg 540
agcaaagcag actacgagaa acacaaagtc tacgcctgcg aagtcaccca tcagggcctg 600
agctcgcccg tcacaaagag cttcaacagg ggagagtgtt aataa 645

<210> SEQ ID NO 18
<211> LENGTH: 213
<212> TYPE: PRT
<213> ORGANISM: Artificial Sequence
<220> FEATURE:
<223> OTHER INFORMATION: Synthetically generated peptide

<400> SEQUENCE: 18

Asp Ile Gln Met Thr Gln Ser Pro Ser Phe Leu Ser Ala Phe Val Gly
1 5 10 15

Asp Arg Val Thr Ile Thr Cys Arg Ala Ser Gln Asp Ile Arg Ser Asp
20 25 30

Leu Ala Trp Tyr Gln Gln Thr Pro Gly Lys Ala Pro Lys Leu Leu Ile
35 40 45

Tyr Ala Ala Ser Thr Leu Lys Asp Gly Ala Pro Ser Arg Phe Ser Gly
50 55 60

Ser Gly Ser Gly Thr Glu Phe Thr Leu Thr Ile Ser Ser Leu His Pro
65 70 75 80

Glu Asp Leu Ala Thr Tyr Tyr Cys Gln His Leu Asn Gly His Pro Ala
85 90 95

Phe Gly Pro Gly Thr Lys Val Asn Ile Gln Arg Thr Val Ala Ala Pro
100 105 110

Ser Val Phe Ile Phe Pro Pro Ser Asp Glu Gln Leu Lys Ser Gly Thr
115 120 125

Ala Ser Val Val Cys Leu Leu Asn Asn Phe Tyr Pro Arg Glu Ala Lys
130 135 140

-continued

```
Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 19
<211> LENGTH: 648
<212> TYPE: DNA
<213> ORGANISM: Artificial Sequence
<220> FEATURE:
<223> OTHER INFORMATION: Synthetically generated oligonucleotide

<400> SEQUENCE: 19

gacatccaga tgacccagtc tccatcctcc ctgtctgctt ctgttggaga cagagtcacc     60

atcacttgcc gggcaagcca gaccattgac aattatttga attggtatca gcagaaacca    120

gggaaagccc ccaaactcgt ggtctatgct gcatccactt tgcaaactag ggtcccatca    180

aggttcagtg gcagtgggtc tgggacagac ttcactctca ccatcgacag tctgaaacct    240

gaagattttg caacttactt ctgtcaacag ggtttcagta atccttggac gttcggccaa    300

gggaccacgg tggcaatgat acgaactgtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gttaataa                 648


<210> SEQ ID NO 20
<211> LENGTH: 214
<212> TYPE: PRT
<213> ORGANISM: Artificial Sequence
<220> FEATURE:
<223> OTHER INFORMATION: Synthetically generated peptide

<400> SEQUENCE: 20

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Thr Ile Asp Asn Tyr
            20                  25                  30

Leu Asn Trp Tyr Gln Gln Lys Pro Gly Lys Ala Pro Lys Leu Val Val
        35                  40                  45

Tyr Ala Ala Ser Thr Leu Gln Thr Arg Val Pro Ser Arg Phe Ser Gly
    50                  55                  60

Ser Gly Ser Gly Thr Asp Phe Thr Leu Thr Ile Asp Ser Leu Lys Pro
65                  70                  75                  80

Glu Asp Phe Ala Thr Tyr Phe Cys Gln Gln Gly Phe Ser Asn Pro Trp
                85                  90                  95

Thr Phe Gly Gln Gly Thr Thr Val Ala Met Ile Arg Thr Val Ala Ala
            100                 105                 110

Pro Ser Val Phe Ile Phe Pro Pro Ser Asp Glu Gln Leu Lys Ser Gly
```

-continued

```
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 21
<211> LENGTH: 654
<212> TYPE: DNA
<213> ORGANISM: Artificial Sequence
<220> FEATURE:
<223> OTHER INFORMATION: Synthetically generated oligonucleotide

<400> SEQUENCE: 21

gacatccaga tgacccagtc tccaggcacc ctgtcattgt ctccagggga aagaggcacc      60

ctctcctgca gggccagtca gtttgttagt tacagctact tagcctggta ccagcagaag     120

cctggccagg ctccccggct cctcatctat ggcgcatcca gcagggccaa aggcatccca     180

gacaggttca gtggcagtgg gtctgggaca gacttcactc tcaccatcac cagactggag     240

cctgaagact ttgcagttta ttactgtcag cagtatgttc cctcagttcc gtggacgttc     300

ggccaaggga ccaaggtgga agtcaaacga actgtggctg caccatctgt cttcatcttc     360

ccgccatctg atgagcagtt gaaatctgga actgcctctg ttgtgtgcct gctgaataac     420

ttctatccca gagaggccaa agtacagtgg aaggtggata acgccctcca atcgggtaac     480

tcccaggaga gtgtcacaga gcaggacggc aaggacagca cctacagcct cagcagcacc     540

ctgacgctga gcaaagcaga ctacgaggaa cacaaagtct acgcctgcga agtcacccat     600

cagggcctga gctcgcccgt cacaaagagc ttcaacaggg gagagtgtta ataa           654


<210> SEQ ID NO 22
<211> LENGTH: 216
<212> TYPE: PRT
<213> ORGANISM: Artificial Sequence
<220> FEATURE:
<223> OTHER INFORMATION: Synthetically generated peptide

<400> SEQUENCE: 22

Asp Ile Gln Met Thr Gln Ser Pro Gly Thr Leu Ser Leu Ser Pro Gly
 1               5                  10                  15

Glu Arg Gly Thr Leu Ser Cys Arg Ala Ser Gln Phe Val Ser Tyr Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Lys Gly Ile Pro Asp Arg Phe Ser
    50                  55                  60

Gly Ser Gly Ser Gly Thr Asp Phe Thr Leu Thr Ile Thr Arg Leu Glu
65                  70                  75                  80

Pro Glu Asp Phe Ala Val Tyr Tyr Cys Gln Gln Tyr Val Pro Ser Val
                85                  90                  95
```

-continued

```
Pro Trp Thr Phe Gly Gln Gly Thr Lys Val Glu Val Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Gly Lys Asp Ser Thr Tyr Ser
                165                 170                 175

Leu Ser Ser Thr Leu Thr Leu Ser Lys Ala Asp Tyr Glu Glu His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215


<210> SEQ ID NO 23
<211> LENGTH: 389
<212> TYPE: DNA
<213> ORGANISM: Artificial Sequence
<220> FEATURE:
<223> OTHER INFORMATION: Synthetically generated oligonucleotide

<400> SEQUENCE: 23

gaagttcaat tgttagagtc tggtggcggt cttgttcagc ctggtggttc tttacgtctt      60

tcttgcgctg cttccggatt cactttctct cgttacgata tgcattgggt tcgccaagct     120

cctggtaaag gtttggagtg ggtttcttct atctcttctt ctggtggcta tactgcttat     180

gctgactccg ttaaaggtcg cttcactatc tctagagaca actctaagaa tactctctac     240

ttgcagatga acagcttaag ggctgaggac actgcagtct actattgtgc gagaggcgcc     300

cgaggtacca gccaaggcta ctggggccag ggaaccctgg tcaccgtctc aagcgcctcc     360

accaagggcc catcggtctt cccgctagc                                       389


<210> SEQ ID NO 24
<211> LENGTH: 129
<212> TYPE: PRT
<213> ORGANISM: Artificial Sequence
<220> FEATURE:
<223> OTHER INFORMATION: Synthetically generated peptide

<400> SEQUENCE: 24

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Asp Met His Trp Val Arg Gln Ala Pro Gly Lys Gly Leu Glu Trp Val
        35                  40                  45

Ser Ser Ile Ser Ser Ser Gly Gly Tyr Thr Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Arg Gly Thr Ser Gln Gly Tyr Trp Gly Gln Gly Thr
            100                 105                 110
```

-continued

```
Leu Val Thr Val Ser Ser Ala Ser Thr Lys Gly Pro Ser Val Phe Pro
        115                 120                 125

Leu


<210> SEQ ID NO 25
<211> LENGTH: 114
<212> TYPE: PRT
<213> ORGANISM: Artificial Sequence
<220> FEATURE:
<223> OTHER INFORMATION: Synthetically generated peptide

<400> SEQUENCE: 25

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Arg Met Trp Trp Val Arg Gln Ala Pro Gly Lys Gly Leu Glu Trp Val
        35                  40                  45

Ser Tyr Ile Ser Ser Ser Gly Gly Phe Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Ala Arg Arg Ala Leu Pro Ser Met Asp Val Trp Gly Lys
            100                 105                 110

Gly Thr


<210> SEQ ID NO 26
<211> LENGTH: 118
<212> TYPE: PRT
<213> ORGANISM: Artificial Sequence
<220> FEATURE:
<223> OTHER INFORMATION: Synthetically generated peptide

<400> SEQUENCE: 26

Gln Ser Ala Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Pro Val Phe Gly Gly Gly Thr Lys Leu Thr Val Leu Gly Gln
            100                 105                 110

Pro Lys Ala Ala Pro Ser
        115


<210> SEQ ID NO 27
<211> LENGTH: 344
<212> TYPE: DNA
<213> ORGANISM: Artificial Sequence
<220> FEATURE:
```

-continued

<223> OTHER INFORMATION: Synthetically generated oligonucleotide

<400> SEQUENCE: 27
gaagttcaat tgttagagtc tggtggcggt cttgttcagc ctggtggttc tttacgtctt 60
tcttgcgctg cttccggatt cactttctct cgttaccgta tgtggtgggt tcgccaagct 120
cctggtaaag gtttggagtg ggtttcttat atctcttctt ctggtggctt tactaattat 180
gctgactccg ttaaaggtcg cttcactatc tctagagaca actctaagaa tactctctac 240
ttgcagatga acagcttaag ggctgaggac actgcagtct actattgtgc gaaaaacgcg 300
cgaagagctc ttccctccat ggacgtctgg ggcaaaggga ccac 344

<210> SEQ ID NO 28
<211> LENGTH: 354
<212> TYPE: DNA
<213> ORGANISM: Artificial Sequence
<220> FEATURE:
<223> OTHER INFORMATION: Synthetically generated oligonucleotide

<400> SEQUENCE: 28
cagagcgctt tgactcagcc accctcagcg tctgggaccc ccgggcagag ggtcaccatc 60
tcttgttctg gaagcagctc caacatcgga agtaattatg tatactggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccgg 240
tccgaggatg aggctgatta ttactgtgca gcatgggatg acagcctgag tggtccggtg 300
ttcggcggag ggaccaagct gaccgtccta ggtcagccca aggctgcccc ctcg 354

<210> SEQ ID NO 29
<211> LENGTH: 114
<212> TYPE: PRT
<213> ORGANISM: Artificial Sequence
<220> FEATURE:
<223> OTHER INFORMATION: Synthetically generated peptide

<400> SEQUENCE: 29

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Trp Val
        35                  40                  45

Ser Val Ile Tyr Ser Ser Gly Gly Ile Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Pro Arg Gly Glu Val Ala Phe Asp Ile Trp Gly Gln
            100                 105                 110

Gly Thr
```

<210> SEQ ID NO 30
<211> LENGTH: 115
<212> TYPE: PRT
<213> ORGANISM: Artificial Sequence
<220> FEATURE:
<223> OTHER INFORMATION: Synthetically generated protein -continued

<400> SEQUENCE: 30

```
Gln Asp Ile Gln Met Thr Gln Ser Pro Ser Phe Leu Ser Ala Ser Ile
 1               5                  10                  15

Gly Asp Arg Val Thr Ile Thr Cys Trp Ala Ser Gln Gly Ile Ser Asn
            20                  25                  30

Tyr Leu Ala Trp Tyr Gln Gln Lys Pro Gly Lys Ala Pro Lys Leu Leu
        35                  40                  45

Ile Ser Ser Ala Ser Thr Leu Gln Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Ser Ala Thr Tyr Tyr Cys Gln Gln Ala Asn Ser Phe Pro
                85                  90                  95

Trp Thr Phe Gly Gln Gly Thr Arg Val Glu Ile Arg Arg Thr Val Ala
            100                 105                 110

Ala Pro Ser
        115
```

<210> SEQ ID NO 31
<211> LENGTH: 342
<212> TYPE: DNA
<213> ORGANISM: Artificial Sequence
<220> FEATURE:
<223> OTHER INFORMATION: Synthetically generated oligonucleotide

<400> SEQUENCE: 31

```
gaagttcaat tgttagagtc tggtggcggt cttgttcagc ctggtggttc tttacgtctt     60

tcttgcgctg cttccggatt cactttctct cgttacggta tgtcttgggt tcgccaagct    120

cctggtaaag gtttggagtg ggtttctgtt atctattctt ctggtggcat tactcgttat    180

gctgactccg ttaaaggtcg cttcactatc tctagagaca actctaagaa tactctctac    240

ttgcagatga acagcttaag ggctgaggac actgcagtct actactgtgc gagacgggcc    300

ccgagggggg aggtcgcttt tgatatctgg ggccaaggga ca                       342
```

<210> SEQ ID NO 32
<211> LENGTH: 345
<212> TYPE: DNA
<213> ORGANISM: Artificial Sequence
<220> FEATURE:
<223> OTHER INFORMATION: Synthetically generated oligonucleotide

<400> SEQUENCE: 32

```
caagacatcc agatgaccca gtctccatcc ttcctgtctg catctatagg agacagagtc     60

accatcactt gctgggccag tcagggcatt agtaattatt tagcctggta tcagcaaaaa    120

ccagggaaag cccctaagct cctgatctct tctgcatcca ctttgcaaag tggggtccca    180

tcaaggttca gcggcagtgg atctgggaca gaattcactc tcacaatcag cagcctgcag    240

cctgaagatt ctgcaactta ctattgtcaa caggctaaca gtttcccgtg gacgttcggc    300

caagggacca gggtggaaat cagacgaact gtggctgcac catct                    345
```

<210> SEQ ID NO 33
<211> LENGTH: 114
<212> TYPE: PRT
<213> ORGANISM: Artificial Sequence
<220> FEATURE:
<223> OTHER INFORMATION: Synthetically generated peptide

<400> SEQUENCE: 33

-continued

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Lys Met Trp Trp Val Arg Gln Ala Pro Gly Lys Gly Leu Glu Trp Val
        35                  40                  45

Ser Tyr Ile Ser Pro Ser Gly Gly Tyr Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Ala Arg Arg Ala Phe Pro Ser Met Asp Val Trp Gly Lys
            100                 105                 110

Gly Thr


<210> SEQ ID NO 34
<211> LENGTH: 115
<212> TYPE: PRT
<213> ORGANISM: Artificial Sequence
<220> FEATURE:
<223> OTHER INFORMATION: Synthetically generated peptide

<400> SEQUENCE: 34

Gln Ser Ala Leu Thr Gln Asp Pro Ala Val Ser Val Ala Leu Gly Gln
 1               5                  10                  15

Thr Val Arg Ile Thr Cys Arg Gly Asp Arg Leu Arg Ser Tyr Tyr Ser
            20                  25                  30

Ser Trp Tyr Gln Gln Lys Pro Arg Gln Ala Pro Val Leu Val Met Phe
        35                  40                  45

Gly Arg Asn Asn Arg Pro Ser Gly Ile Pro Asp Arg Phe Ser Gly Ser
    50                  55                  60

Thr Ser Gly Ser Thr Ala Ser Leu Thr Ile Thr Ala Thr Gln Ala Asp
65                  70                  75                  80

Asp Glu Ala Asp Tyr Phe Cys Ser Ser Arg Asp Gly Ser Gly Asn Phe
                85                  90                  95

Leu Phe Gly Gly Gly Thr Lys Leu Thr Val Leu Gly Gln Pro Lys Ala
            100                 105                 110

Ala Pro Ser
        115


<210> SEQ ID NO 35
<211> LENGTH: 344
<212> TYPE: DNA
<213> ORGANISM: Artificial Sequence
<220> FEATURE:
<223> OTHER INFORMATION: Synthetically generated oligonucleotide

<400> SEQUENCE: 35

gaagttcaat tgttagagtc tggtggcggt cttgttcagc ctggtggttc tttacgtctt     60

tcttgcgctg cttccggatt cactttctct cgttacaaga tgtggtgggt tcgccaagct    120

cctggtaaag gtttggagtg ggtttcttat atctctcctt ctggtggcta tactggttat    180

gctgactccg ttaaaggtcg cttcactatc tctagagaca actctaagaa tactctctac    240

ttgcagatga acagcttaag ggctgaggac actgcagtct actattgtgc gaaaaacgcg    300

cgaagagctt ttccctccat ggacgtctgg ggcaaaggga ccac                     344
```

-continued

<210> SEQ ID NO 36
<211> LENGTH: 345
<212> TYPE: DNA
<213> ORGANISM: Artificial Sequence
<220> FEATURE:
<223> OTHER INFORMATION: Synthetically generated oligonucleotide

<400> SEQUENCE: 36
cagagcgctt tgactcagga ccctgctgtg tctgtggcct tggggcagac agtcaggatc 60
acatgccgag gagacagact cagaagttat tattcaagtt ggtaccagca gaagccacga 120
caggcccctg ttcttgtcat gtttggtaga aacaaccggc cctcagggat cccagaccga 180
ttctctggct ccacctcagg aagcacagct tccttgacca tcactgcgac tcaggcggac 240
gatgaggctg actatttctg tagttcccgg gacggcagtg gtaatttcct cttcggcgga 300
gggaccaaac tgaccgtcct tggtcagccc aaggctgccc cctcg 345

<210> SEQ ID NO 37
<211> LENGTH: 114
<212> TYPE: PRT
<213> ORGANISM: Artificial Sequence
<220> FEATURE:
<223> OTHER INFORMATION: Synthetically generated peptide

<400> SEQUENCE: 37

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Arg Met Ser Trp Val Arg Gln Ala Pro Gly Lys Gly Leu Glu Trp Val
        35                  40                  45

Ser Ser Ile Ser Ser Ser Gly Gly Ile Thr Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Ile Tyr Tyr Cys
                85                  90                  95

Ala Lys Asn Ala Arg Arg Ala Phe Pro Ser Met Asp Val Trp Gly Lys
            100                 105                 110

Gly Thr

<210> SEQ ID NO 38
<211> LENGTH: 116
<212> TYPE: PRT
<213> ORGANISM: Artificial Sequence
<220> FEATURE:
<223> OTHER INFORMATION: Synthetically generated peptide

<400> SEQUENCE: 38

Gln Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
        35                  40                  45

Ile Tyr Ala Ala Ser Ser Leu Gln Ser Gly Val Pro Ser Arg Phe Ser
    50                  55                  60

Gly Ser Gly Ser Gly Thr Glu Phe Thr Leu Thr Ile Asn Ser Leu Gln

-continued

```
65                  70                  75                  80

Pro Glu Asp Phe Ala Thr Tyr Tyr Cys Gln Gln Leu Thr Gly Tyr Pro
                85                  90                  95

Ser Ile Thr Phe Gly Gln Gly Thr Arg Leu Asp Ile Lys Arg Thr Val
            100                 105                 110

Ala Ala Pro Ser
        115
```

<210> SEQ ID NO 39
<211> LENGTH: 342
<212> TYPE: DNA
<213> ORGANISM: Artificial Sequence
<220> FEATURE:
<223> OTHER INFORMATION: Synthetically generated oligonucleotide

<400> SEQUENCE: 39

```
gaagttcaat tgttagagtc tggtggcggt cttgttcagc ctggtggttc tttacgtctt      60

tcttgcgctg cttccggatt cactttctct cgttaccgta tgtcttgggt tcgccaagct     120

cctggtaaag gtttggagtg ggtttcttct atctcttctt ctggtggcat tactacttat     180

gctgactccg ttaaaggtcg cttcactatc tctagagaca actctaagaa tactctctac     240

ttgcagatga acagcttaag ggctgaggac gctgcaatct actattgtgc gaaaaacgcg     300

cgaagagctt ttccctccat ggacgtctgg ggcaaaggga cc                         342
```

<210> SEQ ID NO 40
<211> LENGTH: 348
<212> TYPE: DNA
<213> ORGANISM: Artificial Sequence
<220> FEATURE:
<223> OTHER INFORMATION: Synthetically generated oligonucleotide

<400> SEQUENCE: 40

```
caagacatcc agatgaccca gtctccatcc tccctgtctg catctgtagg agacagagtc      60

accatcactt gccgggcaag tcagagcatt agcagctatt taaattggta tcagcagaaa     120

ccagggaaag cccctaagct cctgatctat gctgcatcca gtttgcaaag tggggtccca     180

tcaaggttca gcggcagtgg atctgggaca gaattcactc tcacaatcaa cagcctgcag     240

cctgaagatt ttgcaactta ttactgtcaa caacttactg gttacccctc gatcaccttc     300

ggccaaggga cacgactgga cattaaacga actgtggctg caccatct                   348
```

<210> SEQ ID NO 41
<211> LENGTH: 114
<212> TYPE: PRT
<213> ORGANISM: Artificial Sequence
<220> FEATURE:
<223> OTHER INFORMATION: Synthetically generated peptide

<400> SEQUENCE: 41

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Thr Met Ser Trp Val Arg Gln Ala Pro Gly Lys Gly Leu Glu Trp Val
        35                  40                  45

Ser Tyr Ile Val Pro Ser Gly Gly Met Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80
```

-continued

```
Leu Gln Met Asn Ser Leu Arg Ala Glu Asp Thr Ala Val Tyr Tyr Cys
                85                  90                  95

Ala Arg Arg Ala Pro Arg Gly Glu Val Ala Phe Asp Ile Trp Gly Gln
            100                 105                 110

Gly Thr


<210> SEQ ID NO 42
<211> LENGTH: 118
<212> TYPE: PRT
<213> ORGANISM: Artificial Sequence
<220> FEATURE:
<223> OTHER INFORMATION: Synthetically generated peptide

<400> SEQUENCE: 42

Gln Ser Val Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Thr Ser Tyr Thr Ser Ser
                85                  90                  95

Ser Thr Trp Val Phe Gly Gly Gly Thr Lys Leu Thr Val Leu Gly Gln
            100                 105                 110

Pro Lys Ala Ala Pro Ser
        115


<210> SEQ ID NO 43
<211> LENGTH: 342
<212> TYPE: DNA
<213> ORGANISM: Artificial Sequence
<220> FEATURE:
<223> OTHER INFORMATION: Synthetically generated oligonucleotide

<400> SEQUENCE: 43

gaagttcaat tgttagagtc tggtggcggt cttgttcagc ctggtggttc tttacgtctt      60

tcttgcgctg cttccggatt cactttctct cgttacacta tgtcttgggt tcgccaagct     120

cctggtaaag gtttggagtg ggtttcttat atcgttcctt ctggtggcat gactaagtat     180

gctgactccg ttaaaggtcg cttcactatc tctagagaca actctaagaa tactctctac     240

ttgcagatga acagcttaag ggctgaggac actgcagtct actattgtgc gagacgggcc     300

ccgagggggg aggtcgcttt tgatatctgg ggccaaggga ca                        342


<210> SEQ ID NO 44
<211> LENGTH: 354
<212> TYPE: DNA
<213> ORGANISM: Artificial Sequence
<220> FEATURE:
<223> OTHER INFORMATION: Synthetically generated oligonucleotide

<400> SEQUENCE: 44

cagagcgtct tgactcagcc tgcctccgtg tctgggtctc ctggacagtc gatcaccatc      60

tcctgcactg gaaccagcag tgacgttggt ggttataact atgtctcctg gtaccaacag     120
```

-continued

```
cacccaggca aagcccccaa actcatgatt tatgatgtca gtaagcggcc ctcaggggtt    180

tctaatcgct tctctggctc caagtctggc aacacggcct ccctgaccat ctctgggctc    240

caggctgagg acgaggctga ttattactgc acctcatata caagtagcag cacttgggtg    300

ttcggcggag ggaccaagct gaccgtccta ggtcagccca aggctgcccc ctcg          354
```

<210> SEQ ID NO 45
<211> LENGTH: 114
<212> TYPE: PRT
<213> ORGANISM: Artificial Sequence
<220> FEATURE:
<223> OTHER INFORMATION: Synthetically generated peptide

<400> SEQUENCE: 45

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Ser Met His Trp Val Arg Gln Ala Pro Gly Lys Gly Leu Glu Trp Val
        35                  40                  45

Ser Ser Ile Gly Pro Ser Gly Gly Lys Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Phe Arg Gly Ser Tyr Tyr Tyr Phe Asp Tyr Trp Gly Gln
            100                 105                 110

Gly Thr
```

<210> SEQ ID NO 46
<211> LENGTH: 115
<212> TYPE: PRT
<213> ORGANISM: Artificial Sequence
<220> FEATURE:
<223> OTHER INFORMATION: Synthetically generated peptide

<400> SEQUENCE: 46

```
Gln Asp Ile Gln Met Thr Gln Ser Pro Ser Ser Leu Ser Ala Ser Ile
 1               5                  10                  15

Gly Asp Arg Val Thr Ile Thr Cys Gln Ala Ser Gln Asp Thr Tyr Asn
            20                  25                  30

Arg Leu His Trp Tyr Gln Gln Lys Ser Gly Lys Ala Pro Lys Leu Leu
        35                  40                  45

Ile Tyr Asp Ala Val Asn Leu Lys Arg Gly Val Pro Ser Arg Phe Arg
    50                  55                  60

Gly Ser Gly Ser Gly Thr Asn Phe Ile Leu Thr Ile Thr Asn Leu Gln
65                  70                  75                  80

Pro Glu Asp Thr Ala Thr Tyr Phe Cys Gln His Ser Asp Asp Leu Ser
                85                  90                  95

Leu Ala Phe Gly Gly Gly Thr Lys Val Glu Ile Lys Arg Thr Val Ala
            100                 105                 110

Ala Pro Ser
        115
```

<210> SEQ ID NO 47
<211> LENGTH: 344
<212> TYPE: DNA

-continued

<213> ORGANISM: Artificial Sequence
<220> FEATURE:
<223> OTHER INFORMATION: Synthetically generated oligonucleotide

<400> SEQUENCE: 47
gaagttcaat tgttagagtc tggtggcggt cttgttcagc ctggtggttc tttacgtctt 60
tcttgcgctg cttccggatt cactttctct cgttactcta tgcattgggt tcgccaagct 120
cctggtaaag gtttggagtg ggtttcttct atcggtcctt ctggtggcaa gactaagtat 180
gctgactccg ttaaaggtcg cttcactatc tctagagaca actctaagaa tactctctac 240
ttgcagatga acagcttaag ggctgaggac actgcagtct actattgtgc gagacccttc 300
cgtgggagct actactactt tgactactgg ggccagggaa ccct 344

<210> SEQ ID NO 48
<211> LENGTH: 345
<212> TYPE: DNA
<213> ORGANISM: Artificial Sequence
<220> FEATURE:
<223> OTHER INFORMATION: Synthetically generated oligonucleotide

<400> SEQUENCE: 48
caagacatcc agatgaccca gtctccatcc tccctgtctg catctatagg agacagagtc 60
accataactt gccaggcgag tcaggacact tacaaccgtc tacattggta tcagcagaaa 120
tcagggaaag cccctaaact cctcatctac gatgcagtca atttgaaaag gggggtccct 180
tcaaggttcc gtggaagtgg atctgggaca aattttattt tgaccatcac caacctgcag 240
cctgaagata ctgcaacata tttctgtcaa cattctgatg atctgtcact cgctttcggc 300
ggagggacca aggtggagat caaacgaact gtggctgcac catct 345

<210> SEQ ID NO 49
<211> LENGTH: 127
<212> TYPE: PRT
<213> ORGANISM: Artificial Sequence
<220> FEATURE:
<223> OTHER INFORMATION: Synthetically generated peptide

<400> SEQUENCE: 49

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Lys Met Trp Trp Val Arg Gln Ala Pro Gly Lys Gly Leu Glu Trp Val
        35                  40                  45

Ser Tyr Ile Ser Pro Ser Gly Gly Tyr Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Ala Arg Arg Ala Phe Pro Ser Met Asp Val Trp Gly Lys
            100                 105                 110

Gly Thr Thr Val Thr Val Ser Ser Ala Ser Thr Lys Gly Pro Ser
        115                 120                 125
```

<210> SEQ ID NO 50
<211> LENGTH: 120
<212> TYPE: PRT
<213> ORGANISM: Artificial Sequence -continued
<220> FEATURE:
<223> OTHER INFORMATION: Synthetically generated peptide

<400> SEQUENCE: 50

Gln Asp Ile Gln Met Thr Gln Ser Pro Leu Ser Leu Pro Val Thr Pro
1 5 10 15

Gly Glu Pro Ala Ser Ile Ser Cys Arg Ser Ser Gln Ser Leu Leu Tyr
20 25 30

Ser Asn Gly Tyr Asn Tyr Leu Asp Trp Tyr Leu Gln Arg Pro Gly Gln
35 40 45

Ser Pro Gln Leu Leu Ile Tyr Leu Gly Ser Asn Arg Ala Ser Gly Val
50 55 60

Pro Asp Arg Phe Ser Gly Ser Gly Ser Gly Thr Asp Phe Thr Leu Lys
65 70 75 80

Ile Ser Arg Val Glu Ala Lys Asp Val Gly Val Tyr Tyr Cys Met Gln
85 90 95

Ala Leu Gln Ile Pro Arg Thr Phe Gly Gln Gly Thr Lys Val Glu Ile
100 105 110

Lys Arg Thr Val Ala Ala Pro Ser
115 120

<210> SEQ ID NO 51
<211> LENGTH: 382
<212> TYPE: DNA
<213> ORGANISM: Artificial Sequence
<220> FEATURE:
<223> OTHER INFORMATION: Synthetically generated oligonucleotide

<400> SEQUENCE: 51
gaagttcaat tgttagagtc tggtggcggt cttgttcagc ctggtggttc tttacgtctt 60
tcttgcgctg cttccggatt cactttctct cgttacaaga tgtggtgggt tcgccaagct 120
cctggtaaag gtttggagtg ggtttcttat atctctcctt ctggtggcta tactggttat 180
gctgactccg ttaaaggtcg cttcactatc tctagagaca actctaagaa tactctctac 240
ttgcagatga acagcttaag ggctgaggac actgcagtct actattgtgc gaaaaacgcg 300
cgaagagctt ttccctccat ggacgtctgg ggcaaaggga ccacggtcac cgtctcaagc 360
gcctccacca agggcccatc gg 382

<210> SEQ ID NO 52
<211> LENGTH: 360
<212> TYPE: DNA
<213> ORGANISM: Artificial Sequence
<220> FEATURE:
<223> OTHER INFORMATION: Synthetically generated oligonucleotide

<400> SEQUENCE: 52
caagacatcc agatgaccca gtctccactc tccctgcccg tcacccctgg agagccggcc 60
tccatctcct gcaggtctag tcagagcctc ctgtatagta atggatacaa ctatttggat 120
tggtacctgc agagaccagg gcagtctcca cagctcctga tctatttggg ttctaatcgg 180
gcctccgggg tccctgacag gttcagtggc agtggatcag gcacagattt cacactgaaa 240
atcagcagag tggaggctaa ggatgttggg gtttattact gcatgcaagc tctacaaatt 300
cctcggacgt tcggccaagg gaccaaggtg gaaatcaaac gaactgtggc tgcaccatct 360

<210> SEQ ID NO 53
<211> LENGTH: 127
<212> TYPE: PRT

-continued

<213> ORGANISM: Artificial Sequence
<220> FEATURE:
<223> OTHER INFORMATION: Synthetically generated peptide

<400> SEQUENCE: 53

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Arg Met His Trp Val Arg Gln Ala Pro Gly Lys Gly Leu Glu Trp Val
        35                  40                  45

Ser Gly Ile Ser Ser Ser Gly Gly Asp Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Ala Arg Arg Ala Phe Pro Ser Met Asp Val Trp Gly Lys
            100                 105                 110

Gly Thr Thr Val Thr Val Ser Ser Ala Ser Thr Lys Gly Pro Ser
        115                 120                 125
```

<210> SEQ ID NO 54
<211> LENGTH: 115
<212> TYPE: PRT
<213> ORGANISM: Artificial Sequence
<220> FEATURE:
<223> OTHER INFORMATION: Synthetically generated peptide

<400> SEQUENCE: 54

```
Gln Asp Ile Gln Met Thr Gln Ser Pro Ser Ser Val Ser Ala Ser Val
 1               5                  10                  15

Gly Asp Thr Val Thr Ile Thr Cys Arg Ala Ser Leu Pro Val Asn Thr
            20                  25                  30

Trp Leu Ala Trp Tyr Gln Gln Lys Pro Gly Lys Ala Pro Lys Leu Leu
        35                  40                  45

Leu Tyr Ala Ala Ser Arg Leu Gln Ser Gly Val Pro Ser Arg Phe Ser
    50                  55                  60

Gly Ser Gly Ser Gly Thr Asp Phe Thr Leu Asn Ile Ser Ser Leu Gln
65                  70                  75                  80

Pro Glu Asp Phe Ala Thr Tyr Tyr Cys Gln Gln Ala Asn Thr Phe Pro
                85                  90                  95

Tyr Thr Phe Gly Gln Gly Thr Lys Val Asp Ile Lys Arg Thr Val Ala
            100                 105                 110

Ala Pro Ser
        115
```

<210> SEQ ID NO 55
<211> LENGTH: 382
<212> TYPE: DNA
<213> ORGANISM: Artificial Sequence
<220> FEATURE:
<223> OTHER INFORMATION: Synthetically generated oligonucleotide

<400> SEQUENCE: 55

```
gaagttcaat tgttagagtc tggtggcggt cttgttcagc ctggtggttc tttacgtctt     60

tcttgcgctg cttccggatt cactttctct cgttaccgta tgcattgggt tcgccaagct    120

cctggtaaag gtttggagtg ggtttctggt atctcttctt ctggtggcga tactaattat    180
```

-continued

```
gctgactccg ttaaaggtcg cttcactatc tctagagaca actctaagaa tactctctac    240

ttgcagatga acagcttaag ggctgaggac actgcagtct actattgtgc gaaaaacgcg    300

cgaagagctt ttccctccat ggacgtctgg ggcaaaggga ccacggtcac cgtctcaagc    360

gcctccacca agggcccatc gg                                             382
```

<210> SEQ ID NO 56
<211> LENGTH: 345
<212> TYPE: DNA
<213> ORGANISM: Artificial Sequence
<220> FEATURE:
<223> OTHER INFORMATION: Synthetically generated oligonucleotide

<400> SEQUENCE: 56

```
caagacatcc agatgaccca gtctccatct tccgtgtctg catctgtagg agacacagtc     60

accatcactt gtcgggcgag tctgcctgtt aacacctggt tagcctggta tcagcagaaa    120

cccgggaaag cccctaaact cctgctctat gctgcatcca gattacaaag tggggtccca    180

tcaaggttca gcggcagtgg ctctgggaca gatttcactc tcaacatcag cagtctgcag    240

cctgaggatt ttgcaaccta ctattgtcaa caggcgaaca ctttcccgta cacttttggc    300

caggggacca aagtggatat caaacgaact gtggctgcac catct                    345
```

<210> SEQ ID NO 57
<211> LENGTH: 127
<212> TYPE: PRT
<213> ORGANISM: Artificial Sequence
<220> FEATURE:
<223> OTHER INFORMATION: Synthetically generated peptide

<400> SEQUENCE: 57

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Ser Met His Trp Val Arg Gln Ala Pro Gly Lys Gly Leu Glu Trp Val
        35                  40                  45

Ser Arg Ile Val Pro Ser Gly Gly Thr Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Ala Arg Arg Ala Phe Pro Ser Met Asp Val Trp Gly Lys
            100                 105                 110

Gly Thr Thr Val Thr Val Ser Ser Ala Ser Thr Lys Gly Pro Ser
        115                 120                 125
```

<210> SEQ ID NO 58
<211> LENGTH: 116
<212> TYPE: PRT
<213> ORGANISM: Artificial Sequence
<220> FEATURE:
<223> OTHER INFORMATION: Synthetically generated peptide

<400> SEQUENCE: 58

```
Gln Ser Ala Leu Thr Gln Asp Pro Ala Val Ser Val Ala Leu Gly Gln
 1               5                  10                  15

Thr Val Arg Ile Thr Cys Gln Gly Asp Ser Leu Arg Ser Tyr Tyr Ala
```

-continued

```
            20                  25                  30

Ser Trp Tyr Gln Gln Lys Pro Gly Gln Ala Pro Val Leu Val Ile Tyr
        35                  40                  45

Ser Lys Ser Asn Arg Pro Ser Gly Ile Pro Asp Arg Phe Ser Gly Ser
    50                  55                  60

Ser Ser Gly Ser Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Leu Val Phe Gly Gly Gly Thr Lys Leu Thr Val Leu Gly Gln Pro Lys
            100                 105                 110

Ala Ala Pro Ser
        115


<210> SEQ ID NO 59
<211> LENGTH: 382
<212> TYPE: DNA
<213> ORGANISM: Artificial Sequence
<220> FEATURE:
<223> OTHER INFORMATION: Synthetically generated oligonucleotide

<400> SEQUENCE: 59

gaagttcaat tgttagagtc tggtggcggt cttgttcagc ctggtggttc tttacgtctt      60

tcttgcgctg cttccggatt cactttctct cgttactcta tgcattgggt tcgccaagct     120

cctggtaaag gtttggagtg ggtttctcgt atcgttcctt ctggtggcac tactttttat     180

gctgactccg ttaaaggtcg cttcactatc tctagagaca actctaagaa tactctctac     240

ttgcagatga acagcttaag ggctgaggac actgcagtct actattgtgc gaaaaacgcg     300

cgaagagctt ttccctccat ggacgtctgg ggcaaaggga ccacggtcac cgtctcaagc     360

gcctccacca agggcccatc gg                                              382


<210> SEQ ID NO 60
<211> LENGTH: 348
<212> TYPE: DNA
<213> ORGANISM: Artificial Sequence
<220> FEATURE:
<223> OTHER INFORMATION: Synthetically generated oligonucleotide

<400> SEQUENCE: 60

cagagcgctt tgactcagga ccctgctgtg tctgtggcct tgggacagac agtcaggatc      60

acatgccaag gagacagcct cagaagctat tatgcaagct ggtaccagca gaagccagga     120

caggcccctg tacttgtcat atatagtaaa agtaaccggc cctcagggat cccagaccga     180

ttctctggct ccagctcagg aagcacagct tccttgacca tcactggggc tcaggcggaa     240

gatgaggctg actattattg taactcccgg gacagcagtg gtaaccatct ggtattcggc     300

ggagggacca agctgaccgt cctaggtcag cccaaggctg ccccctcg                  348


<210> SEQ ID NO 61
<211> LENGTH: 127
<212> TYPE: PRT
<213> ORGANISM: Artificial Sequence
<220> FEATURE:
<223> OTHER INFORMATION: Synthetically generated peptide

<400> SEQUENCE: 61

Glu Val Gln Leu Leu Glu Ser Gly Gly Gly Leu Val Gln Pro Gly Gly
 1               5                  10                  15
```

-continued

Ser Leu Arg Leu Ser Cys Ala Ala Ser Gly Phe Thr Phe Ser Arg Tyr
20 25 30

Asn Met Tyr Trp Val Arg Gln Ala Pro Gly Lys Gly Leu Glu Trp Val
35 40 45

Ser Gly Ile Arg Pro Ser Gly Gly Ser Thr Gln Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asn Ala Arg Arg Ala Phe Pro Ser Met Asp Val Trp Gly Lys
100 105 110

Gly Thr Thr Val Thr Val Ser Ser Ala Ser Thr Lys Gly Pro Ser
115 120 125

<210> SEQ ID NO 62
<211> LENGTH: 115
<212> TYPE: PRT
<213> ORGANISM: Artificial Sequence
<220> FEATURE:
<223> OTHER INFORMATION: Synthetically generated peptide

<400> SEQUENCE: 62

Gln Ser Glu Leu Thr Gln Asp Pro Ala Val Ser Val Ala Leu Gly Gln
1 5 10 15

Thr Val Arg Ile Thr Cys Arg Gly Asp Arg Leu Arg Ser Tyr Tyr Ser
20 25 30

Ser Trp Tyr Gln Gln Lys Pro Arg Gln Ala Pro Val Leu Val Met Phe
35 40 45

Gly Arg Lys Asn Arg Pro Ser Gly Ile Pro Asp Arg Phe Ser Gly Ser
50 55 60

Thr Ser Gly Ser Thr Ala Ser Leu Thr Ile Thr Ala Thr Gln Ala Asp
65 70 75 80

Asp Glu Ala Asp Tyr Phe Cys Ser Ser Arg Asp Gly Ser Gly Asn Phe
85 90 95

Leu Phe Gly Gly Gly Thr Lys Leu Thr Val Leu Gly Gln Pro Lys Ala
100 105 110

Ala Pro Ser
115

<210> SEQ ID NO 63
<211> LENGTH: 382
<212> TYPE: DNA
<213> ORGANISM: Artificial Sequence
<220> FEATURE:
<223> OTHER INFORMATION: Synthetically generated oligonucleotide

<400> SEQUENCE: 63
gaagttcaat tgttagagtc tggtggcggt cttgttcagc ctggtggttc tttacgtctt 60
tcttgcgctg cttccggatt cactttctct cgttacaata tgtattgggt tcgccaagct 120
cctggtaaag gtttggagtg ggtttctggt atccgtcctt ctggtggctc tactcagtat 180
gctgactccg ttaaaggtcg cttcactatc tctagagaca actctaagaa tactctctac 240
ttgcagatga acagcttaag ggctgaggac actgcagtct actattgtgc gaaaaacgcg 300
cgaagagctt ttccctccat ggacgtctgg ggcaaaggga ccacggtcac cgtctcaagc 360
gcctccacca agggcccatc gg 382

-continued

<210> SEQ ID NO 64
<211> LENGTH: 345
<212> TYPE: DNA
<213> ORGANISM: Artificial Sequence
<220> FEATURE:
<223> OTHER INFORMATION: Synthetically generated oligonucleotide

<400> SEQUENCE: 64
cagagcgaat tgactcagga ccctgctgtg tctgtggcct tggggcagac agtcaggatt 60
acatgccgag gagacagact cagaagttat tattcaagtt ggtaccagca gaagccacga 120
caggcccctg ttcttgtcat gtttggtaga aagaaccggc cctcagggat cccagaccga 180
ttctctggct ccacctcagg aagcacagct tccttgacca tcactgcgac tcaggcggac 240
gatgaggctg actatttctg tagttcccgg gacggcagtg gtaatttcct cttcggcgga 300
gggaccaaac tgaccgtcct tggtcagccc aaggctgccc cctcg 345

<210> SEQ ID NO 65
<211> LENGTH: 127
<212> TYPE: PRT
<213> ORGANISM: Artificial Sequence
<220> FEATURE:
<223> OTHER INFORMATION: Synthetically generated peptide

<400> SEQUENCE: 65

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Arg Tyr
20 25 30

Ser Met His Trp Val Arg Gln Ala Pro Gly Lys Gly Leu Glu Trp Val
35 40 45

Ser Gly Ile Arg Pro Ser Gly Gly Ser Thr Lys Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asn Ala Arg Arg Ala Phe Pro Ser Met Asp Val Trp Gly Lys
100 105 110

Gly Thr Thr Val Thr Val Ser Ser Ala Ser Thr Lys Gly Pro Ser
115 120 125

<210> SEQ ID NO 66
<211> LENGTH: 112
<212> TYPE: PRT
<213> ORGANISM: Artificial Sequence
<220> FEATURE:
<223> OTHER INFORMATION: Synthetically generated peptide

<400> SEQUENCE: 66

Gln Asp Ile Gln Met Thr Gln Ser Pro Ser Ser Leu Ser Ala Ser Val
1 5 10 15

Gly Asp Arg Val Thr Ile Thr Cys Arg Ala Ser Gln Ser Ile Ser Thr
20 25 30

Tyr Leu Asn Trp Tyr Gln Gln Arg Pro Gly Glu Ala Pro Lys Leu Leu
35 40 45

Ile Tyr Gly Ala Ser Ser Leu Val Ser Gly Val Pro Ser Arg Phe Ser
50 55 60

Gly Ser Gly Ser Gly Thr Asp Phe Thr Leu Thr Ile Ser Ser Leu Gln

-continued

```
65                  70                  75                  80

Pro Glu Asp Phe Ala Thr Tyr Tyr Cys His Gln Ser Tyr Ile Thr Ser
                85                  90                  95

Trp Thr Phe Gly Gln Gly Thr Lys Val Glu Ile Lys Arg Thr Val Ala
            100                 105                 110
```

<210> SEQ ID NO 67
<211> LENGTH: 382
<212> TYPE: DNA
<213> ORGANISM: Artificial Sequence
<220> FEATURE:
<223> OTHER INFORMATION: Synthetically generated oligonucleotide

<400> SEQUENCE: 67

```
gaagttcaat tgttagagtc tggtggcggt cttgttcagc ctggtggttc tttacgtctt     60

tcttgcgctg cttccggatt cactttctct cgttactcta tgcattgggt tcgccaagct    120

cctggtaaag gtttggagtg ggtttctggt atccgtcctt ctggtggctc tactaagtat    180

gctgactccg ttaaaggtcg cttcactatc tctagagaca actctaagaa tactctctac    240

ttgcagatga acagcttaag ggctgaggac actgcagtct actattgtgc gaaaaacgcg    300

cgaagagctt ttccctccat ggacgtctgg ggcaaaggga ccacggtcac cgtctcaagc    360

gcctccacca agggcccatc gg                                             382
```

<210> SEQ ID NO 68
<211> LENGTH: 345
<212> TYPE: DNA
<213> ORGANISM: Artificial Sequence
<220> FEATURE:
<223> OTHER INFORMATION: Synthetically generated oligonucleotide

<400> SEQUENCE: 68

```
caagacatcc agatgaccca gtctccttcc tccctgtctg catctgtagg agacagagtc     60

accatcactt gccgggcaag tcagagcatt agcacctact taaactggta tcagcagaga    120

ccaggggaag cccctaaact cctgatctat ggtgcatcca gtttggtgag tggggtccca    180

tcaagattta gtggcagcgg atctgggaca gatttcactc tcaccatctc cagtctgcaa    240

cctgaagatt ttgcaactta ctactgtcac cagagttaca ttacctcgtg gacgttcggc    300

caagggacca aggtggaaat caaacgaact gtggctgcac catct                    345
```

<210> SEQ ID NO 69
<211> LENGTH: 112
<212> TYPE: PRT
<213> ORGANISM: Artificial Sequence
<220> FEATURE:
<223> OTHER INFORMATION: Synthetically generated peptide

<400> SEQUENCE: 69

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Arg Met Tyr Trp Val Arg Gln Ala Pro Gly Lys Gly Leu Glu Trp Val
        35                  40                  45

Ser Ser Ile Ser Pro Ser Gly Gly Asp Thr Arg Tyr Ala Asp Ser Val
    50                  55                  60

Lys Gly Arg Phe Thr Ile Ser Arg Asp Asn Ser Asn Thr Leu Tyr Leu
65                  70                  75                  80
```

-continued

```
Gln Met Asn Ser Leu Arg Ala Glu Asp Thr Ala Val Tyr Tyr Cys Ala
                85                  90                  95

Arg Gly Gly Pro Arg Gly Asn Lys Tyr Tyr Phe Asp Tyr Trp Gly Gln
            100                 105                 110
```

<210> SEQ ID NO 70
<211> LENGTH: 112
<212> TYPE: PRT
<213> ORGANISM: Artificial Sequence
<220> FEATURE:
<223> OTHER INFORMATION: Synthetically generated peptide

<400> SEQUENCE: 70

```
Gln Asp Ile Gln Met Thr Gln Ser Pro Ser Phe Leu Ser Ala Phe Val
 1               5                  10                  15

Gly Asp Arg Val Thr Ile Thr Cys Arg Ala Ser Gln Asp Ile Arg Ser
            20                  25                  30

Asp Leu Ala Trp Tyr Gln Gln Thr Pro Gly Lys Ala Pro Lys Leu Leu
        35                  40                  45

Ile Tyr Ala Ala Ser Thr Leu Lys Asp Gly Ala Pro Ser Arg Phe Ser
    50                  55                  60

Gly Ser Gly Ser Gly Thr Glu Phe Thr Leu Thr Ile Ser Ser Leu His
65                  70                  75                  80

Pro Glu Asp Leu Ala Thr Tyr Tyr Cys Gln His Leu Asn Gly His Pro
                85                  90                  95

Ala Phe Gly Pro Gly Thr Lys Val Asn Ile Gln Arg Thr Val Ala Ala
            100                 105                 110
```

<210> SEQ ID NO 71
<211> LENGTH: 341
<212> TYPE: DNA
<213> ORGANISM: Artificial Sequence
<220> FEATURE:
<223> OTHER INFORMATION: Synthetically generated oligonucleotide

<400> SEQUENCE: 71

```
gaagttcaat tgttagagtc tggtggcggt cttgttcagc ctggtggttc tttacgtctt     60

tcttgcgctg cttccggatt cactttctct cgttaccgta tgtattgggt tcgccaagct    120

cctggtaaag gtttggagtg ggtttcttct atctctcctt ctggtggcga tactcgttat    180

gctgactccg ttaaaggtcg cttcactatc tctagagaca actcttagaa tactctctac    240

ttgcagatga acagcttaag ggctgaggac actgcagtct actattgtgc gagaggggga    300

ccgcggggta acaagtacta ctttgactac tggggccagg g                        341
```

<210> SEQ ID NO 72
<211> LENGTH: 337
<212> TYPE: DNA
<213> ORGANISM: Artificial Sequence
<220> FEATURE:
<223> OTHER INFORMATION: Synthetically generated oligonucleotide

<400> SEQUENCE: 72

```
caagacatcc agatgaccca gtctccatcc ttcctgtctg catttgtagg agacagggtc     60

accatcactt gccgggccag tcaggacatt agaagtgatt tagcctggta tcagcaaaca    120

ccagggaaag ccccaaagct cctgatctat gctgcatcca ctttgaaaga tggggcccca    180

tcaagattca gcggcagtgg atctgggaca gaatttactc tcacaatcag cagcctgcac    240

cctgaagatc ttgcgactta ttactgtcaa caccttaatg gtcaccctgc tttcggccct    300
```

-continued gggaccaaag tgaatatcca aagaactgtg gctgcac 337

<210> SEQ ID NO 73
<211> LENGTH: 112
<212> TYPE: PRT
<213> ORGANISM: Artificial Sequence
<220> FEATURE:
<223> OTHER INFORMATION: Synthetically generated peptide

<400> SEQUENCE: 73

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Arg Tyr
20 25 30

Arg Met Tyr Trp Val Arg Gln Ala Pro Gly Lys Gly Leu Glu Trp Val
35 40 45

Ser Ser Ile Ser Pro Ser Gly Gly Asp Thr Arg Tyr Ala Asp Ser Val
50 55 60

Lys Gly Arg Phe Thr Ile Ser Arg Asp Asn Ser Asn Thr Leu Tyr Leu
65 70 75 80

Gln Met Asn Ser Leu Arg Ala Glu Asp Thr Ala Val Tyr Tyr Cys Ala
85 90 95

Arg Gly Gly Pro Arg Gly Asn Lys Tyr Tyr Phe Asp Tyr Trp Gly Gln
100 105 110

<210> SEQ ID NO 74
<211> LENGTH: 111
<212> TYPE: PRT
<213> ORGANISM: Artificial Sequence
<220> FEATURE:
<223> OTHER INFORMATION: Synthetically generated peptide

<400> SEQUENCE: 74

Gln Tyr Glu Leu Thr Gln Pro Pro Ser Val Ser Val Ser Leu Gly Gln
1 5 10 15

Ala Ala Asn Ile Ser Cys Ser Gly Asp Arg Leu Gly Asp Lys Tyr Thr
20 25 30

Ser Trp Tyr Gln Gln Gln Ser Gly Gln Ser Pro Val Leu Val Ile Tyr
35 40 45

Gln Asp Lys Lys Arg Pro Ser Gly Ile Pro Glu Arg Phe Ser Gly Ser
50 55 60

Ser Ser Gly Asn Thr Ala Thr Leu Thr Ile Ser Gly Ala Gln Ala Ile
65 70 75 80

Asp Glu Ala Ala Tyr Tyr Cys Gln Ala Trp Ala Thr Asn Val Val Phe
85 90 95

Gly Ala Gly Thr Lys Leu Thr Val Leu Gly Gln Pro Lys Ala Ala
100 105 110

<210> SEQ ID NO 75
<211> LENGTH: 341
<212> TYPE: DNA
<213> ORGANISM: Artificial Sequence
<220> FEATURE:
<223> OTHER INFORMATION: Synthetically generated oligonucleotide

<400> SEQUENCE: 75
gaagttcaat tgttagagtc tggtggcggt cttgttcagc ctggtggttc tttacgtctt 60
tcttgcgctg cttccggatt cactttctct cgttaccgta tgtattgggt tcgccaagct 120
cctggtaaag gtttggagtg ggtttcttct atctctcctt ctggtggcga tactcgttat 180

-continued

```
gctgactccg ttaaaggtcg cttcactatc tctagagaca actcttagaa tactctctac    240

ttgcagatga acagcttaag ggctgaggac actgcagtct actattgtgc gagaggggga    300

ccgcggggta acaagtacta ctttgactac tggggccagg g                        341
```

<210> SEQ ID NO 76
<211> LENGTH: 334
<212> TYPE: DNA
<213> ORGANISM: Artificial Sequence
<220> FEATURE:
<223> OTHER INFORMATION: Synthetically generated oligonucleotide

<400> SEQUENCE: 76

```
cagtacgaat tgactcagcc accctcagtg tccgtgtccc taggacaggc agccaacatc     60

tcctgctctg gagatagatt gggggataaa tatacttcct ggtatcaaca acagtcagga    120

cagtcccctg tcctggtcat ctatcaagat aagaagcgac cctcagggat ccccgagcga    180

ttctctggct cctcctctgg gaacacagcc actctgacca tcagcggggc ccaggccata    240

gatgaggctg cctattactg tcaggcgtgg gccaccaatg tggttttcgg cgctgggacc    300

aagctgaccg tcctaggtca gcccaaggct gccc                                334
```

<210> SEQ ID NO 77
<211> LENGTH: 112
<212> TYPE: PRT
<213> ORGANISM: Artificial Sequence
<220> FEATURE:
<223> OTHER INFORMATION: Synthetically generated peptide

<400> SEQUENCE: 77

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Arg Met Tyr Trp Val Arg Gln Ala Pro Gly Lys Gly Leu Glu Trp Val
        35                  40                  45

Ser Ser Ile Ser Pro Ser Gly Gly Asp Thr Arg Tyr Ala Asp Ser Val
    50                  55                  60

Lys Gly Arg Phe Thr Ile Ser Arg Asp Asn Ser Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Gly Pro Arg Gly Asn Lys Tyr Tyr Phe Asp Tyr Trp Gly Gln
            100                 105                 110
```

<210> SEQ ID NO 78
<211> LENGTH: 113
<212> TYPE: PRT
<213> ORGANISM: Artificial Sequence
<220> FEATURE:
<223> OTHER INFORMATION: Synthetically generated peptide

<400> SEQUENCE: 78

```
Gln Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Thr Ile Asp Asn
            20                  25                  30

Tyr Leu Asn Trp Tyr Gln Gln Lys Pro Gly Lys Ala Pro Lys Leu Val
        35                  40                  45
```

-continued

```
Val Tyr Ala Ala Ser Thr Leu Gln Thr Arg Val Pro Ser Arg Phe Ser
    50                  55                  60

Gly Ser Gly Ser Gly Thr Asp Phe Thr Leu Thr Ile Asp Ser Leu Lys
65                  70                  75                  80

Pro Glu Asp Phe Ala Thr Tyr Phe Cys Gln Gln Gly Phe Ser Asn Pro
                85                  90                  95

Trp Thr Phe Gly Gln Gly Thr Thr Val Ala Met Ile Arg Thr Val Ala
            100                 105                 110

Ala
```

<210> SEQ ID NO 79
<211> LENGTH: 341
<212> TYPE: DNA
<213> ORGANISM: Artificial Sequence
<220> FEATURE:
<223> OTHER INFORMATION: Synthetically generated oligonucleotide

<400> SEQUENCE: 79

```
gaagttcaat tgttagagtc tggtggcggt cttgttcagc ctggtggttc tttacgtctt     60

tcttgcgctg cttccggatt cactttctct cgttaccgta tgtattgggt tcgccaagct    120

cctggtaaag gtttggagtg ggtttcttct atctctcctt ctggtggcga tactcgttat    180

gctgactccg ttaaaggtcg cttcactatc tctagagaca actcttagaa tactctctac    240

ttgcagatga acagcttaag ggctgaggac actgcagtct actattgtgc gagaggggga    300

ccgcggggta acaagtacta ctttgactac tggggccagg g                        341
```

<210> SEQ ID NO 80
<211> LENGTH: 340
<212> TYPE: DNA
<213> ORGANISM: Artificial Sequence
<220> FEATURE:
<223> OTHER INFORMATION: Synthetically generated oligonucleotide

<400> SEQUENCE: 80

```
caagacatcc agatgaccca gtctccatcc tccctgtctg cttctgttgg agacagagtc     60

accatcactt gccgggcaag ccagaccatt gacaattatt tgaattggta tcagcagaaa    120

ccagggaaag cccccaaact cgtggtctat gctgcatcca ctttgcaaac tagggtccca    180

tcaaggttca gtggcagtgg gtctgggaca gacttcactc tcaccatcga cagtctgaaa    240

cctgaagatt ttgcaactta cttctgtcaa cagggtttca gtaatccttg gacgttcggc    300

caagggacca cggtggcaat gatacgaact gtggctgcac                          340
```

<210> SEQ ID NO 81
<211> LENGTH: 110
<212> TYPE: PRT
<213> ORGANISM: Artificial Sequence
<220> FEATURE:
<223> OTHER INFORMATION: Synthetically generated peptide

<400> SEQUENCE: 81

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Asp Met His Trp Val Arg Gln Ala Pro Gly Lys Gly Leu Glu Trp Val
        35                  40                  45

Ser Ser Ile Ser Ser Ser Gly Gly Tyr Thr Ala Tyr Ala Asp Ser Val
    50                  55                  60
```

-continued

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Arg Gly Thr Ser Gln Gly Tyr Trp Gly Gln
            100                 105                 110
```

<210> SEQ ID NO 82
<211> LENGTH: 115
<212> TYPE: PRT
<213> ORGANISM: Artificial Sequence
<220> FEATURE:
<223> OTHER INFORMATION: Synthetically generated peptide

<400> SEQUENCE: 82

```
Gln Asp Ile Gln Met Thr Gln Ser Pro Gly Thr Leu Ser Leu Ser Pro
 1               5                  10                  15

Gly Glu Arg Gly Thr Leu Ser Cys Arg Ala Ser Gln Phe Val Ser Tyr
            20                  25                  30

Ser Tyr Leu Ala Trp Tyr Gln Gln Lys Pro Gly Gln Ala Pro Arg Leu
        35                  40                  45

Leu Ile Tyr Gly Ala Ser Ser Arg Ala Lys Gly Ile Pro Asp Arg Phe
    50                  55                  60

Ser Gly Ser Gly Ser Gly Thr Asp Phe Thr Leu Thr Ile Thr Arg Leu
65                  70                  75                  80

Glu Pro Glu Asp Phe Ala Val Tyr Tyr Cys Gln Gln Tyr Val Pro Ser
                85                  90                  95

Val Pro Trp Thr Phe Gly Gln Gly Thr Lys Val Glu Val Lys Arg Thr
            100                 105                 110

Val Ala Ala
        115
```

<210> SEQ ID NO 83
<211> LENGTH: 332
<212> TYPE: DNA
<213> ORGANISM: Artificial Sequence
<220> FEATURE:
<223> OTHER INFORMATION: Synthetically generated oligonucleotide

<400> SEQUENCE: 83

```
gaagttcaat tgttagagtc tggtggcggt cttgttcagc ctggtggttc tttacgtctt      60

tcttgcgctg cttccggatt cactttctct cgttacgata tgcattgggt tcgccaagct     120

cctggtaaag gtttggagtg ggtttcttct atctcttctt ctggtggcta tactgcttat     180

gctgactccg ttaaaggtcg cttcactatc tctagagaca actctaagaa tactctctac     240

ttgcagatga acagcttaag ggctgaggac actgcagtct actattgtgc gagaggcgcc     300

cgaggtacca gccaaggcta ctggggccag gg                                   332
```

<210> SEQ ID NO 84
<211> LENGTH: 346
<212> TYPE: DNA
<213> ORGANISM: Artificial Sequence
<220> FEATURE:
<223> OTHER INFORMATION: Synthetically generated oligonucleotide

<400> SEQUENCE: 84

```
caagacatcc agatgactca gtctccaggc accctgtcat tgtctccagg ggaaagaggc      60

accctctcct gcagggccag tcagtttgtt agttacagct acttagcctg gtaccagcag     120
```

-continued

```
aagcctggcc aggctccccg gctcctcatc tatggcgcat ccagcagggc caaaggcatc    180

ccagacaggt tcagtggcag tgggtctggg acagacttca ctctcaccat caccagactg    240

gagcctgaag actttgcagt ttattactgt cagcagtatg ttccctcagt tccgtggacg    300

ttcggccaag ggaccaaggt ggaagtcaaa cgaactgtgg ctgcac                   346
```

<210> SEQ ID NO 85
<211> LENGTH: 113
<212> TYPE: PRT
<213> ORGANISM: Artificial Sequence
<220> FEATURE:
<223> OTHER INFORMATION: Synthetically generated peptide

<400> SEQUENCE: 85

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

His Met Trp Trp Val Arg Gln Ala Pro Gly Lys Gly Leu Glu Trp Val
        35                  40                  45

Ser Gly Ile Ser Ser Ser Arg Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Pro Arg Gly Asn Lys Tyr Tyr Phe Asp Tyr Trp Gly
            100                 105                 110

Gln
```

<210> SEQ ID NO 86
<211> LENGTH: 114
<212> TYPE: PRT
<213> ORGANISM: Artificial Sequence
<220> FEATURE:
<223> OTHER INFORMATION: Synthetically generated peptide

<400> SEQUENCE: 86

```
Gln Asp Ile Gln Met Thr Gln Ser Pro Gly Thr Leu Ser Leu Ser Pro
 1               5                  10                  15

Gly Glu Arg Val Thr Leu Ser Cys Arg Ala Ser Gln Ser Val Thr Ser
            20                  25                  30

Ser Asp Leu Ala Trp Tyr Gln Gln Lys Pro Gly Gln Ala Pro Arg Leu
        35                  40                  45

Leu Ile Ser Gly Ala Ser Ser Arg Ala Thr Gly Ile Pro Asp Arg Phe
    50                  55                  60

Ser Gly Ser Gly Ser Gly Thr Asp Phe Thr Leu Thr Ile Ser Arg Leu
65                  70                  75                  80

Glu Pro Glu Asp Phe Ala Val Tyr Tyr Cys Gln Gln Tyr Gly Asn Ser
                85                  90                  95

Pro Gly Thr Phe Gly Gln Gly Thr Lys Val Glu Ile Lys Arg Thr Val
            100                 105                 110

Ala Ala
```

<210> SEQ ID NO 87
<211> LENGTH: 341
<212> TYPE: DNA

-continued

<213> ORGANISM: Artificial Sequence
<220> FEATURE:
<223> OTHER INFORMATION: Synthetically generated oligonucleotide

<400> SEQUENCE: 87
gaagttcaat tgttagagtc tggtggcggt cttgttcagc ctggtggttc tttacgtctt 60
tcttgcgctg cttccggatt cactttctct cgttaccata tgtggtgggt tcgccaagct 120
cctggtaaag gtttggagtg ggtttctggt atctcttctt ctcgtggcat tactaagtat 180
gctgactccg ttaaaggtcg cttcactatc tctagagaca actctaagaa tactctctac 240
ttgcagatga acagcttaag ggctgaggac actgcagtct actattgtgc gagaggggga 300
ccgcggggta acaagtacta ctttgactac tggggccagg g 341

<210> SEQ ID NO 88
<211> LENGTH: 343
<212> TYPE: DNA
<213> ORGANISM: Artificial Sequence
<220> FEATURE:
<223> OTHER INFORMATION: Synthetically generated oligonucleotide

<400> SEQUENCE: 88
caagacatcc agatgaccca gtctccaggc accctgtctt tgtctccagg ggaaagagtc 60
accctctcct gcagggccag tcagagtgtt accagcagcg acttagcctg gtaccagcag 120
aaacctggtc aggctcccag gctcctcatt tctggtgcat ccagcagggc cactggcatc 180
ccagacaggt tcagtggcag tgggtctggg acagacttca ccctcaccat cagcagactg 240
gaacctgaag attttgcagt gtattactgt cagcagtatg gtaactcacc tgggacgttc 300
ggccaaggga ccaaggtgga aatcaaacga actgtggctg cac 343

<210> SEQ ID NO 89
<211> LENGTH: 113
<212> TYPE: PRT
<213> ORGANISM: Artificial Sequence
<220> FEATURE:
<223> OTHER INFORMATION: Synthetically generated peptide

<400> SEQUENCE: 89

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Arg Tyr
20 25 30

Arg Met Tyr Trp Val Arg Gln Ala Pro Gly Lys Gly Leu Glu Trp Val
35 40 45

Ser Ser Ile Ser Pro Ser Gly Gly Asp Thr Arg Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Gly Gly Pro Arg Gly Asn Lys Tyr Tyr Phe Asp Tyr Trp Gly
100 105 110

Gln

<210> SEQ ID NO 90
<211> LENGTH: 114
<212> TYPE: PRT
<213> ORGANISM: Artificial Sequence
<220> FEATURE:

-continued

<223> OTHER INFORMATION: Synthetically generated peptide

<400> SEQUENCE: 90

Gln Asp Ile Gln Met Thr Gln Ser Pro Gly Thr Leu Ser Leu Ser Pro
 1               5                  10                  15

Gly Glu Arg Ala Thr Leu Ser Cys Arg Ala Ser Gln Ser Val Ser Ser
            20                  25                  30

Ser Tyr Leu Ala Trp Tyr Gln Gln Lys Pro Gly Gln Ala Pro Arg Leu
        35                  40                  45

Leu Ile Tyr Gly Ala Ser Ser Arg Ala Thr Gly Ile Pro Asp Arg Phe
    50                  55                  60

Ser Gly Ser Gly Ser Gly Thr Asp Phe Thr Leu Thr Ile Ser Arg Leu
65                  70                  75                  80

Glu Pro Glu Asp Phe Ala Val Tyr Tyr Cys Gln Gln Tyr Gly Ser Ser
                85                  90                  95

Thr Trp Thr Phe Gly Gln Gly Thr Lys Val Glu Ile Lys Arg Thr Val
            100                 105                 110

Ala Ala

<210> SEQ ID NO 91
<211> LENGTH: 341
<212> TYPE: DNA
<213> ORGANISM: Artificial Sequence
<220> FEATURE:
<223> OTHER INFORMATION: Synthetically generated oligonucleotide

<400> SEQUENCE: 91
gaagttcaat tgttagagtc tggtggcggt cttgttcagc ctggtggttc tttacgtctt 60
tcttgcgctg cttccggatt cactttctct cgttaccgta tgtattgggt tcgccaagct 120
cctggtaaag gtttggagtg ggtttcttct atctctcctt ctggtggcga tactcgttat 180
gctgactccg ttaaaggtcg cttcactatc tctagagaca actcttagaa tactctctac 240
ttgcagatga acagcttaag ggctgaggac actgcagtct actattgtgc gagaggggga 300
ccgcggggta acaagtacta ctttgactac tggggccagg g 341

<210> SEQ ID NO 92
<211> LENGTH: 343
<212> TYPE: DNA
<213> ORGANISM: Artificial Sequence
<220> FEATURE:
<223> OTHER INFORMATION: Synthetically generated oligonucleotide

<400> SEQUENCE: 92
caagacatcc agatgaccca gtctccaggc accctgtctt tgtctccagg ggaaagagcc 60
accctctcct gcagggccag tcagagtgtt agcagcagct acttagcctg gtaccagcag 120
aaacctggcc aggctcccag gctcctcatc tatggtgcat ccagcagggc cactggcatc 180
ccagacaggt tcagtggcag tgggtctggg acagacttca ctctcaccat cagcagactg 240
gagcctgaag attttgcagt gtattactgt cagcagtatg gtagctcaac gtggacgttc 300
ggccaaggga ccaaagtgga aatcaaacga actgtggctg cac 343

<210> SEQ ID NO 93
<211> LENGTH: 1689
<212> TYPE: DNA
<213> ORGANISM: Homo sapiens

<400> SEQUENCE: 93

-continued

```
atggagaggg acagccacgg gaatgcatct ccagcaagaa caccttcagc tggagcatct     60

ccagcccagg catctccagc tgggacacct ccaggccggg catctccagc ccaggcatct    120

ccagcccagg catctccagc tgggacacct ccgggccggg catctccagc ccaggcatct    180

ccagctggta cacctccagg ccgggcatct ccaggccggg catctccagc ccaggcatct    240

ccagcccggg catctccggc tctggcatca ctttccaggt cctcatccgg caggtcatca    300

tccgccaggt cagcctcggt gacaacctcc ccaaccagag tgtaccttgt tagagcaaca    360

ccagtggggg ctgtacccat ccgatcatct cctgccaggt cagcaccagc aaccagggcc    420

accagggaga gcccaggtac gagcctgccc aagttcacct ggcgggaggg ccagaagcag    480

ctaccgctca tcgggtgcgt gctcctcctc attgccctgg tggtttcgct catcatcctc    540

ttccagttct ggcagggcca cacagggatc aggtacaagg agcagaggga gagctgtccc    600

aagcacgctg ttcgctgtga cggggtggtg gactgcaagc tgaagagtga cgagctgggc    660

tgcgtgaggt ttgactggga caagtctctg cttaaaatct actctgggtc ctcccatcag    720

tggcttccca tctgtagcag caactggaat gactcctact cagagaagac ctgccagcag    780

ctgggtttcg agagtgctca ccggacaacc gaggttgccc acagggattt tgccaacagc    840

ttctcaatct tgagatacaa ctccaccatc caggaaagcc tccacaggtc tgaatgccct    900

tcccagcggt atatctccct ccagtgttcc cactgcggac tgagggccat gaccgggcgg    960

atcgtgggag ggcgctggc ctcggatagc aagtggcctt ggcaagtgag tctgcacttc    1020

ggcaccaccc acatctgtgg aggcacgctc attgacgccc agtgggtgct cactgccgcc   1080

cactgcttct tcgtgacccg ggagaaggtc ctggagggct ggaaggtgta cgcgggcacc   1140

agcaacctgc accagttgcc tgaggcagcc tccattgccg agatcatcat caacagcaat   1200

tacaccgatg aggaggacga ctatgacatc gccctcatgc ggctgtccaa gcccctgacc   1260

ctgtccgctc acatccaccc tgcttgcctc cccatgcatg gacagacctt tagcctcaat   1320

gagacctgct ggatcacagg ctttggcaag accagggaga cagatgacaa gacatccccc   1380

ttcctccggg aggtgcaggt caatctcatc gacttcaaga aatgcaatga ctacttggtc   1440

tatgacagtt accttacccc aaggatgatg tgtgctgggg accttcgtgg gggcagagac   1500

tcctgccagg gagacagcgg ggggcctctt gtctgtgagc agaacaaccg ctggtacctg   1560

gcaggtgtca ccagctgggg cacaggctgt ggccagagaa acaaacctgg tgtgtacacc   1620

aaagtgacag aagttcttcc ctggatttac agcaagatgg agagcgaggt gcgattcata   1680

aaatcctaa                                                           1689
```

<210> SEQ ID NO 94
<211> LENGTH: 562
<212> TYPE: PRT
<213> ORGANISM: Homo sapiens

<400> SEQUENCE: 94

```
Met Glu Arg Asp Ser His Gly Asn Ala Ser Pro Ala Arg Thr Pro Ser
 1               5                  10                  15

Ala Gly Ala Ser Pro Ala Gln Ala Ser Pro Ala Gly Thr Pro Pro Gly
            20                  25                  30

Arg Ala Ser Pro Ala Gln Ala Ser Pro Ala Gln Ala Ser Pro Ala Gly
        35                  40                  45

Thr Pro Pro Gly Arg Ala Ser Pro Ala Gln Ala Ser Pro Ala Gly Thr
    50                  55                  60

Pro Pro Gly Arg Ala Ser Pro Gly Arg Ala Ser Pro Ala Gln Ala Ser
```

-continued

```
65                  70                  75                  80

Pro Ala Arg Ala Ser Pro Ala Leu Ala Ser Leu Ser Arg Ser Ser Ser
                85                  90                  95

Gly Arg Ser Ser Ser Ala Arg Ser Ala Ser Val Thr Thr Ser Pro Thr
            100                 105                 110

Arg Val Tyr Leu Val Arg Ala Thr Pro Val Gly Ala Val Pro Ile Arg
        115                 120                 125

Ser Ser Pro Ala Arg Ser Ala Pro Ala Thr Arg Ala Thr Arg Glu Ser
    130                 135                 140

Pro Gly Thr Ser Leu Pro Lys Phe Thr Trp Arg Glu Gly Gln Lys Gln
145                 150                 155                 160

Leu Pro Leu Ile Gly Cys Val Leu Leu Leu Ile Ala Leu Val Val Ser
                165                 170                 175

Leu Ile Ile Leu Phe Gln Phe Trp Gln Gly His Thr Gly Ile Arg Tyr
            180                 185                 190

Lys Glu Gln Arg Glu Ser Cys Pro Lys His Ala Val Arg Cys Asp Gly
        195                 200                 205

Val Val Asp Cys Lys Leu Lys Ser Asp Glu Leu Gly Cys Val Arg Phe
    210                 215                 220

Asp Trp Asp Lys Ser Leu Leu Lys Ile Tyr Ser Gly Ser Ser His Gln
225                 230                 235                 240

Trp Leu Pro Ile Cys Ser Ser Asn Trp Asn Asp Ser Tyr Ser Glu Lys
                245                 250                 255

Thr Cys Gln Gln Leu Gly Phe Glu Ser Ala His Arg Thr Thr Glu Val
            260                 265                 270

Ala His Arg Asp Phe Ala Asn Ser Phe Ser Ile Leu Arg Tyr Asn Ser
        275                 280                 285

Thr Ile Gln Glu Ser Leu His Arg Ser Glu Cys Pro Ser Gln Arg Tyr
    290                 295                 300

Ile Ser Leu Gln Cys Ser His Cys Gly Leu Arg Ala Met Thr Gly Arg
305                 310                 315                 320

Ile Val Gly Gly Ala Leu Ala Ser Asp Ser Lys Trp Pro Trp Gln Val
                325                 330                 335

Ser Leu His Phe Gly Thr Thr His Ile Cys Gly Gly Thr Leu Ile Asp
            340                 345                 350

Ala Gln Trp Val Leu Thr Ala Ala His Cys Phe Phe Val Thr Arg Glu
        355                 360                 365

Lys Val Leu Glu Gly Trp Lys Val Tyr Ala Gly Thr Ser Asn Leu His
    370                 375                 380

Gln Leu Pro Glu Ala Ala Ser Ile Ala Glu Ile Ile Ile Asn Ser Asn
385                 390                 395                 400

Tyr Thr Asp Glu Glu Asp Asp Tyr Asp Ile Ala Leu Met Arg Leu Ser
                405                 410                 415

Lys Pro Leu Thr Leu Ser Ala His Ile His Pro Ala Cys Leu Pro Met
            420                 425                 430

His Gly Gln Thr Phe Ser Leu Asn Glu Thr Cys Trp Ile Thr Gly Phe
        435                 440                 445

Gly Lys Thr Arg Glu Thr Asp Asp Lys Thr Ser Pro Phe Leu Arg Glu
    450                 455                 460

Val Gln Val Asn Leu Ile Asp Phe Lys Lys Cys Asn Asp Tyr Leu Val
465                 470                 475                 480

Tyr Asp Ser Tyr Leu Thr Pro Arg Met Met Cys Ala Gly Asp Leu Arg
                485                 490                 495
```

-continued

```
Gly Gly Arg Asp Ser Cys Gln Gly Asp Ser Gly Gly Pro Leu Val Cys
            500                 505                 510

Glu Gln Asn Asn Arg Trp Tyr Leu Ala Gly Val Thr Ser Trp Gly Thr
        515                 520                 525

Gly Cys Gly Gln Arg Asn Lys Pro Gly Val Tyr Thr Lys Val Thr Glu
    530                 535                 540

Val Leu Pro Trp Ile Tyr Ser Lys Met Glu Ser Glu Val Arg Phe Ile
545                 550                 555                 560

Lys Ser


<210> SEQ ID NO 95
<211> LENGTH: 5
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 2, 4
<223> OTHER INFORMATION: Xaa = any amino acid

<400> SEQUENCE: 95

Tyr Xaa Met Xaa Trp
 1               5


<210> SEQ ID NO 96
<211> LENGTH: 5
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 3, 5
<223> OTHER INFORMATION: Xaa = any amino acid

<400> SEQUENCE: 96

Arg Tyr Xaa Met Xaa
 1               5


<210> SEQ ID NO 97
<211> LENGTH: 5
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 3
<223> OTHER INFORMATION: Xaa = Ser, Arg, Lys
<220> FEATURE:
<221> NAME/KEY: VARIANT
<222> LOCATION: 5
<223> OTHER INFORMATION: Xaa = Ser, Tyr, Trp, His

<400> SEQUENCE: 97

Arg Tyr Xaa Met Xaa
 1               5


<210> SEQ ID NO 98
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
```

-continued

<222> LOCATION: 4, 5, 7-9
<223> OTHER INFORMATION: Xaa = any amino acid
<220> FEATURE:
<221> NAME/KEY: VARIANT
<222> LOCATION: 1, 2
<223> OTHER INFORMATION: Xaa = Ile or Ser
<220> FEATURE:
<221> NAME/KEY: VARIANT
<222> LOCATION: 10
<223> OTHER INFORMATION: Xaa = may be absent

<400> SEQUENCE: 98

Xaa Xaa Ser Xaa Xaa Gly Xaa Xaa Xaa Xaa Tyr Ala Asp Ser
1 5 10

<210> SEQ ID NO 99
<211> LENGTH: 12
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Gly, Asn
<220> FEATURE:
<221> NAME/KEY: VARIANT
<222> LOCATION: 2, 5
<223> OTHER INFORMATION: Xaa = Ala, Gly
<220> FEATURE:
<221> NAME/KEY: VARIANT
<222> LOCATION: 3
<223> OTHER INFORMATION: Xaa = Arg, Pro
<220> FEATURE:
<221> NAME/KEY: VARIANT
<222> LOCATION: 6
<223> OTHER INFORMATION: Xaa = Phe, Asn
<220> FEATURE:
<221> NAME/KEY: VARIANT
<222> LOCATION: 7
<223> OTHER INFORMATION: Xaa = Lys, Pro
<220> FEATURE:
<221> NAME/KEY: VARIANT
<222> LOCATION: 8
<223> OTHER INFORMATION: Xaa = Ser, Tyr
<220> FEATURE:
<221> NAME/KEY: VARIANT
<222> LOCATION: 9
<223> OTHER INFORMATION: Xaa = Met, Tyr
<220> FEATURE:
<221> NAME/KEY: VARIANT
<222> LOCATION: 10
<223> OTHER INFORMATION: Xaa = Phe, Asp
<220> FEATURE:
<221> NAME/KEY: VARIANT
<222> LOCATION: 11
<223> OTHER INFORMATION: Xaa = Val, Asp

<400> SEQUENCE: 99

Xaa Xaa Xaa Arg Xaa Xaa Xaa Xaa Xaa Xaa Xaa Tyr
1 5 10

<210> SEQ ID NO 100
<211> LENGTH: 12
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Gly, Arg, Asn
<220> FEATURE:
<221> NAME/KEY: VARIANT
<222> LOCATION: 2, 5

-continued

<223> OTHER INFORMATION: Xaa = Ala, Gly
<220> FEATURE:
<221> NAME/KEY: VARIANT
<222> LOCATION: 3
<223> OTHER INFORMATION: Xaa = Arg, Pro
<220> FEATURE:
<221> NAME/KEY: VARIANT
<222> LOCATION: 4
<223> OTHER INFORMATION: Xaa = Gly, Arg
<220> FEATURE:
<221> NAME/KEY: VARIANT
<222> LOCATION: 6
<223> OTHER INFORMATION: Xaa = Phe, Asn, Glu
<220> FEATURE:
<221> NAME/KEY: VARIANT
<222> LOCATION: 7
<223> OTHER INFORMATION: Xaa = Val, Lys, Pro
<220> FEATURE:
<221> NAME/KEY: VARIANT
<222> LOCATION: 8
<223> OTHER INFORMATION: Xaa = Ala, Ser, Tyr
<220> FEATURE:
<221> NAME/KEY: VARIANT
<222> LOCATION: 9
<223> OTHER INFORMATION: Xaa = Met, Tyr, Phe
<220> FEATURE:
<221> NAME/KEY: VARIANT
<222> LOCATION: 10
<223> OTHER INFORMATION: Xaa = Phe, Asp
<220> FEATURE:
<221> NAME/KEY: VARIANT
<222> LOCATION: 11
<223> OTHER INFORMATION: Xaa = Ile, Val, Asp

<400> SEQUENCE: 100

Xaa Xaa Xaa Xaa Xaa Xaa Xaa Xaa Xaa Xaa Xaa Tyr
 1               5                   10

<210> SEQ ID NO 101
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 101

Gly Pro Arg Gly Asn Lys Tyr Tyr
 1               5

<210> SEQ ID NO 102
<211> LENGTH: 6
<212> TYPE: PRT
<213> ORGANISM: Artificial Sequence
<220> FEATURE:
<223> OTHER INFORMATION: Synthetically generated peptide

<400> SEQUENCE: 102

Ala Arg Gly Thr Ser Gln
 1               5

<210> SEQ ID NO 103
<211> LENGTH: 12
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 6
<223> OTHER INFORMATION: Xaa = Ile, Val
<220> FEATURE:
<221> NAME/KEY: VARIANT
<222> LOCATION: 8

-continued

<223> OTHER INFORMATION: Xaa = Ser, Thr
<220> FEATURE:
<221> NAME/KEY: VARIANT
<222> LOCATION: 9
<223> OTHER INFORMATION: Xaa = Ser, Tyr
<220> FEATURE:
<221> NAME/KEY: VARIANT
<222> LOCATION: 10
<223> OTHER INFORMATION: Xaa = Leu, Tyr
<220> FEATURE:
<221> NAME/KEY: VARIANT
<222> LOCATION: 11
<223> OTHER INFORMATION: Xaa = Ala, Leu, Asn

<400> SEQUENCE: 103

Arg Ala Ser Gln Ser Xaa Ser Xaa Xaa Xaa Xaa Ala
1 5 10

<210> SEQ ID NO 104
<211> LENGTH: 12
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 4
<223> OTHER INFORMATION: Xaa = Leu, Gln
<220> FEATURE:
<221> NAME/KEY: VARIANT
<222> LOCATION: 5
<223> OTHER INFORMATION: Xaa = Ser, Thr, Phe, Asp, Pro
<220> FEATURE:
<221> NAME/KEY: VARIANT
<222> LOCATION: 6
<223> OTHER INFORMATION: Xaa = Ile, Val
<220> FEATURE:
<221> NAME/KEY: VARIANT
<222> LOCATION: 7
<223> OTHER INFORMATION: Xaa = Ser, Thr, Arg, Asp, Asn
<220> FEATURE:
<221> NAME/KEY: VARIANT
<222> LOCATION: 8
<223> OTHER INFORMATION: Xaa = Ser, Thr, Tyr, Asn
<220> FEATURE:
<221> NAME/KEY: VARIANT
<222> LOCATION: 9
<223> OTHER INFORMATION: Xaa = Ser, Tyr, Trp, Asp
<220> FEATURE:
<221> NAME/KEY: VARIANT
<222> LOCATION: 10
<223> OTHER INFORMATION: Xaa = leu, Tyr, Asp
<220> FEATURE:
<221> NAME/KEY: VARIANT
<222> LOCATION: 11
<223> OTHER INFORMATION: Xaa = Ala, Leu, Asn

<400> SEQUENCE: 104

Arg Ala Ser Xaa Xaa Xaa Xaa Xaa Xaa Xaa Xaa Ala
1 5 10

<210> SEQ ID NO 105
<211> LENGTH: 7
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1, 6, 7
<223> OTHER INFORMATION: Xaa = any amino acid

<400> SEQUENCE: 105

Xaa Ala Ser Ser Leu Xaa Xaa

-continued

```
 1               5


<210> SEQ ID NO 106
<211> LENGTH: 7
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Ala,  Gly
<220> FEATURE:
<221> NAME/KEY: VARIANT
<222> LOCATION: 4
<223> OTHER INFORMATION: Xaa = Ser, Thr, Arg
<220> FEATURE:
<221> NAME/KEY: VARIANT
<222> LOCATION: 5
<223> OTHER INFORMATION: Xaa = Leu, Arg
<220> FEATURE:
<221> NAME/KEY: VARIANT
<222> LOCATION: 6
<223> OTHER INFORMATION: Xaa = Ala, Val, Lys, Gln
<220> FEATURE:
<221> NAME/KEY: VARIANT
<222> LOCATION: 7
<223> OTHER INFORMATION: Xaa = ser, Thr, Lys, Asp

<400> SEQUENCE: 106

Xaa Ala Ser Xaa Xaa Xaa Xaa
 1               5


<210> SEQ ID NO 107
<211> LENGTH: 10
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 3-6, 8, 10
<223> OTHER INFORMATION: Xaa = any amino acid

<400> SEQUENCE: 107

Gln Gln Xaa Xaa Xaa Xaa Pro Xaa Thr Xaa
 1               5                  10


<210> SEQ ID NO 108
<211> LENGTH: 10
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 3
<223> OTHER INFORMATION: Xaa = Ala, Gly, Ser, Leu, Tyr
<220> FEATURE:
<221> NAME/KEY: VARIANT
<222> LOCATION: 4
<223> OTHER INFORMATION: Xaa = Gly, thr, Val, Tyr, Phe, Asn
<220> FEATURE:
<221> NAME/KEY: VARIANT
<222> LOCATION: 5
<223> OTHER INFORMATION: Xaa = Gly, Ser, Thr, Ile, Asn, Pro
<220> FEATURE:
<221> NAME/KEY: VARIANT
<222> LOCATION: 6
<223> OTHER INFORMATION: Xaa = Ser, Thr, Tyr, Phe, Asn
<220> FEATURE:
<221> NAME/KEY: VARIANT
<222> LOCATION: 7
<223> OTHER INFORMATION: Xaa = Ser, Thr, Val, Pro
```

-continued

<220> FEATURE:
<221> NAME/KEY: VARIANT
<222> LOCATION: 8
<223> OTHER INFORMATION: Xaa = Ala, Gly, Ser, Tyr, Trp, Pro
<220> FEATURE:
<221> NAME/KEY: VARIANT
<222> LOCATION: 9
<223> OTHER INFORMATION: Xaa = Thr, Ile, Trp

<400> SEQUENCE: 108

Gln Gln Xaa Xaa Xaa Xaa Xaa Xaa Xaa Thr
1 5 10

<210> SEQ ID NO 109
<211> LENGTH: 12
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 2, 4-8, 10
<223> OTHER INFORMATION: Xaa = any amino acid

<400> SEQUENCE: 109

Ser Xaa Asp Xaa Xaa Xaa Xaa Xaa Tyr Xaa Ser Trp
1 5 10

<210> SEQ ID NO 110
<211> LENGTH: 13
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 5, 7-9
<223> OTHER INFORMATION: Xaa = any amino acid
<220> FEATURE:
<221> NAME/KEY: VARIANT
<222> LOCATION: 6
<223> OTHER INFORMATION: Xaa = Val or Ile
<220> FEATURE:
<221> NAME/KEY: VARIANT
<222> LOCATION: 10
<223> OTHER INFORMATION: Xaa = may be absent
<220> FEATURE:
<221> NAME/KEY: VARIANT
<222> LOCATION: 12
<223> OTHER INFORMATION: Xaa = Ala or Asn

<400> SEQUENCE: 110

Arg Ala Ser Gln Xaa Xaa Xaa Xaa Xaa Xaa Leu Xaa Trp
1 5 10

<210> SEQ ID NO 111
<211> LENGTH: 8
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 3
<223> OTHER INFORMATION: Xaa = Ser or Thr
<220> FEATURE:
<221> NAME/KEY: VARIANT
<222> LOCATION: 4
<223> OTHER INFORMATION: Xaa = Arg or Leu
<220> FEATURE:
<221> NAME/KEY: VARIANT
<222> LOCATION: 5, 6
<223> OTHER INFORMATION: Xaa = any amino acid -continued

<400> SEQUENCE: 111

Ala Ser Xaa Xaa Xaa Xaa Gly Arg
 1               5

<210> SEQ ID NO 112
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1, 3
<223> OTHER INFORMATION: Xaa = Gly, Ser, Val, Tyr, Arg
<220> FEATURE:
<221> NAME/KEY: VARIANT
<222> LOCATION: 4
<223> OTHER INFORMATION: Xaa = Ser, Pro
<220> FEATURE:
<221> NAME/KEY: VARIANT
<222> LOCATION: 6
<223> OTHER INFORMATION: Xaa = Gly, Arg
<220> FEATURE:
<221> NAME/KEY: VARIANT
<222> LOCATION: 8
<223> OTHER INFORMATION: Xaa = Ser, Thr, Ile, Met, Tyr, Phe, Lys, Asp
<220> FEATURE:
<221> NAME/KEY: VARIANT
<222> LOCATION: 10
<223> OTHER INFORMATION: Xaa = Ala, Gly, Thr, Phe, Arg, Lys, Asn, Gln

<400> SEQUENCE: 112

Xaa Ile Xaa Xaa Ser Xaa Gly Xaa Thr Xaa Tyr Ala Asp Ser Val Lys
 1               5                   10                  15

Gly

<210> SEQ ID NO 113
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Gly, Ser, Tyr
<220> FEATURE:
<221> NAME/KEY: VARIANT
<222> LOCATION: 3
<223> OTHER INFORMATION: Xaa = Ser, Val, Arg
<220> FEATURE:
<221> NAME/KEY: VARIANT
<222> LOCATION: 4
<223> OTHER INFORMATION: Xaa = Ser, Pro
<220> FEATURE:
<221> NAME/KEY: VARIANT
<222> LOCATION: 8
<223> OTHER INFORMATION: Xaa = Ser, Ile, Tyr, Asp
<220> FEATURE:
<221> NAME/KEY: VARIANT
<222> LOCATION: 10
<223> OTHER INFORMATION: Xaa = Gly, Arg, Lys, Asn

<400> SEQUENCE: 113

Xaa Ile Xaa Xaa Ser Gly Gly Xaa Thr Xaa Tyr Ala Asp Ser Val Lys
 1               5                   10                  15

Gly